US006552016B1

(12) United States Patent
Baxter et al.

(10) Patent No.: US 6,552,016 B1
(45) Date of Patent: Apr. 22, 2003

(54) MEDIATORS OF HEDGEHOG SIGNALING PATHWAYS, COMPOSITIONS AND USES RELATED THERETO

(75) Inventors: Anthony David Baxter, Bishops Stortford (GB); Edward Andrew Boyd, Didcot (GB); Oivin M. Guicherit, Belmont, MA (US); Stephen Price, Aylesbury (GB); Lee Rubin, Wellesley, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/688,018

(22) Filed: Oct. 13, 2000

Related U.S. Application Data

(60) Provisional application No. 60/240,536, filed on Oct. 13, 2000, provisional application No. 60/211,919, filed on Jun. 16, 2000, provisional application No. 60/196,543, filed on Apr. 11, 2000, and provisional application No. 60/159,417, filed on Oct. 14, 1999.

(51) Int. Cl.[7] .................... A61K 31/401; A61K 31/496; C07D 403/06

(52) U.S. Cl. ............ 514/218; 514/253.09; 514/254.01; 514/254.05; 514/254.09; 514/422; 514/423; 540/575; 544/364; 544/371; 544/372; 544/373; 546/197; 546/208; 548/518; 548/526; 548/537

(58) Field of Search ................................. 548/537, 518, 548/526; 544/372, 364, 371, 373; 540/575; 514/218, 254.01, 423, 253.09, 254.05, 254.09, 422; 546/197, 208

(56) References Cited

U.S. PATENT DOCUMENTS 5,892,038 A    4/1999   Dolle, III et al. ........... 544/358

FOREIGN PATENT DOCUMENTS

| WO | WO 98/30576 | 7/1998 |
| WO | WO 98/33797 | 8/1998 |
| WO | WO 98/57933 | 12/1998 |
| WO | WO 00/74706 | 12/2000 |

OTHER PUBLICATIONS

Essawi et al., "Synthesis and Evaluation of 1–and 2–Substituted Fentanyl Analogues for Opioid Activity", J. Med. Chem. 26 (3): 348–352(1983).

*Primary Examiner*—Deepak Rao
(74) *Attorney, Agent, or Firm*—Ropes & Gray

(57) ABSTRACT

The present invention makes available methods and reagents for inhibiting aberrant growth states resulting from hedgehog gain-of-function, ptc loss-of-function or smoothened gain-of-function comprising contacting the cell with a hedgehog antagonist, such as a small molecule, in a sufficient amount to aberrant growth state, e.g., to agonize a normal ptc pathway or antagonize smoothened or hedgehog activity.

43 Claims, 48 Drawing Sheets

Shh TREATED E17.5 MOUSE SKIN PUNCH

MEDIATORS OF HEDGEHOG SIGNALING PATHWAYS, COMPOSITIONS AND USES RELATED THERETO

This application is based on U.S. Provisional No. 60/159,417, filed Oct. 14, 1999, and No. 60/196,543, filed Apr. 11, 2000. This application further incorporates by reference U.S. Provisional Application No. 60/240,536, filed Oct. 13, 2000 to Dudek, et al., and U.S. Provisional No. 60/211,919, filed Jun. 16, 2000.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

Members of the Hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

The first hedgehog gene was identified by a genetic screen in the fruitfly *Drosophila melanogaster* (Nüsslein-Volhard, C. and Wieschaus, E. (1980) *Nature* 287, 795–801). This screen identified a number of mutations affecting embryonic and larval development. In 1992 and 1993, the molecular nature of the Drosophila hedgehog (hh) gene was reported (C F., Lee et al. (1992) *Cell* 71, 33–50), and since then, several hedgehog homologues have been isolated from various vertebrate species. While only one hedgehog gene has been found in Drosophila and other invertebrates, multiple Hedgehog genes are present in vertebrates.

The vertebrate family of hedgehog genes includes at least four members, e.g., paralogs of the single drosophila hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33–50; Tabata, T. et al. (1992) *Genes Dev.* 2635–2645; Chang, D. E. et al. (1994) *Development* 120:3339–3353), Hedgehog precursor proteins undergo an internal autoproteolytic cleavage which depends on conserved sequences in the C-terminal portion (Lee et al. (1994) *Science* 266:1528–1537; Porter et al. (1995) *Nature* 374:363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294–2303; Porter et al. (1995) supra; Ekker, S. C. et al. (1995) *Curr. Biol.* 5:944–955; Lai, C. J. et al. (1995) *Development* 121:2349–2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Mart', E. et al. (1995) *Development* 121:2537–2547; Roelink, H. et al. (1995) *Cell* 81:445–455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21–34). Biochemical studies have shown that the autoproteolytic cleavage of the HH precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities in Drosophila and vertebrates (Porter et al. (1995) supra; Ekker et al. (1995) supra: Lai et al. (1995) supra; Roelink, H. et al. (1995) *Cell* 81:445–455; Porter et al. (1996) supra; Fietz, M. J. et al. (1995) *Curr. Biol.* 5:643–651; Fan, C.-M. et al. (1995) *Cell* 81:457–465; Mart', E., et al. (1995) *Nature* 375:322–325; Lopez-Martinez et al. (1995) *Curr. Biol* 5:791–795; Ekker, S. C. et al. (1995) *Development* 121:2337–2347; Forbes, A. J. et al. (1996) *Development* 122:1125–1135).

HH has been implicated in short- and long-range patterning processes at various sites during Drosophila development. In the establishment of segment polarity in early embryos, it has short-range effects which appear to be directly mediated, while in the patterning of the imaginal discs, it induces long range effects via the induction of secondary signals.

In vertebrates, several hedgehog genes have been cloned in the past few years. Of these genes, Shh has received most of the experimental attention, as it is expressed in different organizing centers which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) Cell 75:1417–1430), the rat (Roelink, H. et al. (1994) Cell 76:761–775) and the chick (Riddle, R. D. et al. (1993) Cell 75:1401–1416), and the shield in the zebrafish (Ekker et al. (1995) supra; Krauss, S. et al. (1993) Cell 75:1431–1444). In chick embyros, the Shh expression pattern in the node develops a left-right asymmetry, which appears to be responsible for the left-right situs of the heart (Levin, M. et al. (1995) Cell 82:803–814).

In the CNS, Shh from the notochord and the floorplate appears to induce ventral cell fates. When ectopically expressed, Shh leads to a ventralization of large regions of the mid- and hindbrain in mouse (Echelard et al. (1993) supra; Goodrich, L. V. et al. (1996) Genes Dev. 10:301–312), Xenopus (Roelink, H. et al. (1994) supra; Ruiz i Altaba, A. et al. (1995) Mol. Cell. Neurosci. 6:106–121), and zebrafish (Ekker et al. (1995) supra; Krauss et al. (1993) supra; Hammerschmidt, M., et al. (1996) Genes Dev. 10:647–658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Mart' et al. (1995) supra; Tanabe, Y. et al. (1995) Curr. Biol. 5:651–658). Moreover, antibody blocking suggests that Shh produced by the notochord is required for notochord-mediated induction of motor neuron fates (Mart' et al. (1995) supra). Thus, high concentration of Shh on the surface of Shh-producing midline cells appears to account for the contact-mediated induction of Doorplate observed in vitro (Placzek, M. et al. (1993) Development 117:205–218), and the midline positioning of the Doorplate immediately above the notochord in vivo. Lower concentrations of Shh released from the notochord and the floorplate presumably induce motor neurons at more distant ventrolateral regions in a process that has been shown to be contact-independent in vitro (Yamada, T. et al. (1993) Cell 73:673–686). In explants taken at midbrain and forebrain levels, Shh also induces the appropriate ventrolateral neuronal cell types, dopaminergic (Heynes, M. et al. (1995) Neuron 15:35–44; Wang, M. Z. et al. (1995) Nature Med. 1:1184–1188) and cholinergic (Ericson, J. et al. (1995) Cell 81:747–756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) Cell 79, 1175–1186).

Shh also induces myotomal gene expression (Hammerschmidt et al. (1996) supra; Johnson, R. L. et al. (1994) Cell 79:1165–1173; Münsterberg, A. E. et al. (1995) Genes Dev. 9:2911–2922; Weinberg, E. S. et al. (1996) Development 122:271–280), although recent experiments indicate that members of the WNT family, vertebrate homologues of Drosophila wingless, are required in concert (M ünsterberg et al. (1995) supra). Puzzlingly, myotomal induction in chicks requires higher Shh concentrations than the induction of sclerotomal markers (Münsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) Nature 291:72–73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100–150 μm). Similar to the interaction of HH and DPP in the Drosophila imaginal discs, Shh in the vertebrate limb bud activates the expression of Bmp2 (Francis, P. H. et al. (1994) Development 120:209–218), a dpp. homologue. However, unlike DPP in Drosophila, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) Cell 79:993–1003; Niswander, L. et al. (1994) Nature 371:609–612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) Development 121:3163–3174). Furthermore, Shh and Bmp2, 4, or 6 show a striking correlation in their expression in epithelial and mesenchymal cells of the stomach, the urogenital system, the lung, the tooth buds and the hair follicles (Bitgood, M. J. and McMahon, A. P. (1995) Dev. Biol. 172:126–138). Further, Ihh, one of the two other mouse Hedgehog genes, is expressed adjacent to Bmp expressing cells in the gut and developing cartilage (Bitgood and McMahon (1995) supra).

Recent evidence suggests a model in which Ihh plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of Gli and Patched (Ptc), conserved transcriptional targets of Hedgehog signals (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Patched was originally identified in Drosophila as a segment polarity gene, one of a group of developmental genes that affect cell differentiation within the individual segments that occur in a homologous series along the anterior-posterior axis of the embryo. See Hooper, J. E. et al. (1989) *Cell* 59:751; and Nakano, Y. et al. (1989) *Nature* 341:508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) *Cell* 80:517; and Perrimon, N. (1996) *Cell* 86:513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, supra; Nakano, supra; Johnson, R. L. et al. (1996) *Science* 272:1668; and Hahn, H. et al. (1996) *Cell* 85:841. The biochemical role of patched in the hedgehog signaling pathway is unclear. Direct interaction with the hedgehog protein has, however, been reported (Chen, Y. et al. (1996) *Cell* 87:553), and patched may participate in a hedgehog receptor complex along with another transmembrane protein encoded by the smoothened gene. See Perrimon, supra; and Chen, supra.

The human homologue of patched was recently cloned and mapped to chromosome 9q22.3. See Johnson, supra; and Hahn, supra. This region has been implicated in basal cell nevus syndrome (BCNS), which is characterized by developmental abnormalities including rib and craniofacial alterations, abnormalities of the hands and feet, and spina bifida.

BCNS also predisposes to multiple tumor types, the most frequent being basal cell carcinomas (BCC) that occur in many locations on the body and appear within the first two decades of life. Most cases of BCC, however, are unrelated to the syndrome and arise sporadically in small numbers on sun-exposed sites of middle-aged or older people of northern European ancestry.

Recent studies in BCNS-related and sporadic BCC suggest that a functional loss of both alleles of patched leads to development of BCC. See Johnson, supra; Hahn, supra; and Gailani, M. R. et al. (1996) *Nature Genetics* 14:78. Single allele deletions of chromosome 9q22.3 occur frequently in both sporadic and hereditary BCC. Linkage analysis revealed that the defective inherited allele was retained and the normal allele was lost in tumors from BCNS patients.

Sporadic tumors also demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). The alterations did not occur in the corresponding germline DNA.

Most of the identified mutations resulted in premature stop codons or frame shifts. Lench, N. J., et al., *Hum. Genet.* October; 1997; 100(5–6): 497–502. Several, however, were point mutations leading to amino acid substitutions in either extracellular or cytoplasmic domains. These sites of mutation may indicate functional importance for interaction with extracellular proteins or with cytoplasmic members of the downstream signaling pathway.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

SUMMARY OF THE INVENTION

The present invention makes available methods and reagents for inhibiting activation of the hedgehog signaling pathway, e.g., to inhibit aberrant growth states resulting from phenotypes such as ptc loss-of-function, hedgehog gain-of-function, or smoothened gain-of-function, comprising contacting the cell with an agent, such as a small molecule, in a sufficient amount to agonize a normal ptc activity, antagonize a normal hedgehog activity, or antagonize smoothened activity, e.g., to reverse or control the aberrant growth state.

DETAILED DESCRIPTION OF THE INVENTION

I. Overview

Figure 1:
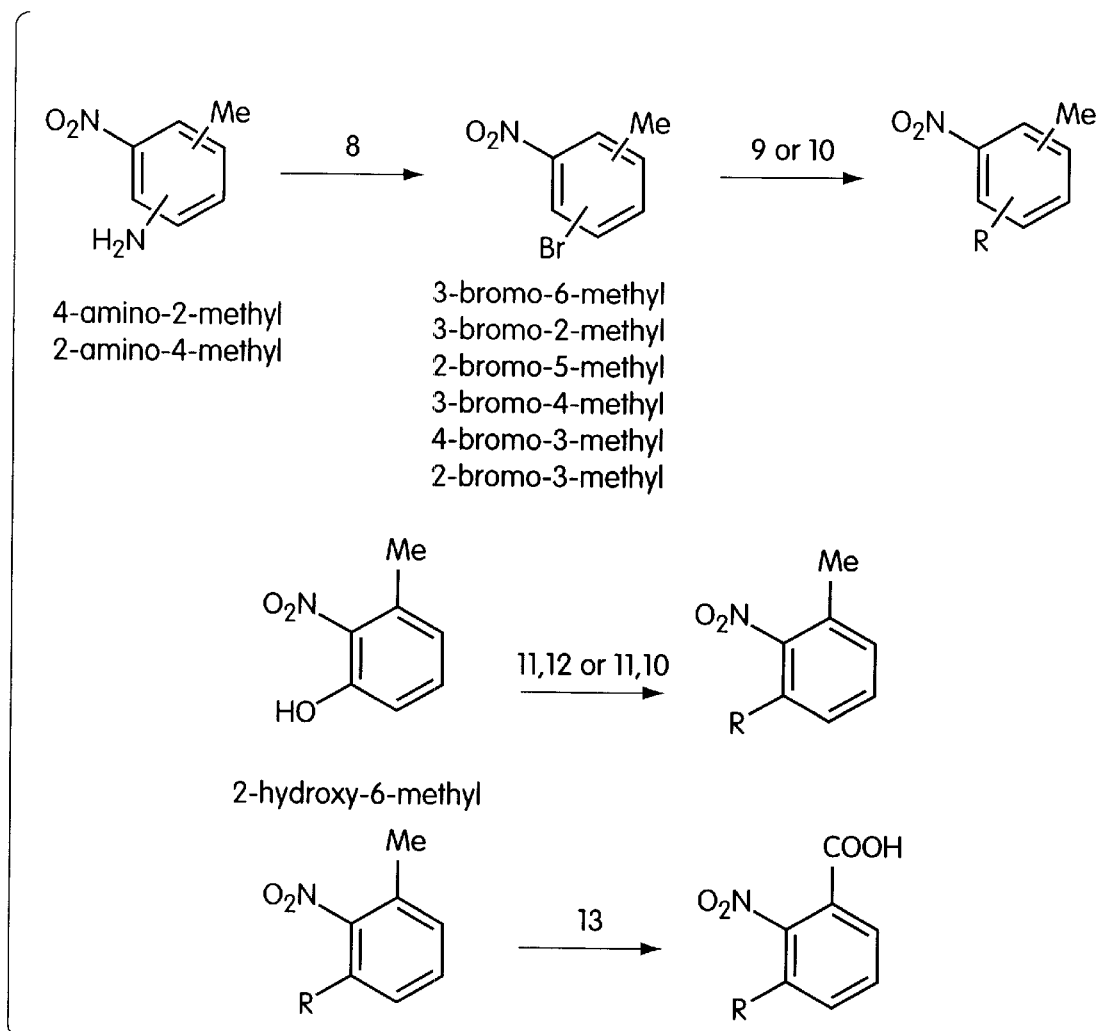
FIGS. 1–31 depict reactions useful for synthesizing compounds according to the present invention.
Figure 2:
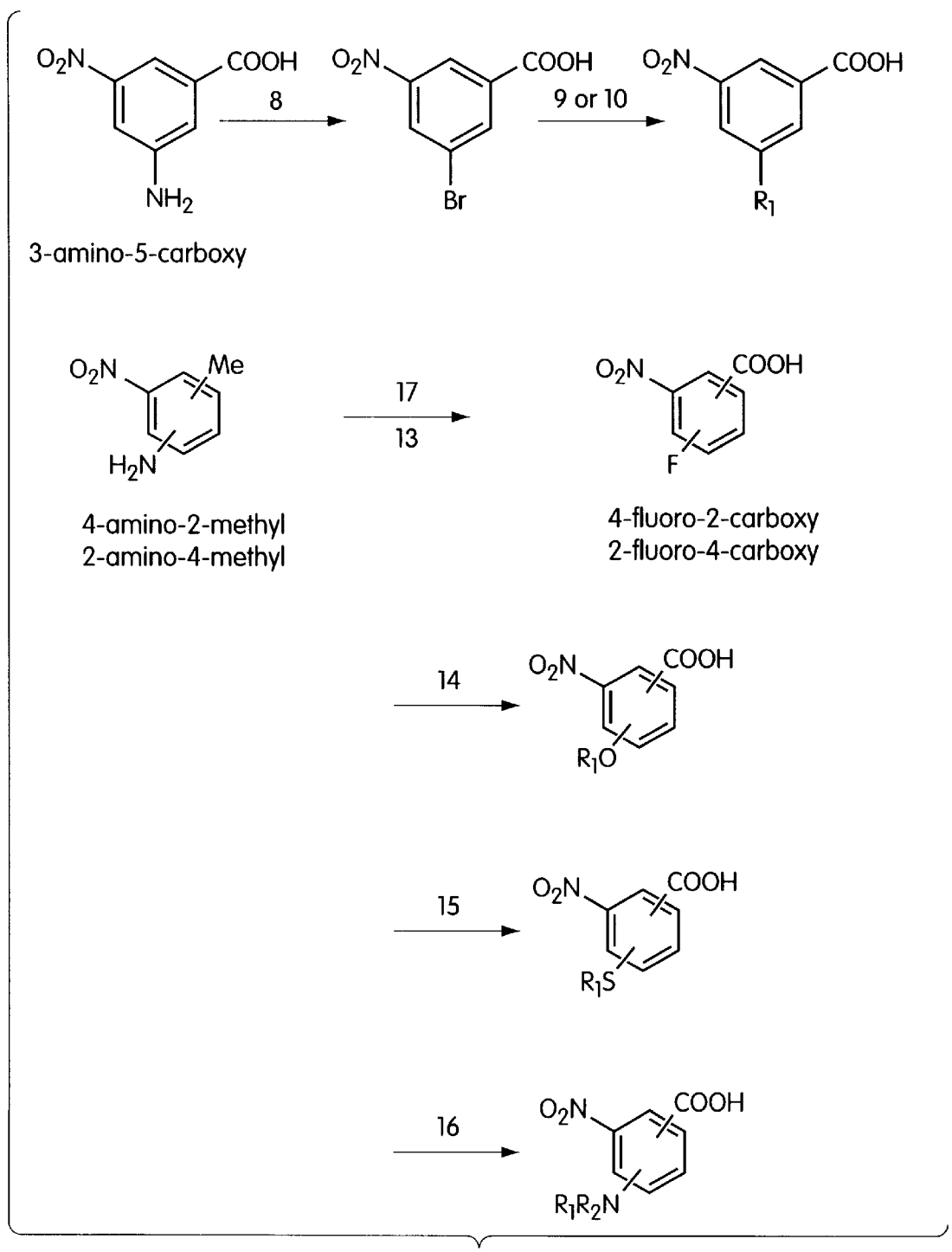
Figure 3:
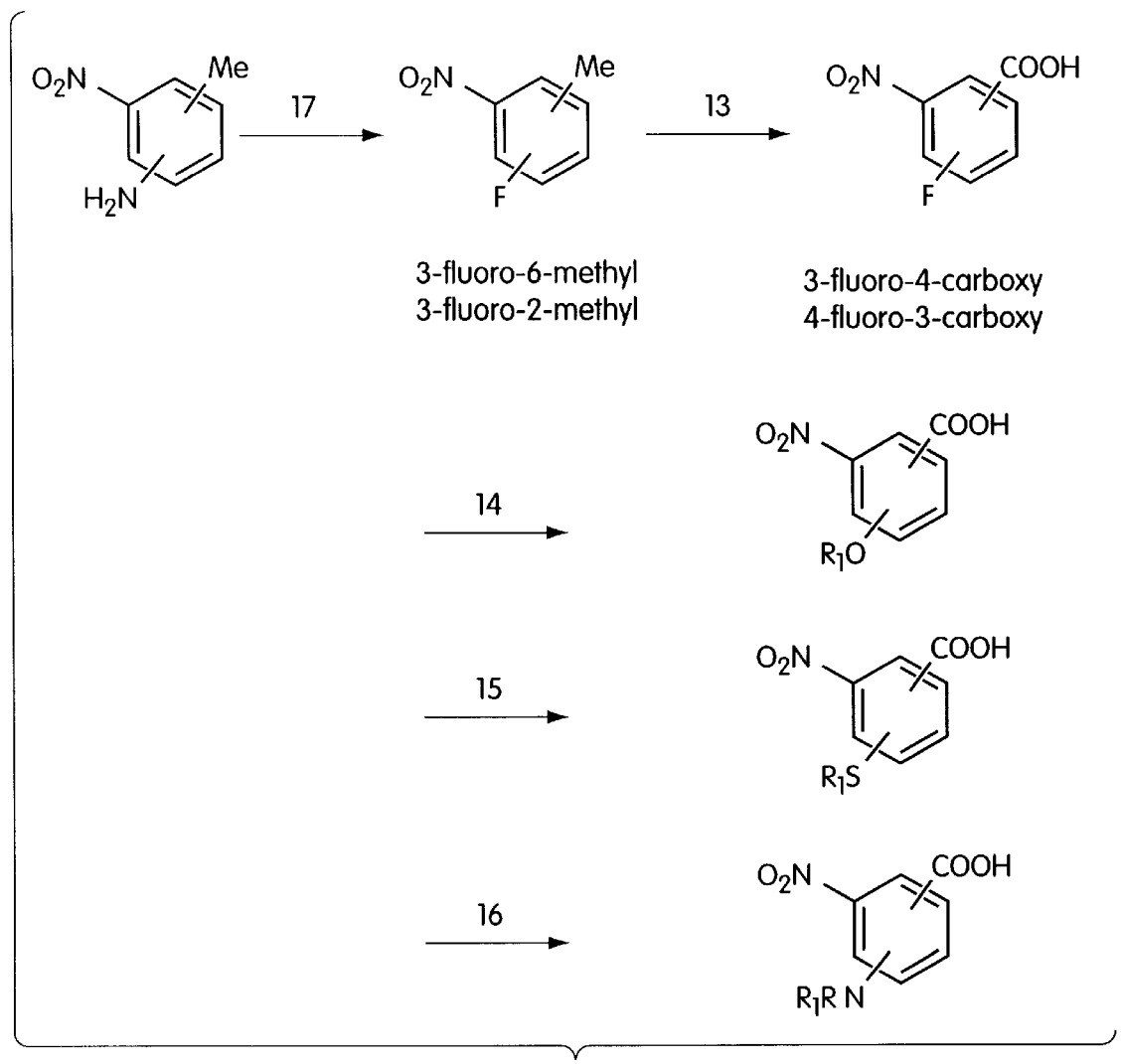
Figure 4:
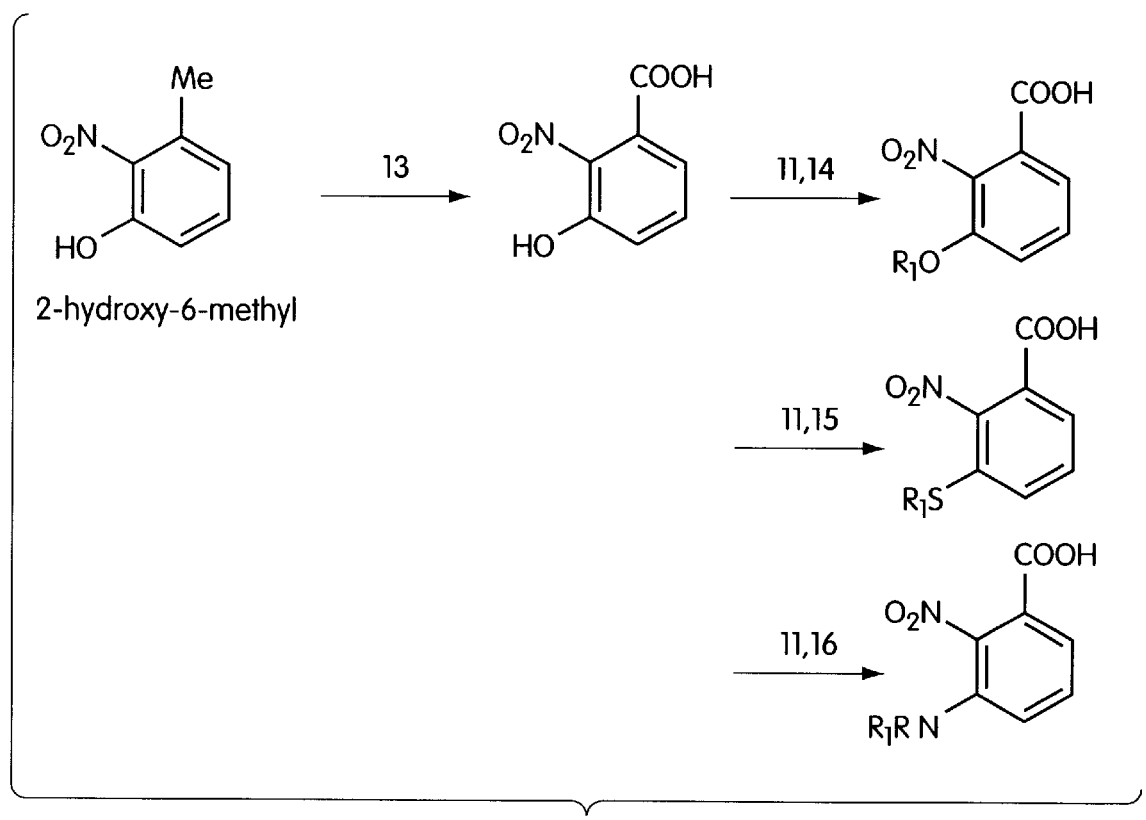
Figure 5:
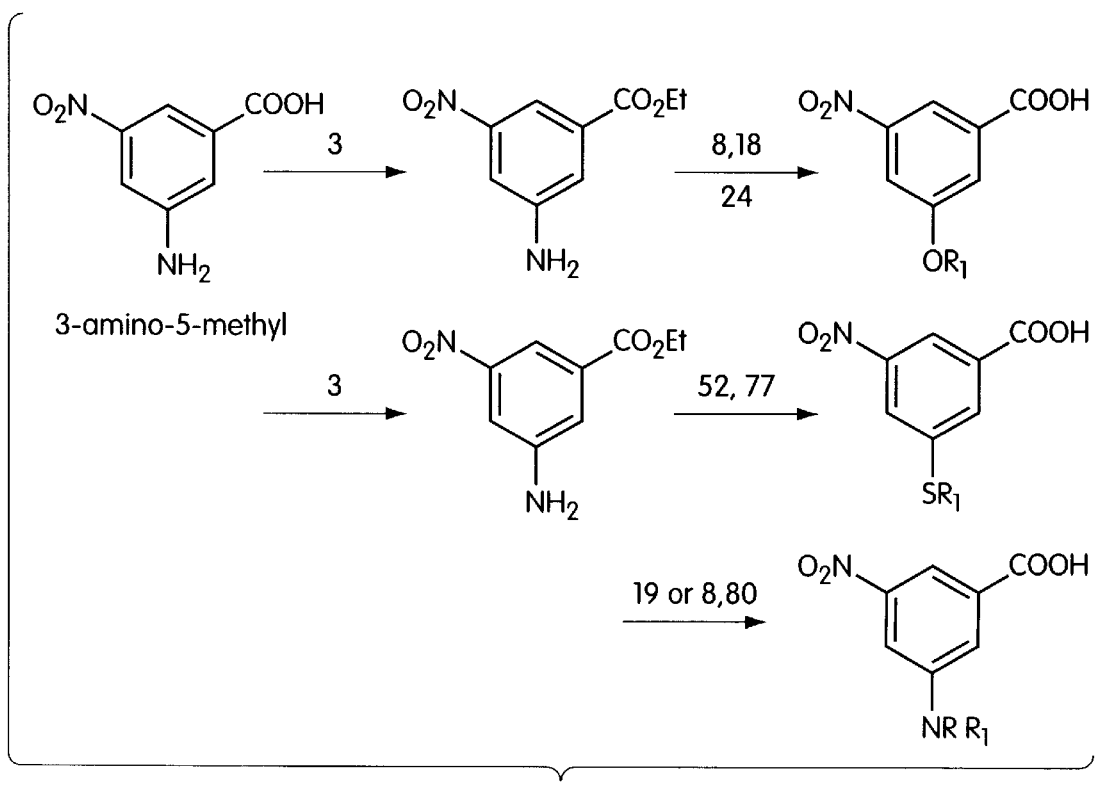
Figure 6:
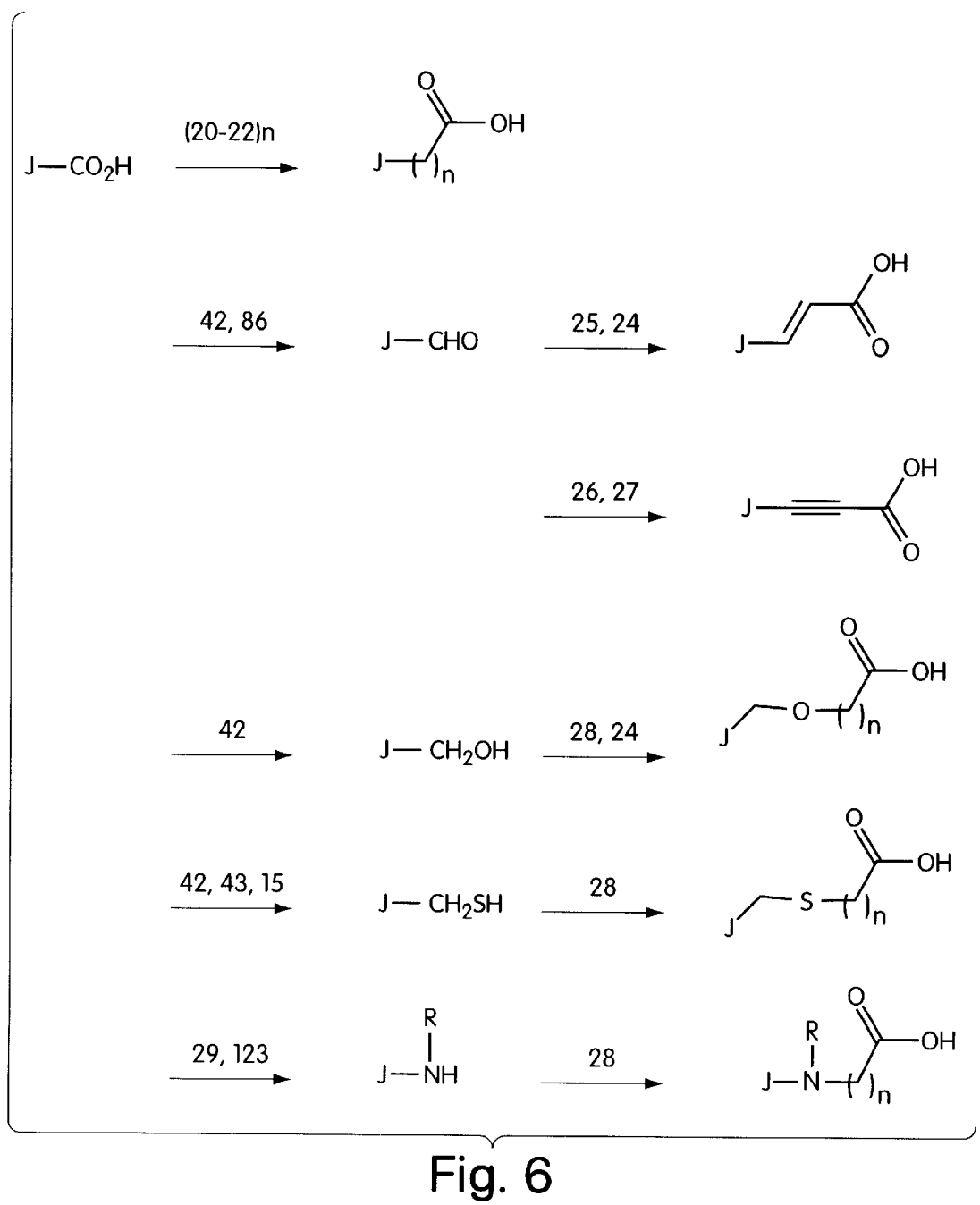
Figure 7:
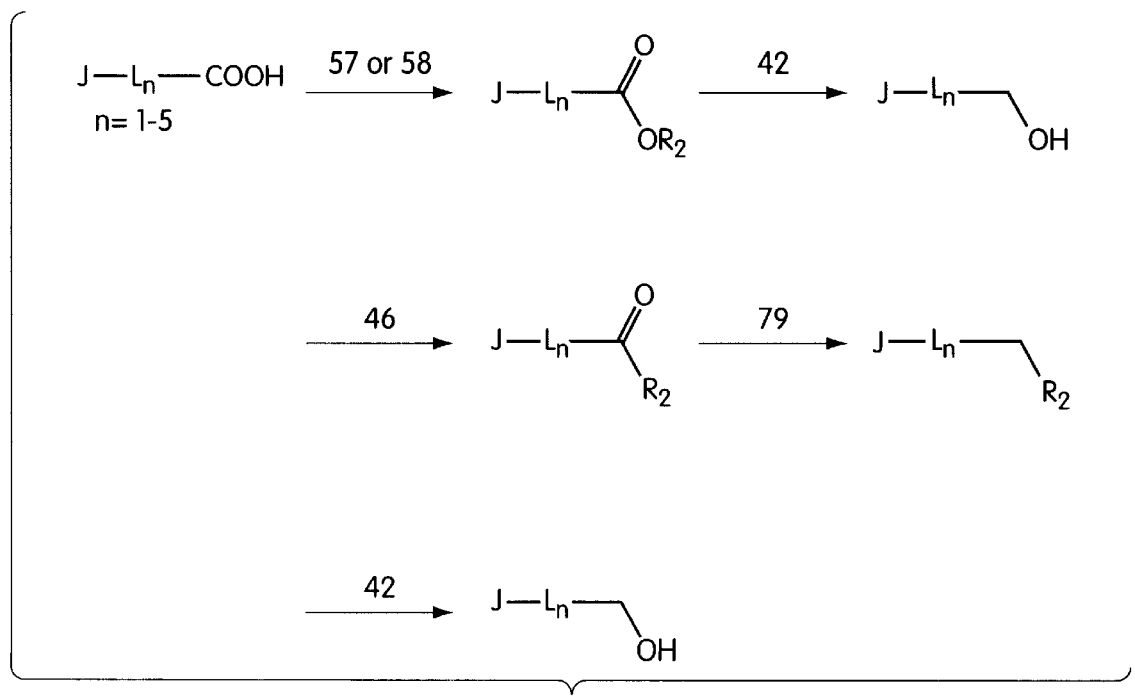
Figure 8:
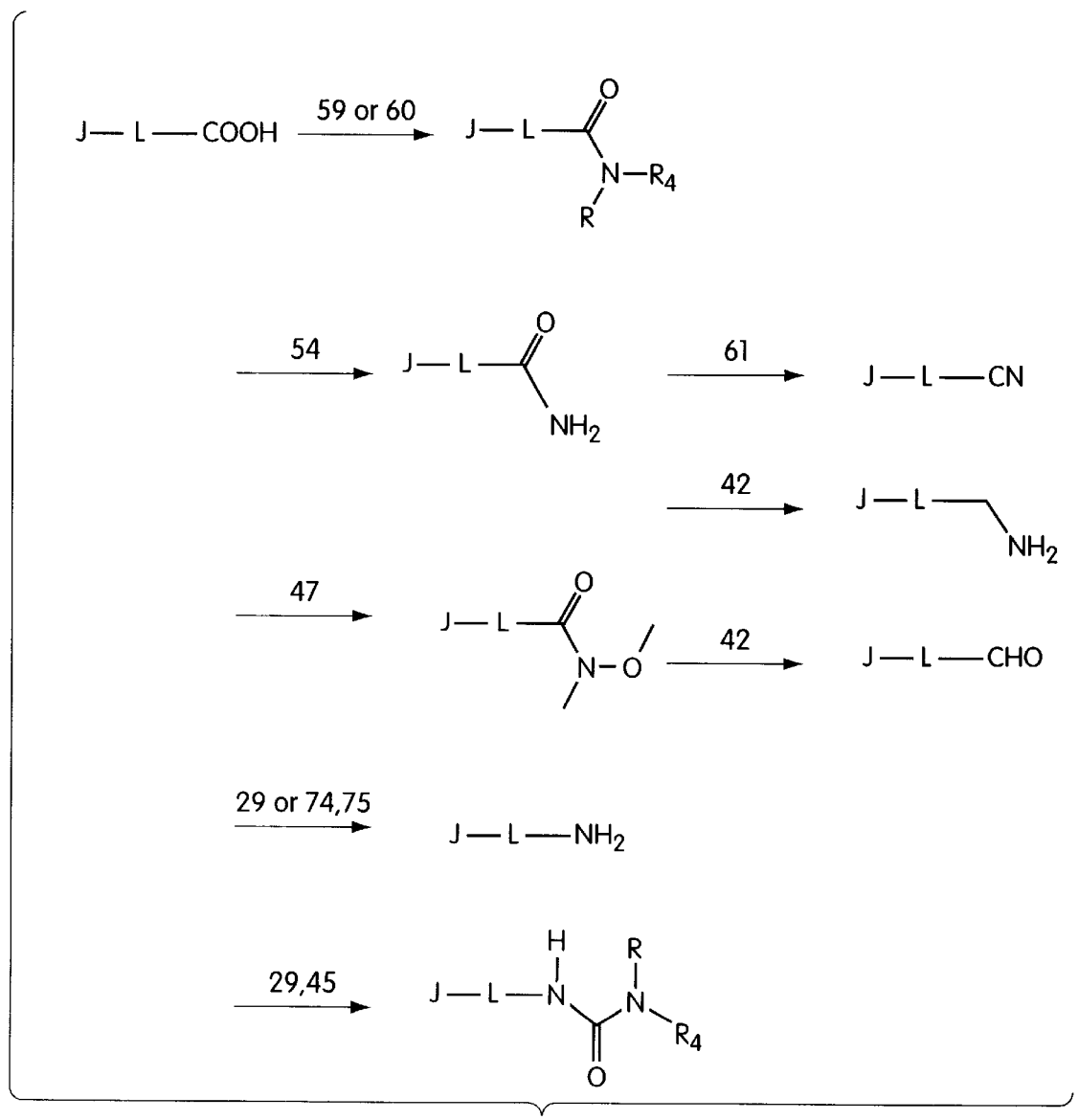
Figure 9:
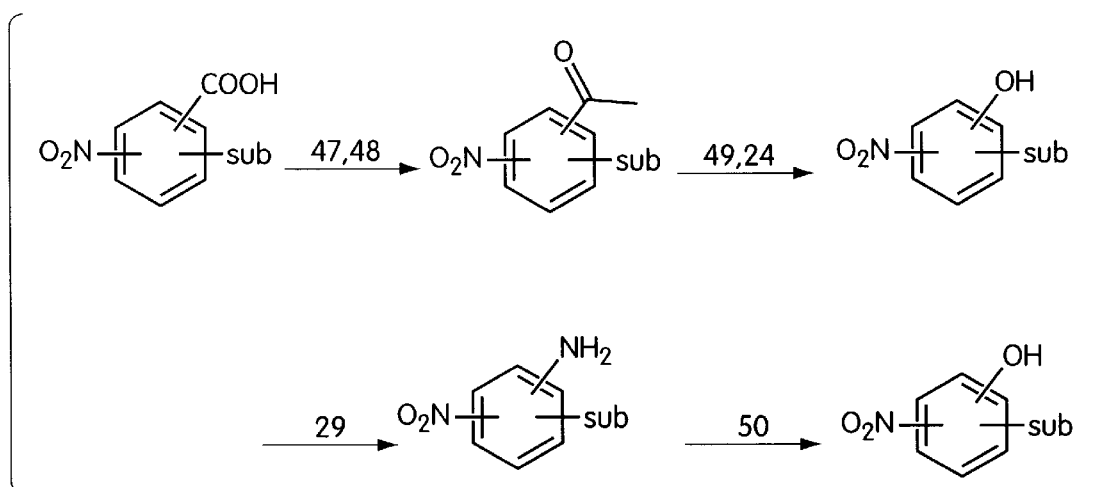
Figure 10:
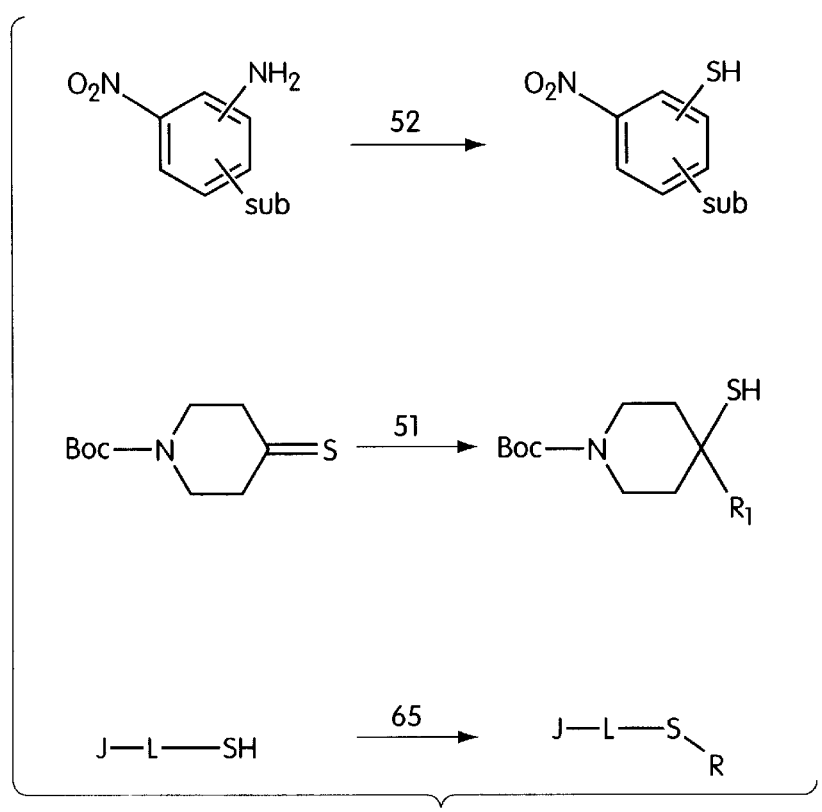
Figure 11:
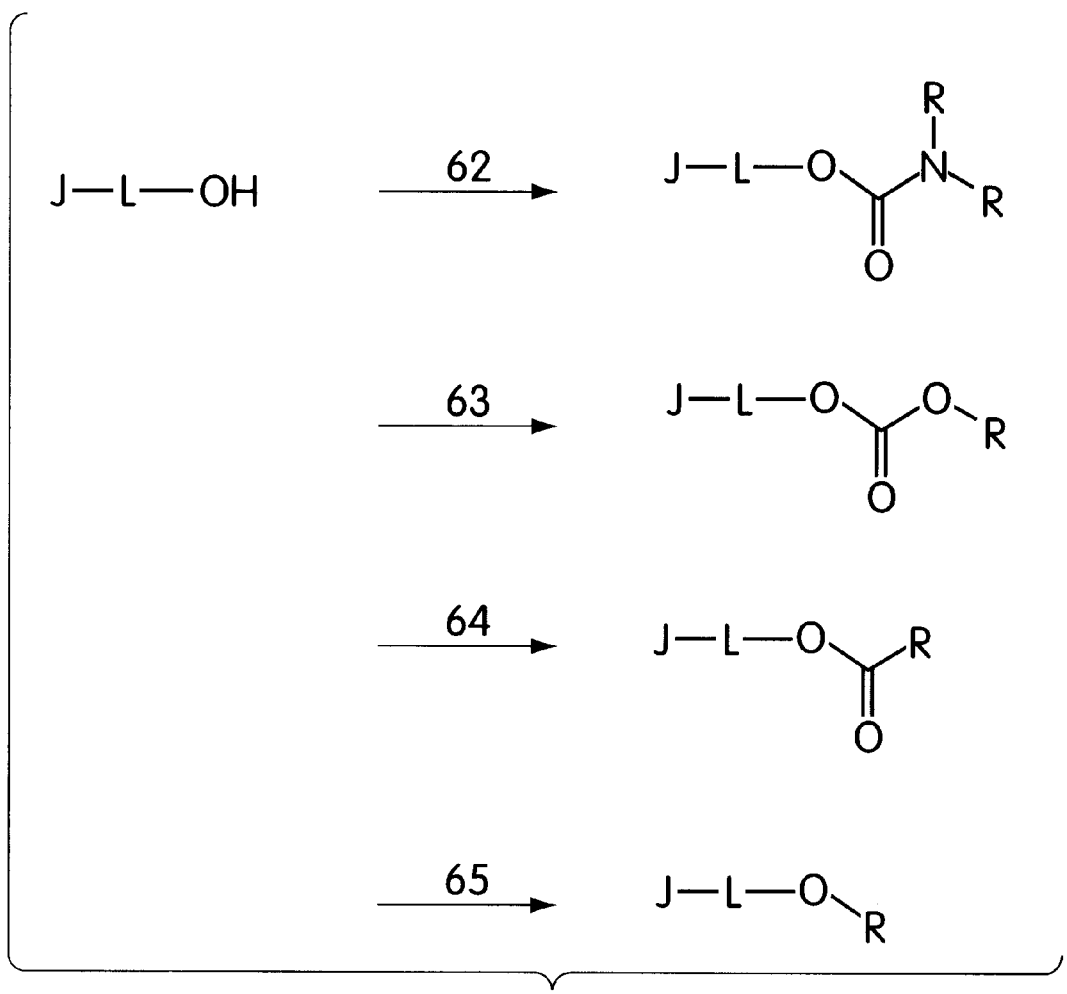
Figure 12:
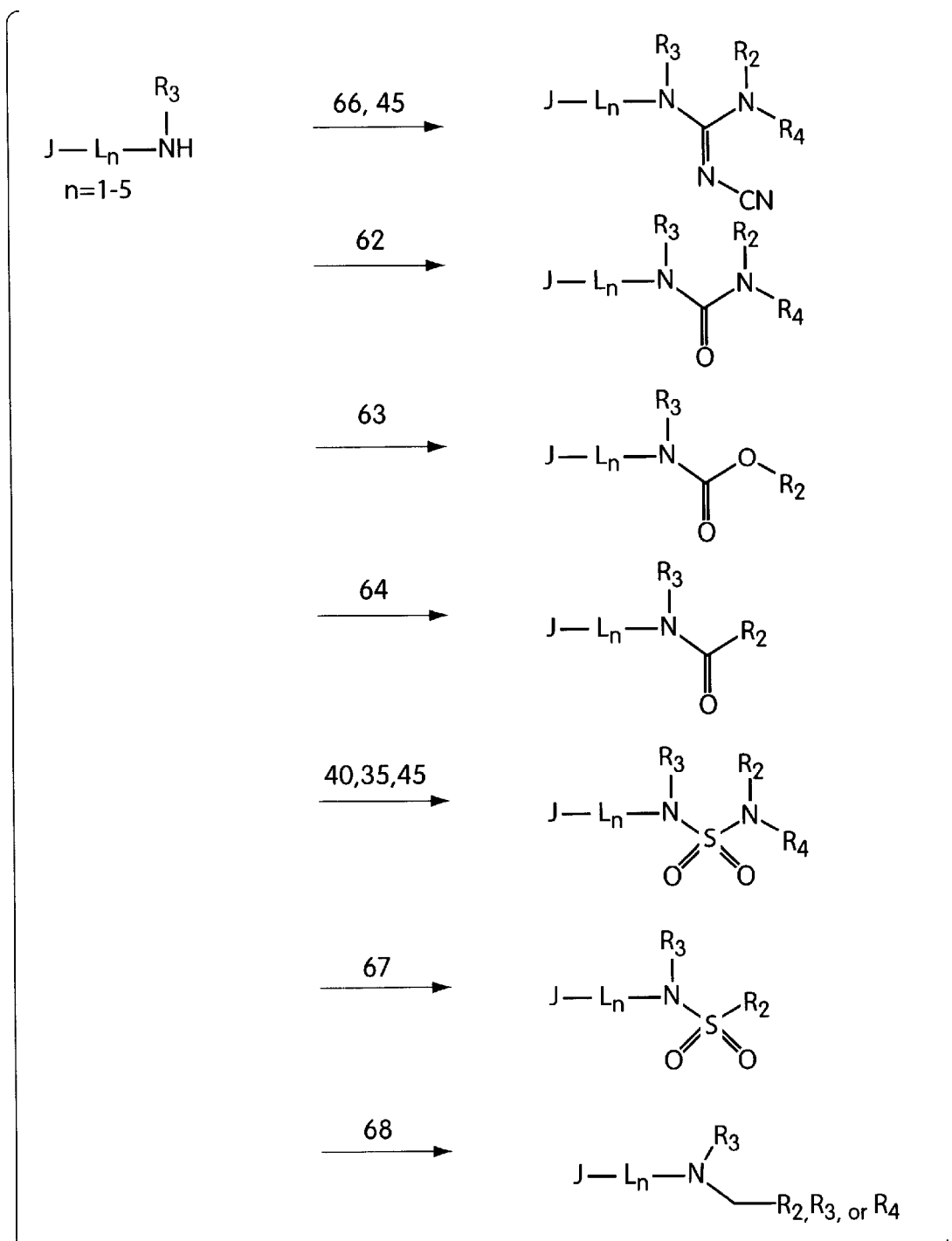
Figure 13:
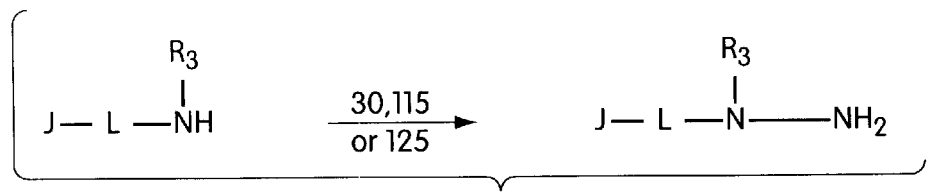
Figure 14:
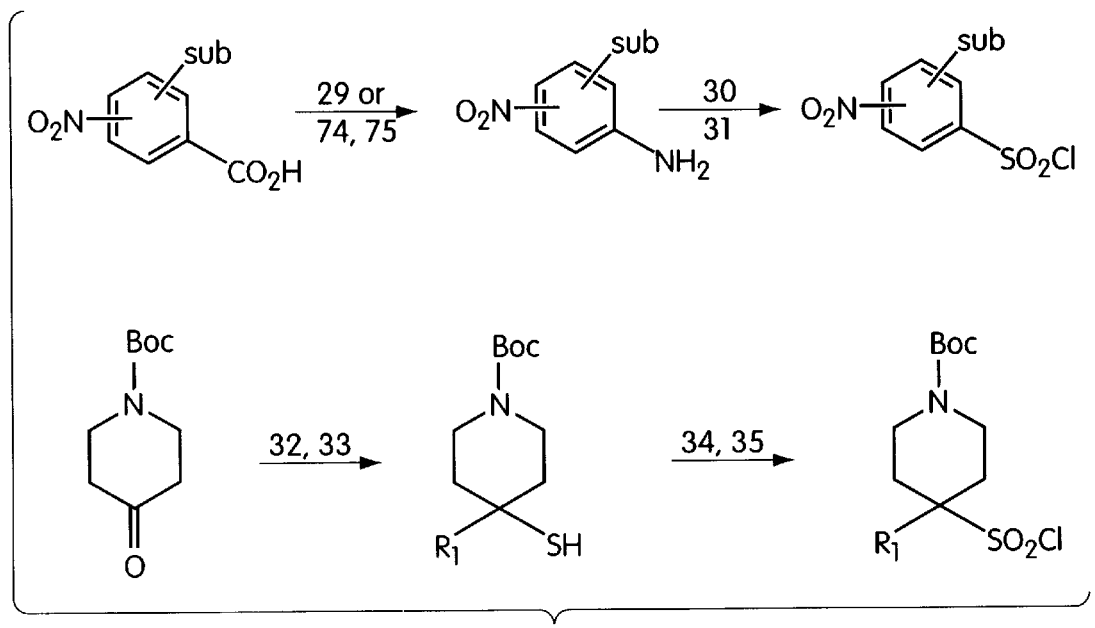
Figure 15:
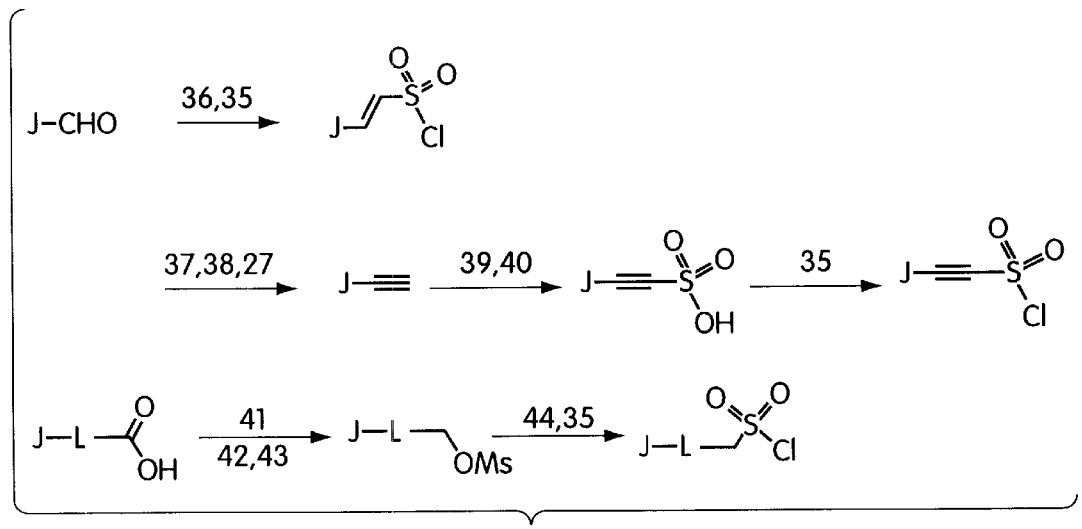
Figure 16:
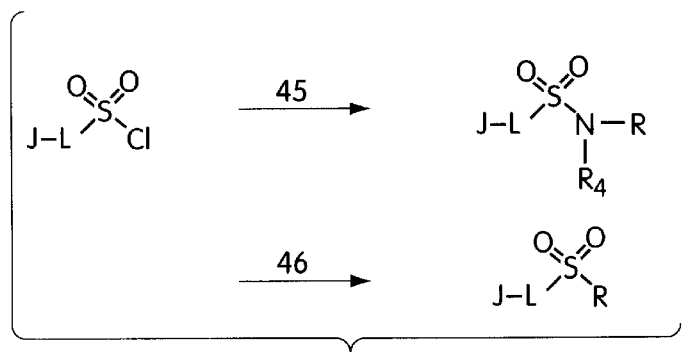
Figure 17:
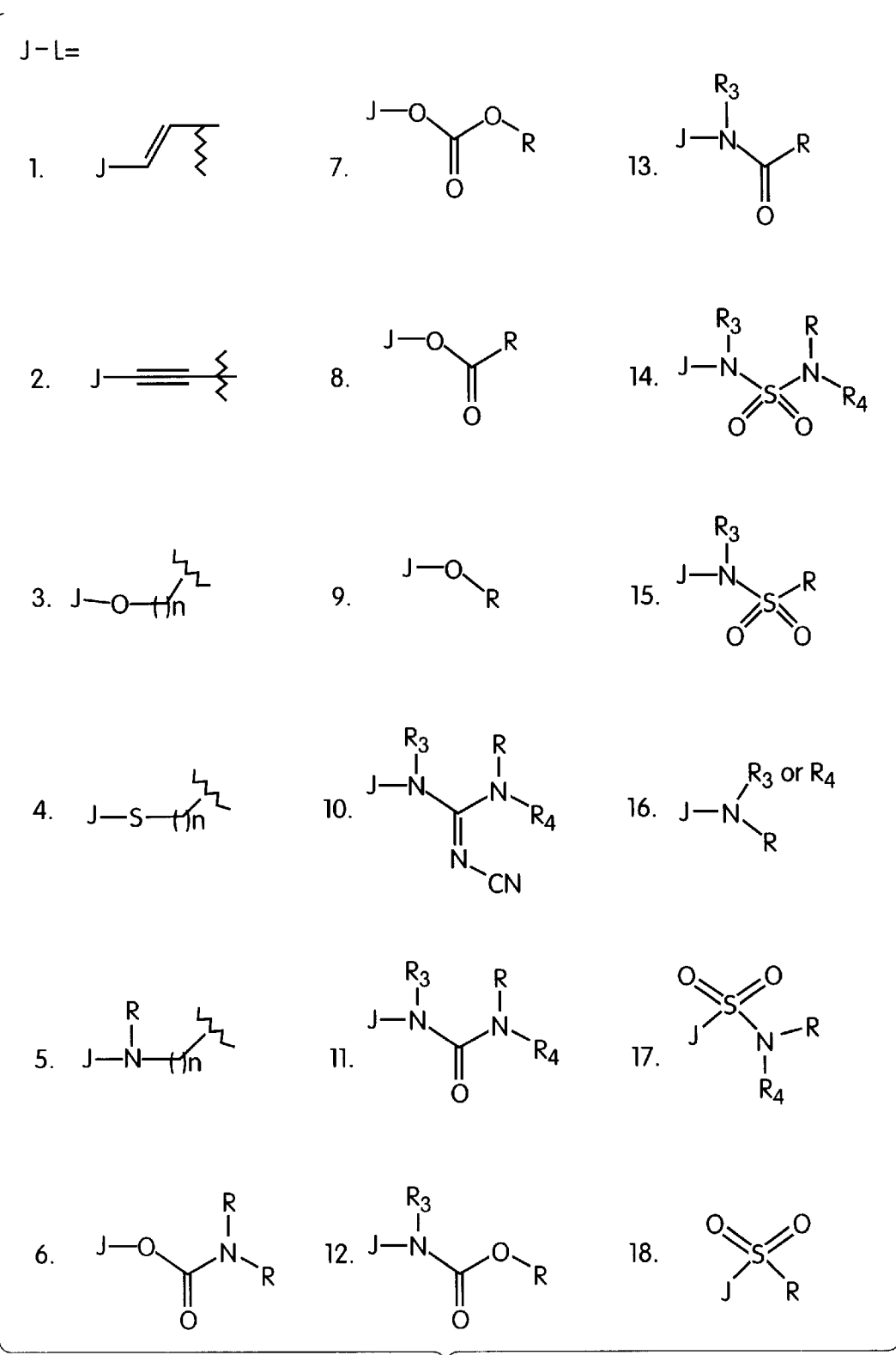
Figure 18:
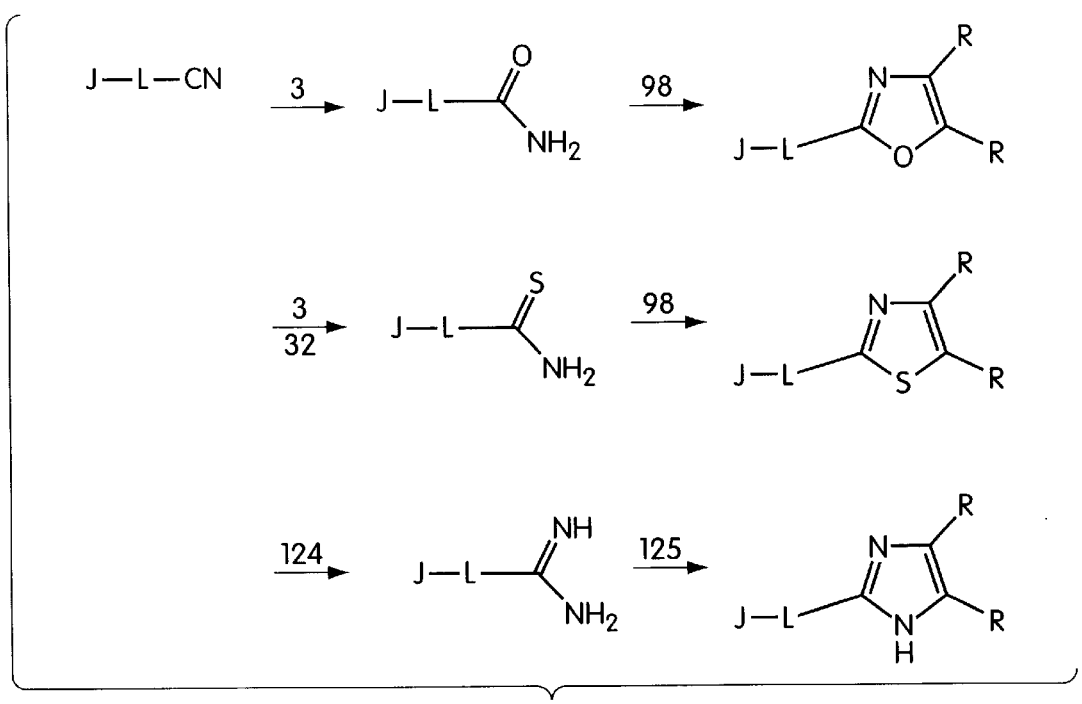
Figure 19:
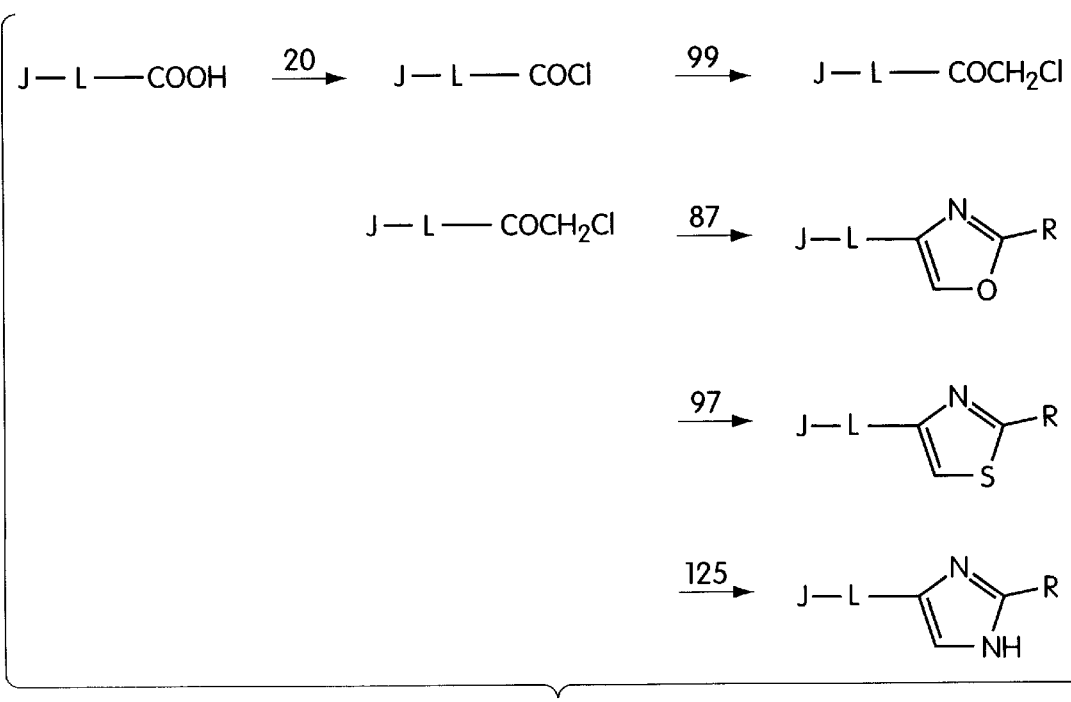
Figure 20:
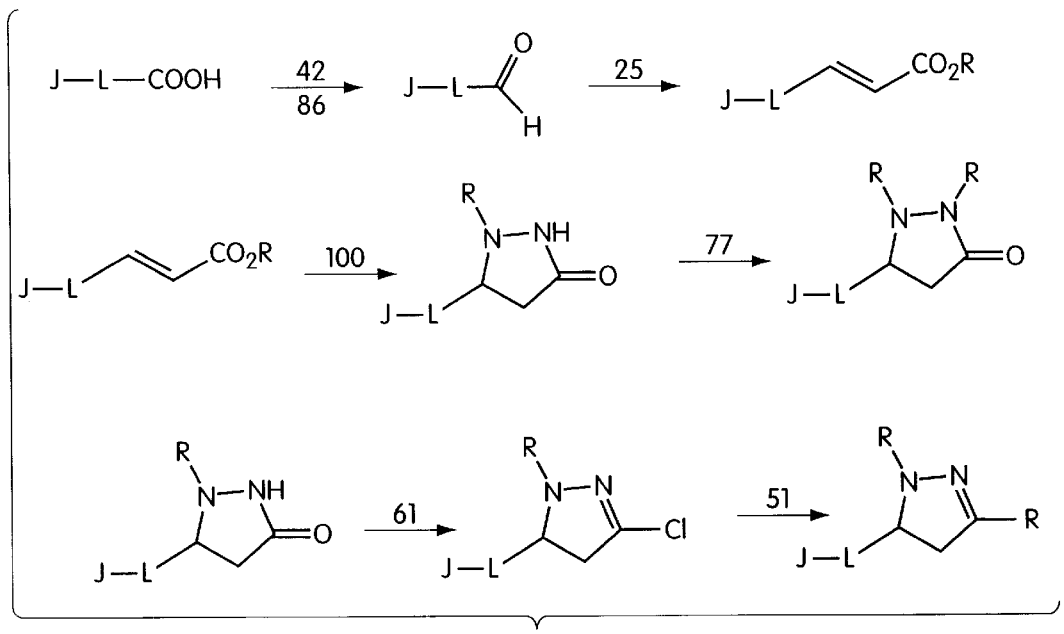
Figure 21:
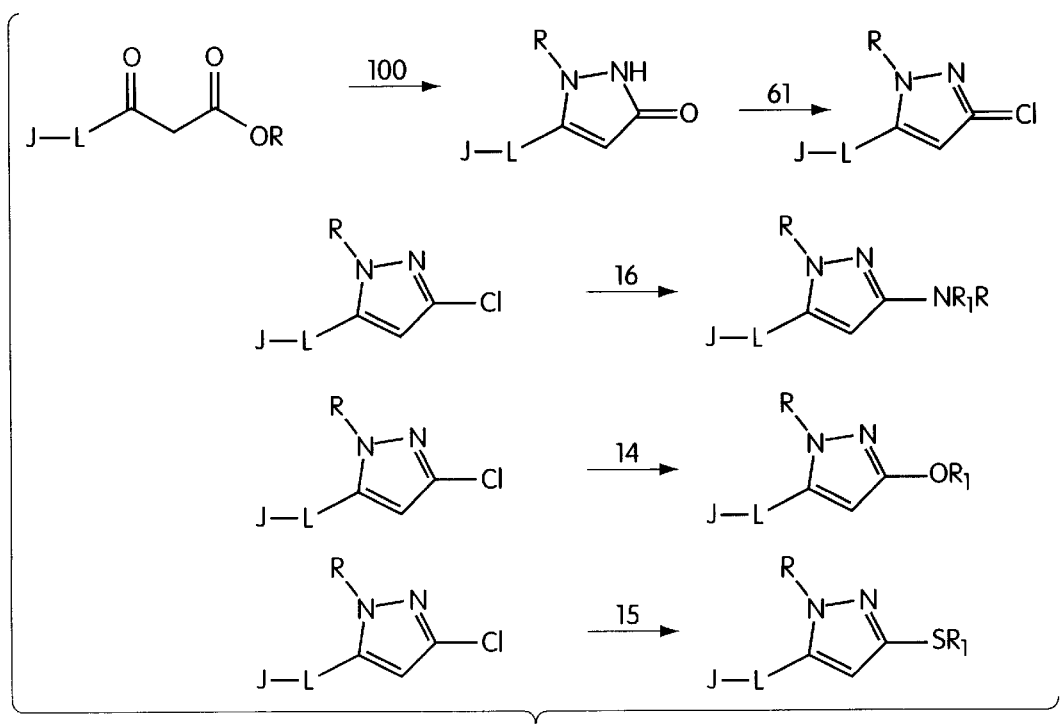
Figure 22:
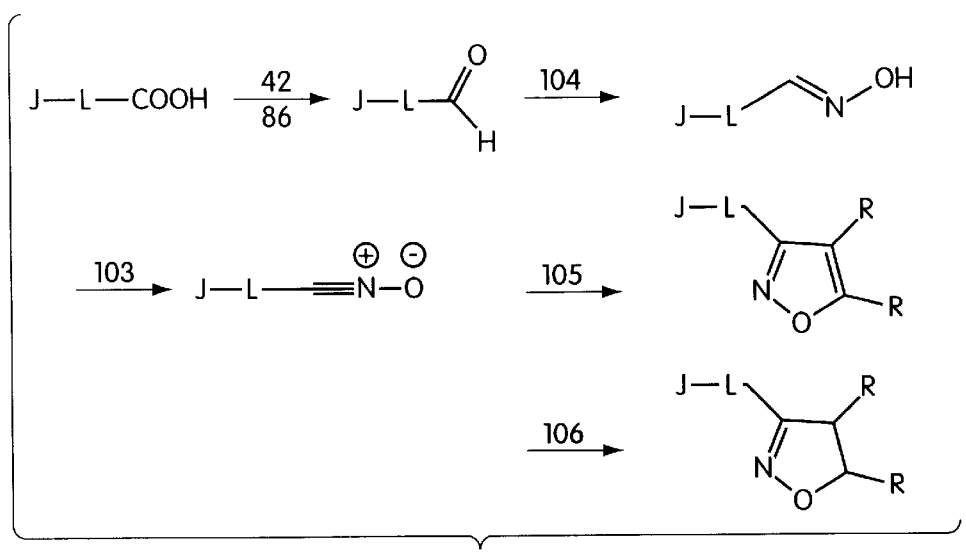
Figure 23:
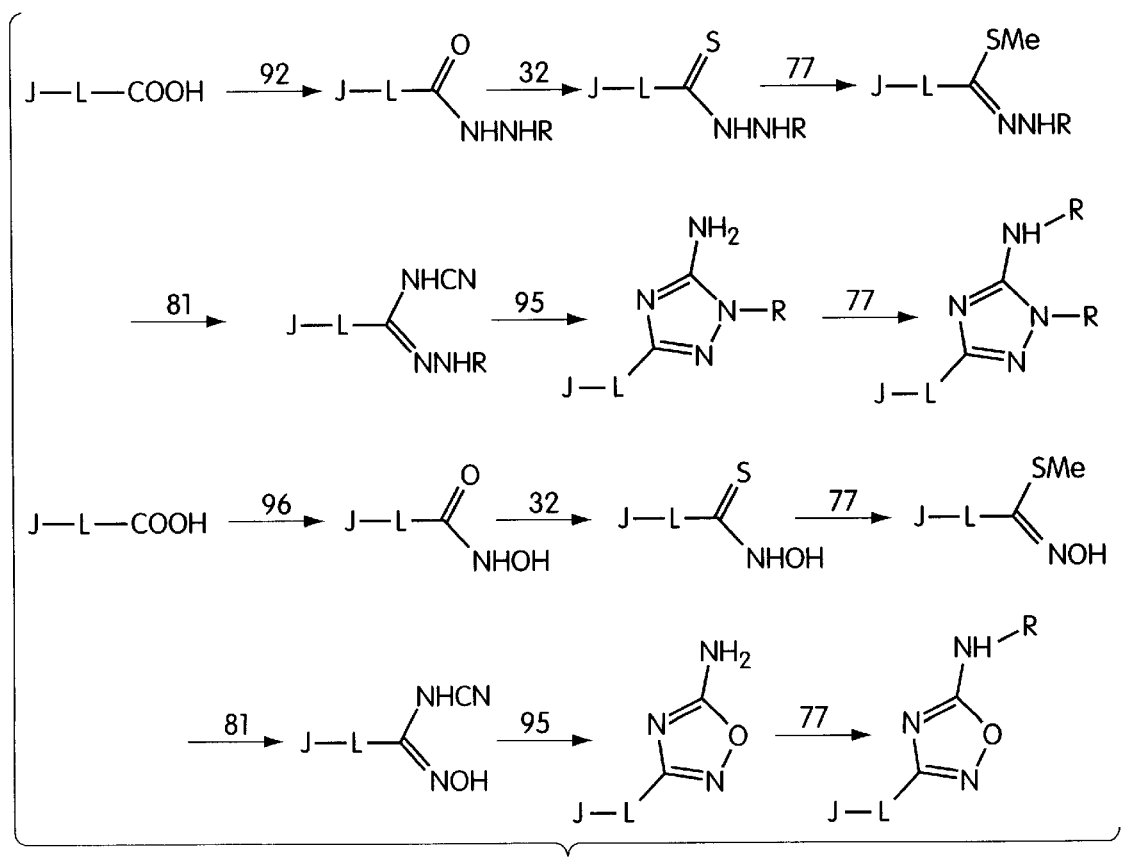
Figure 24:
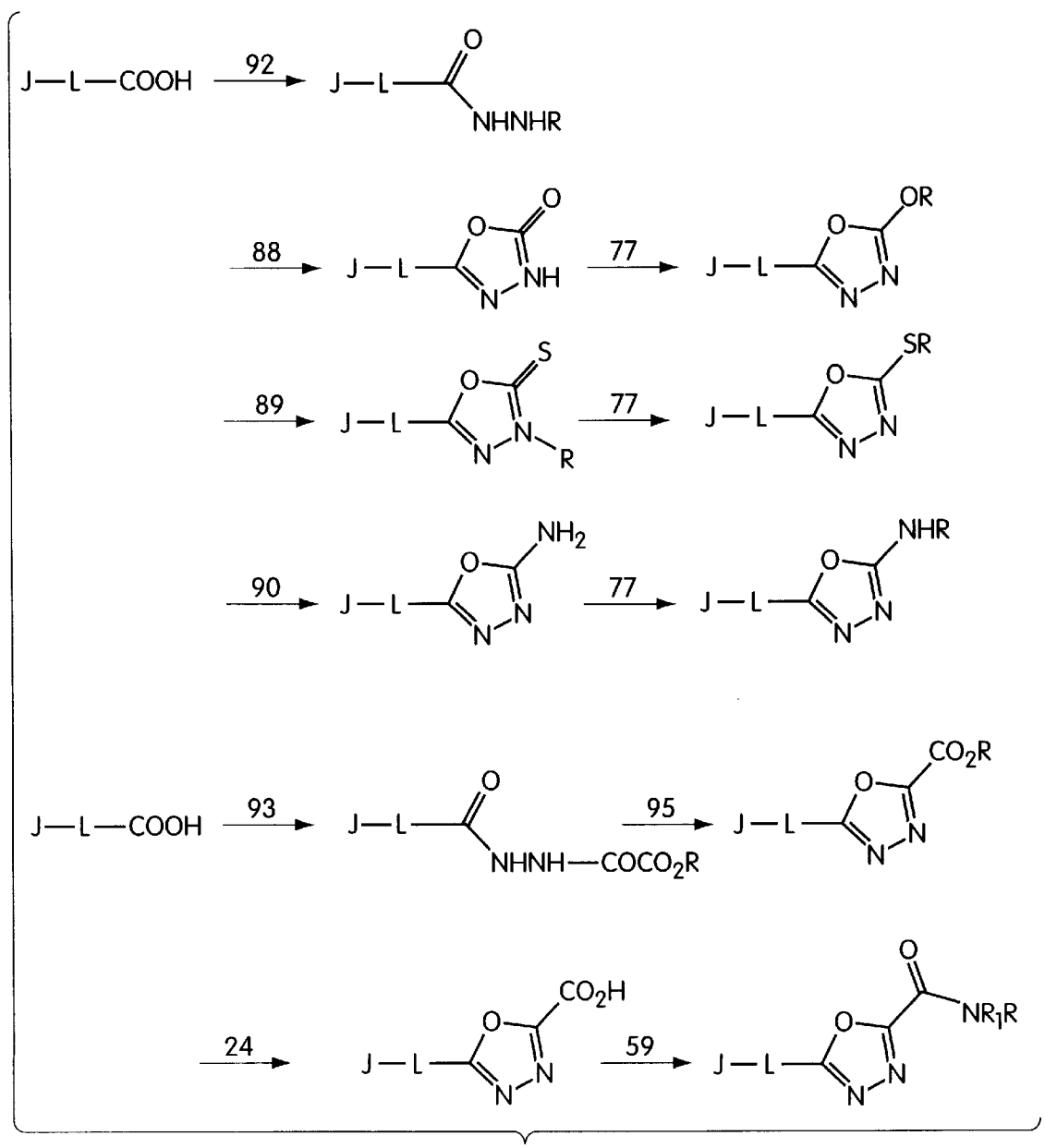
Figure 25:
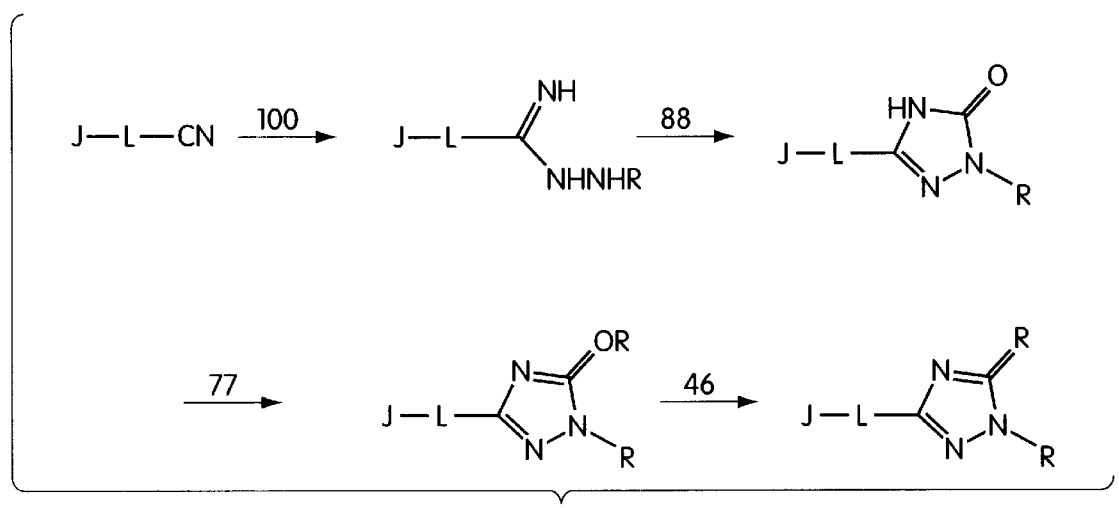
Figure 26:
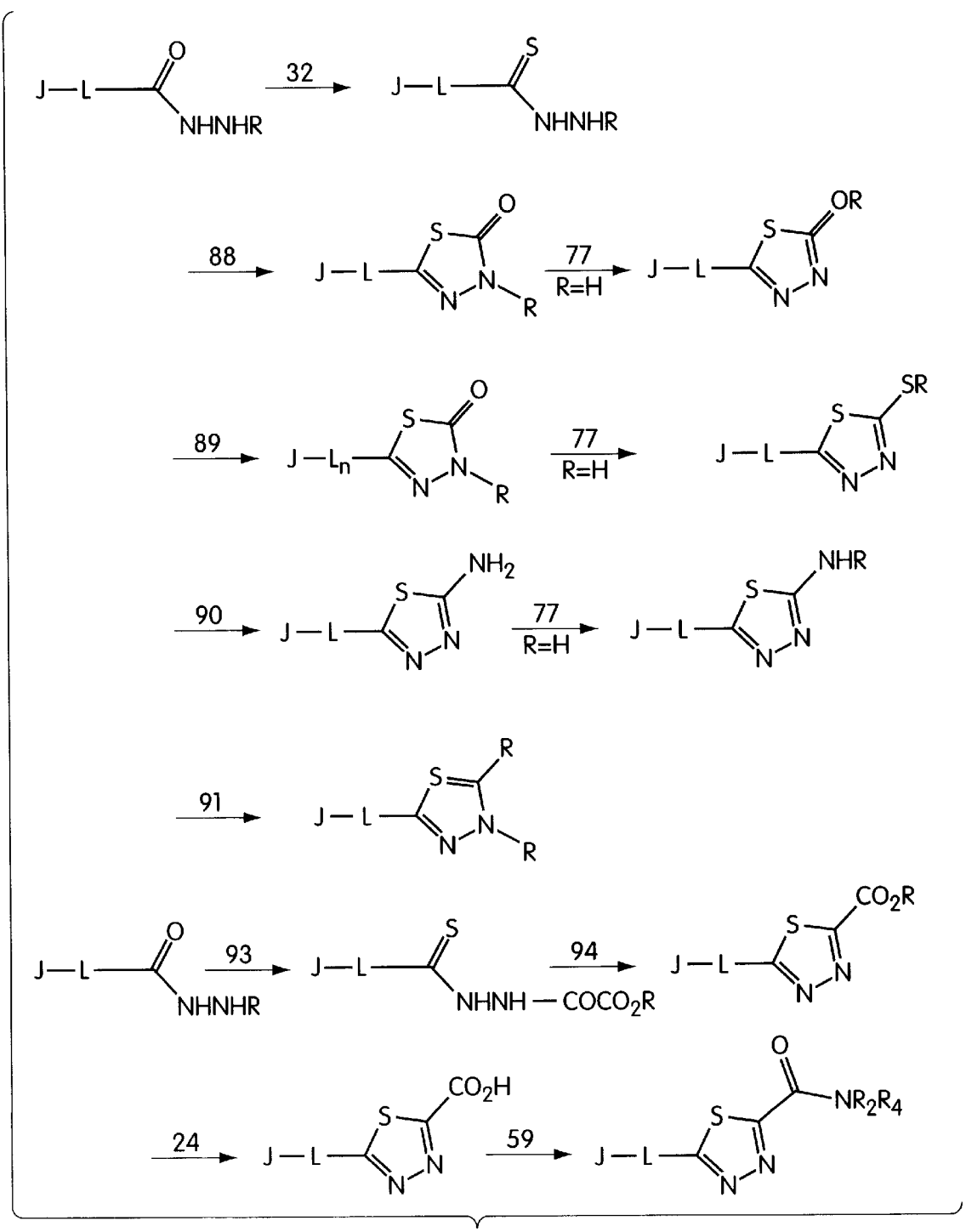
Figure 27:
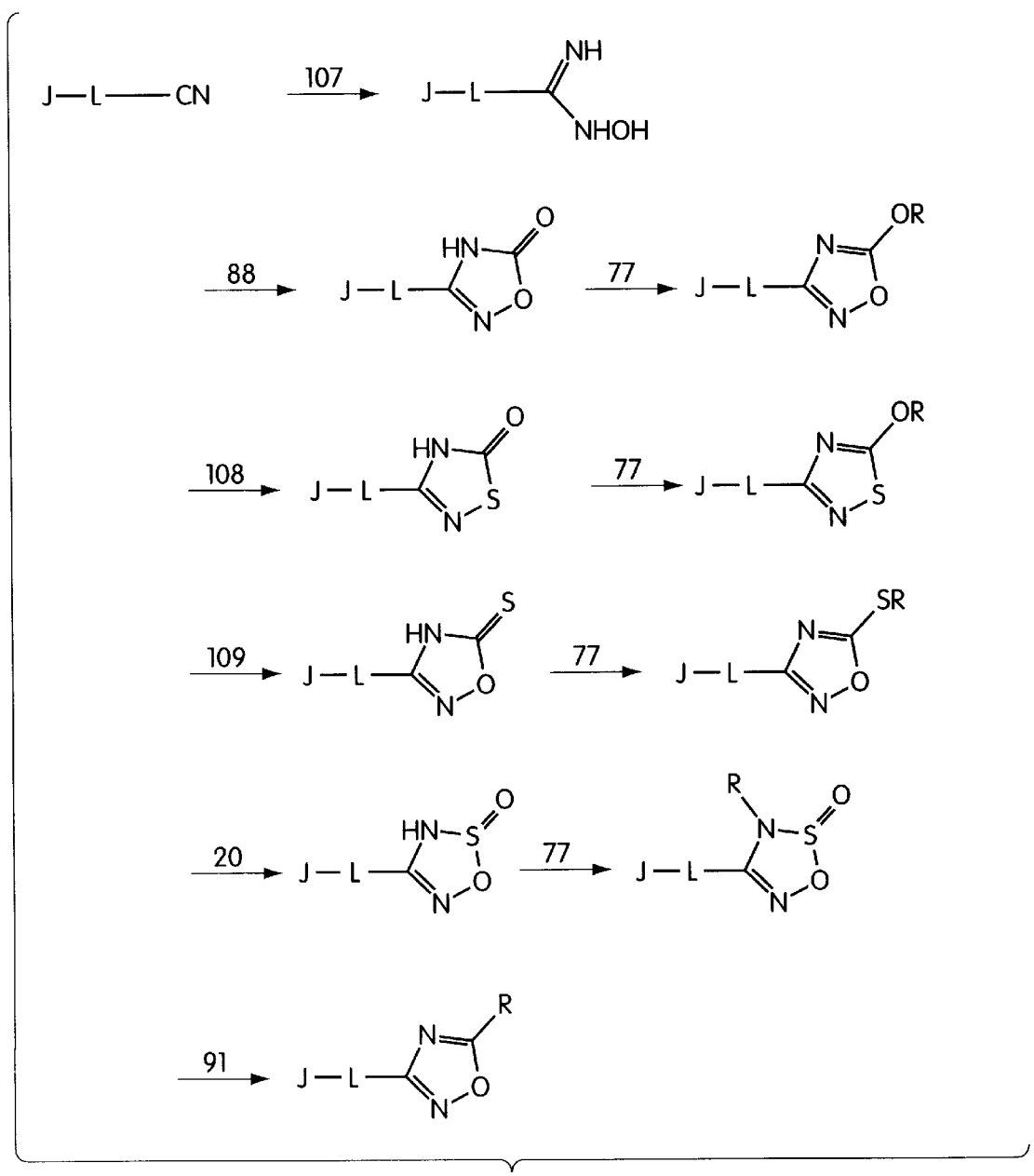
Figure 28:
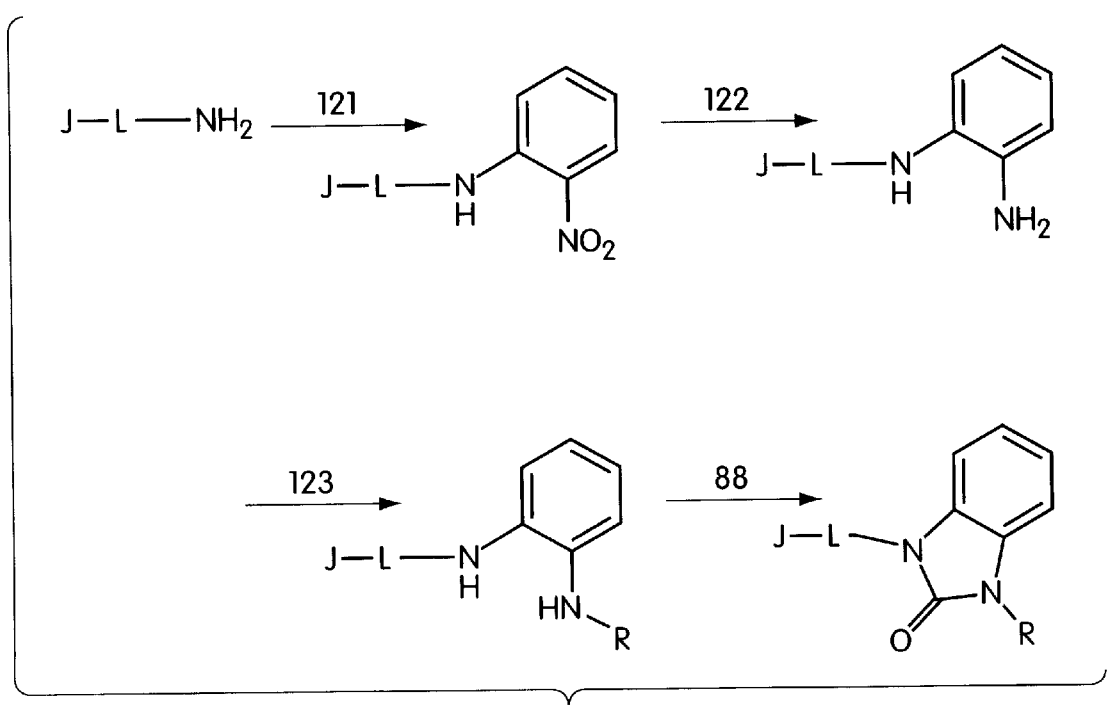
Figure 29:
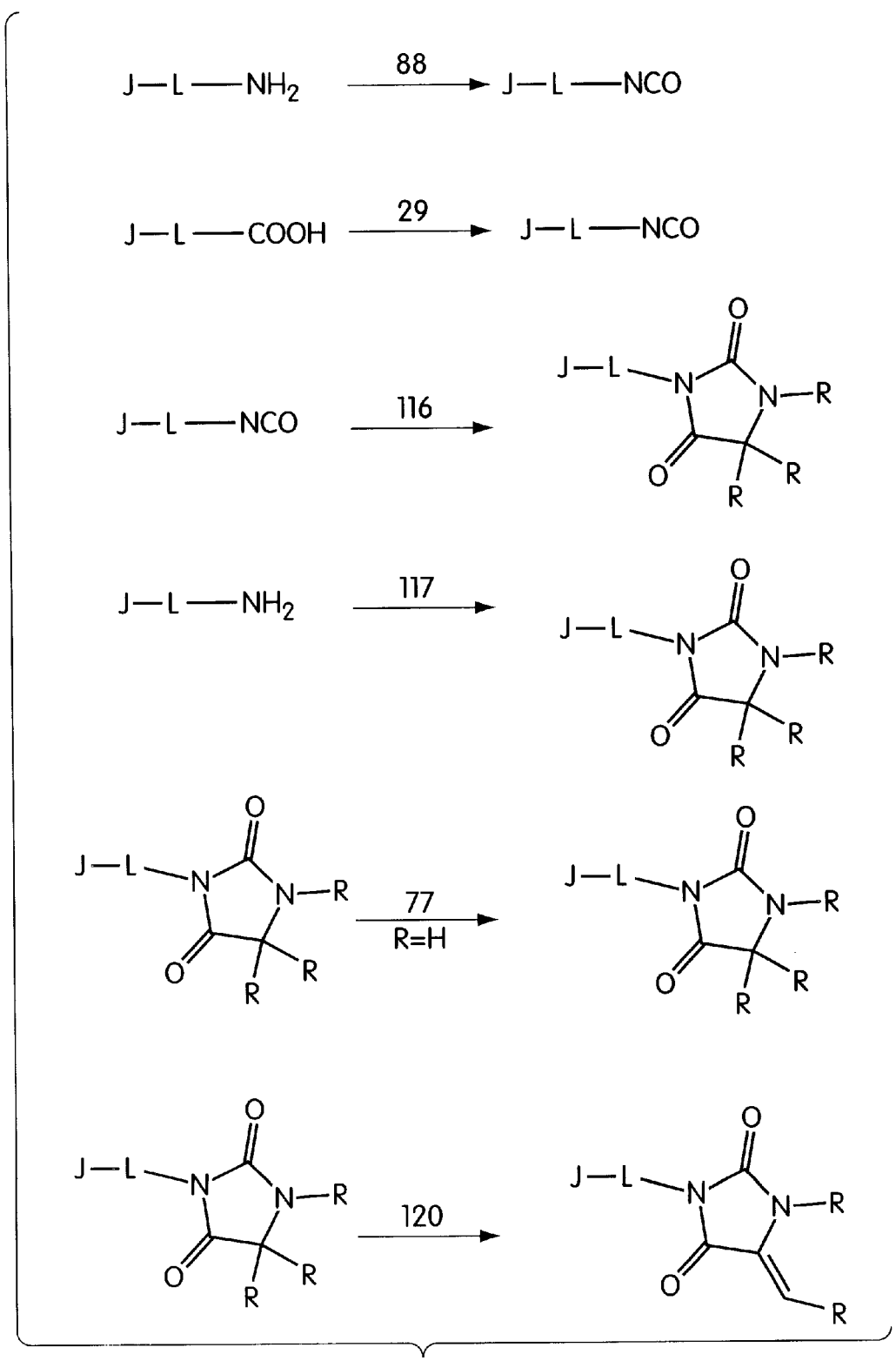
Figure 30:
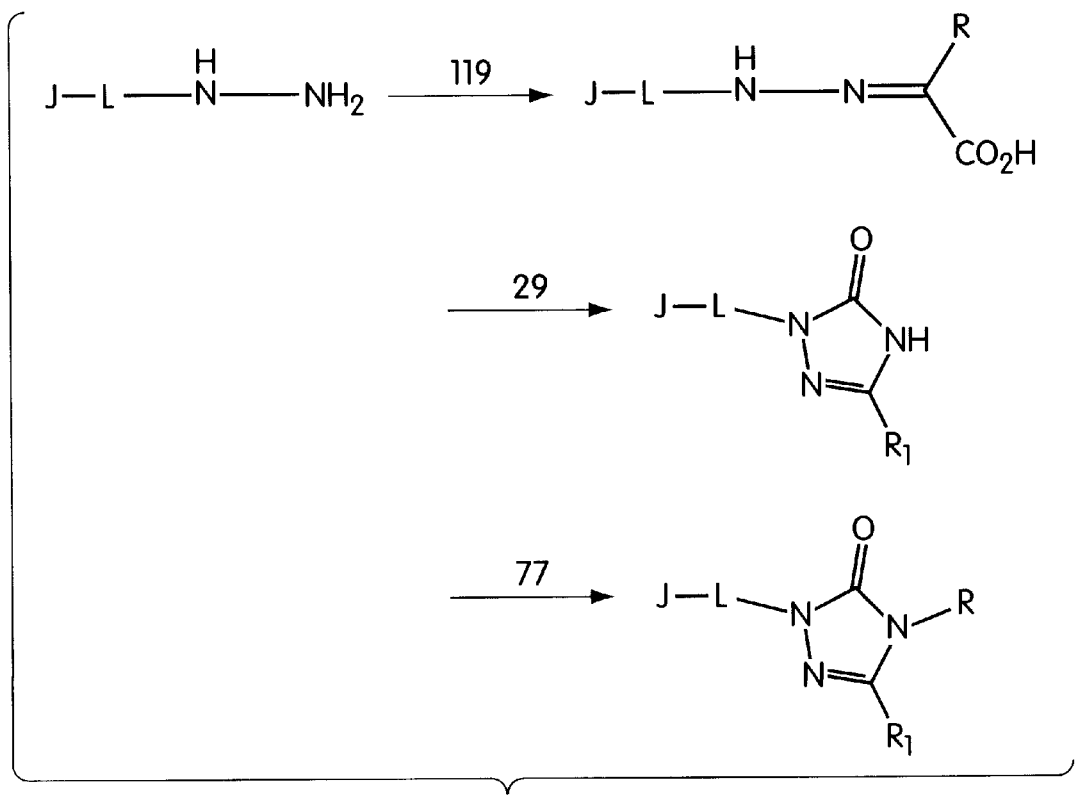
Figure 31:
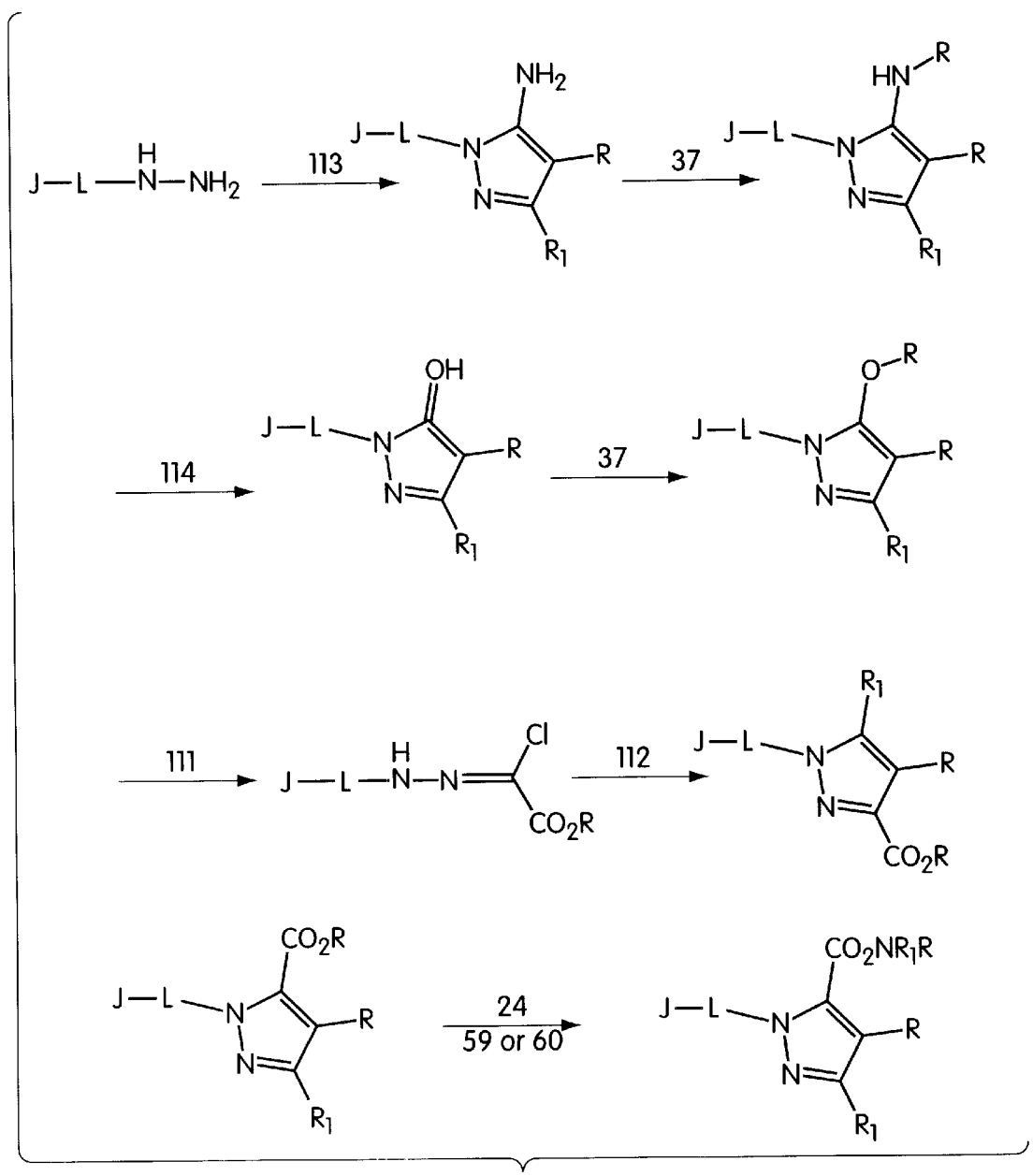
Figure 32A:
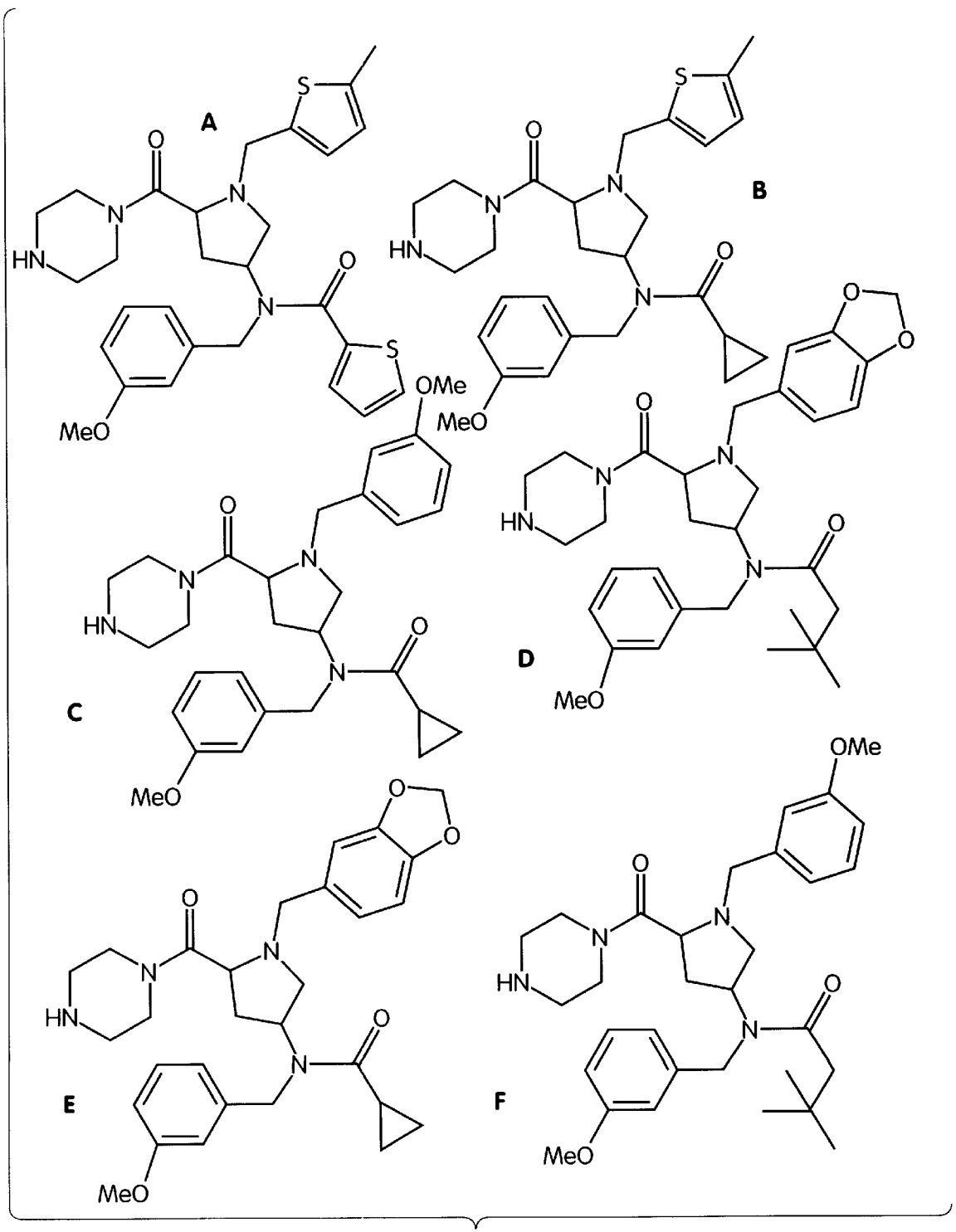
FIGS. 32a–o illustrates representative compounds according to the present invention.
Figure 32B:
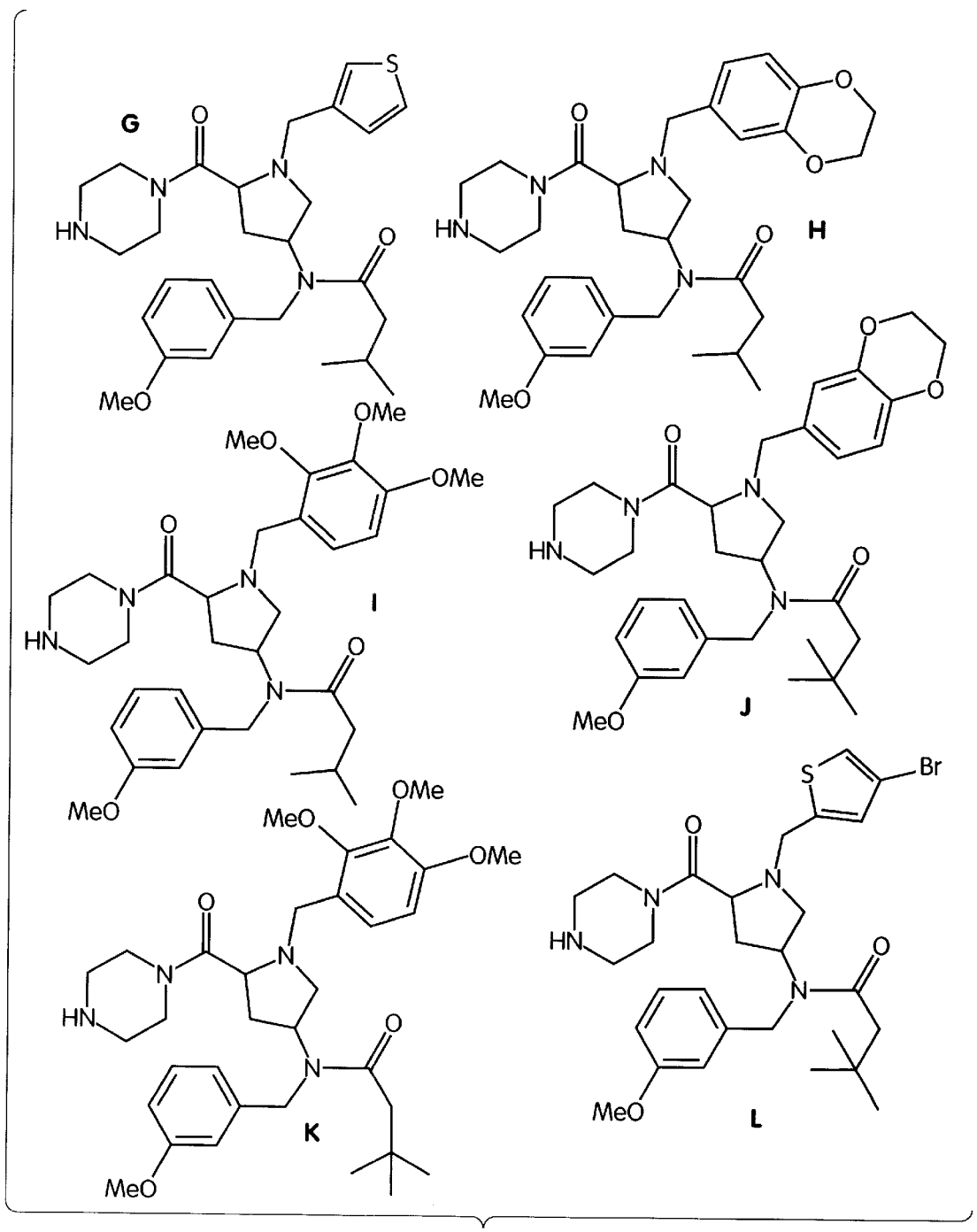
Figure 32C:
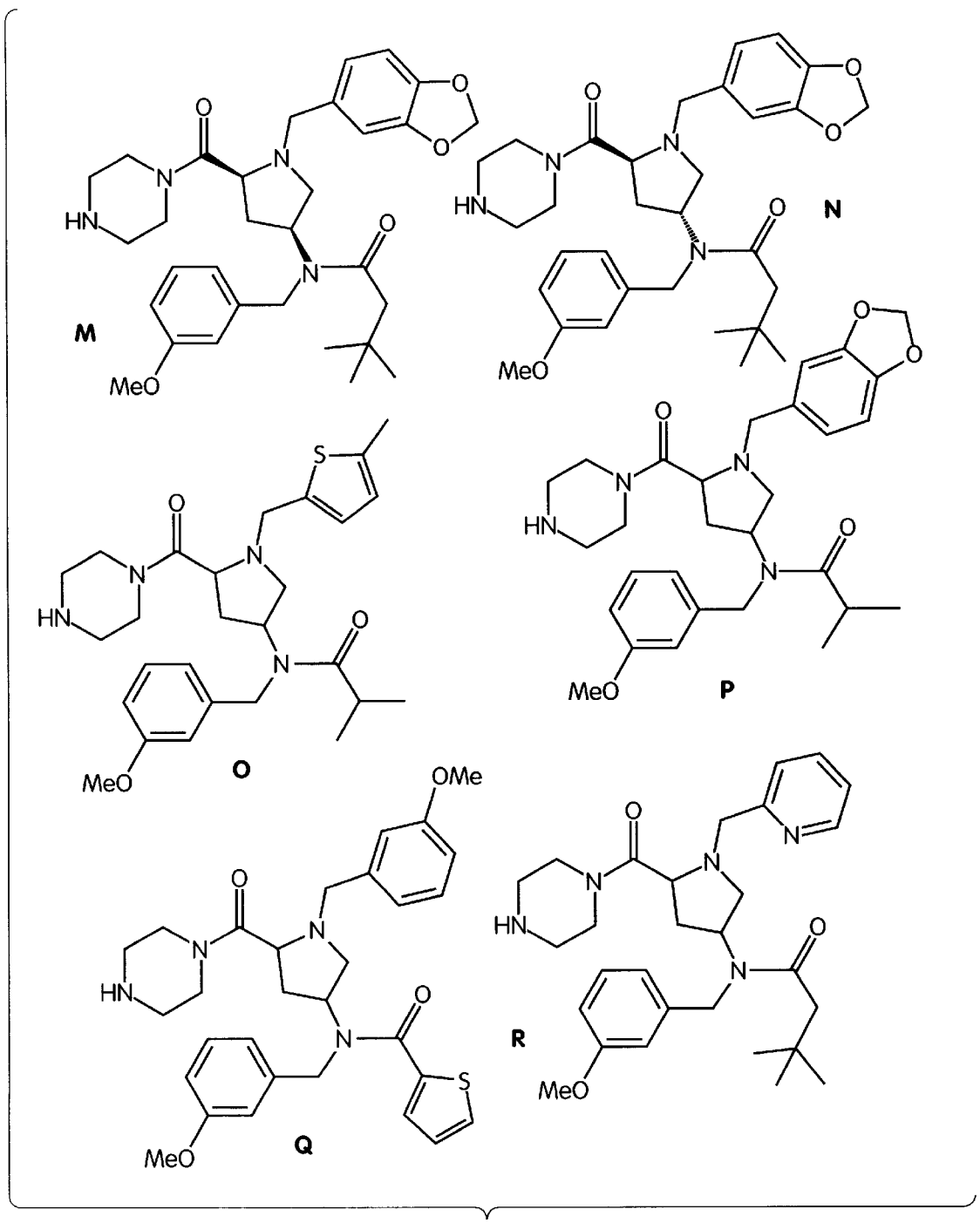
Figure 32D:
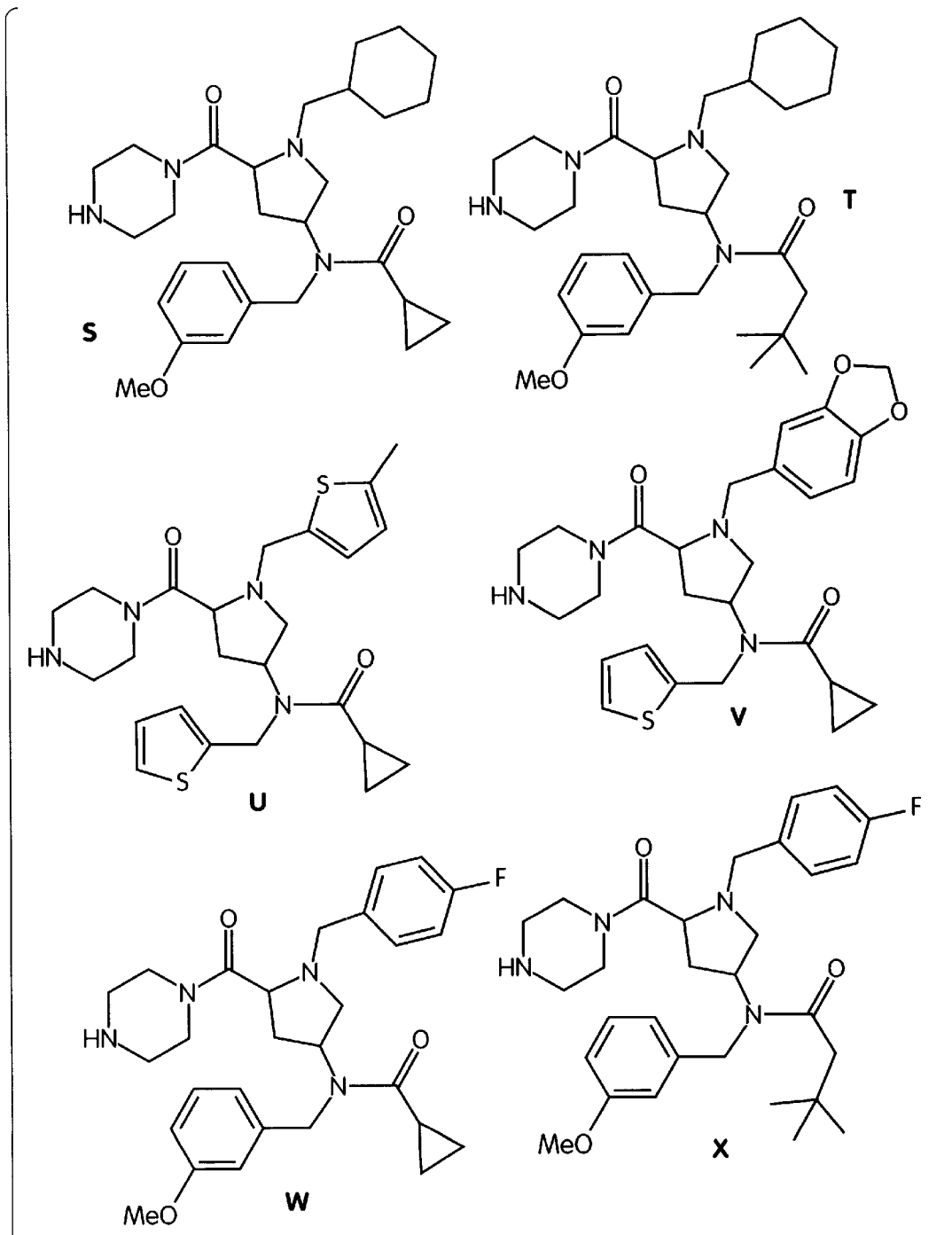
Figure 32E:
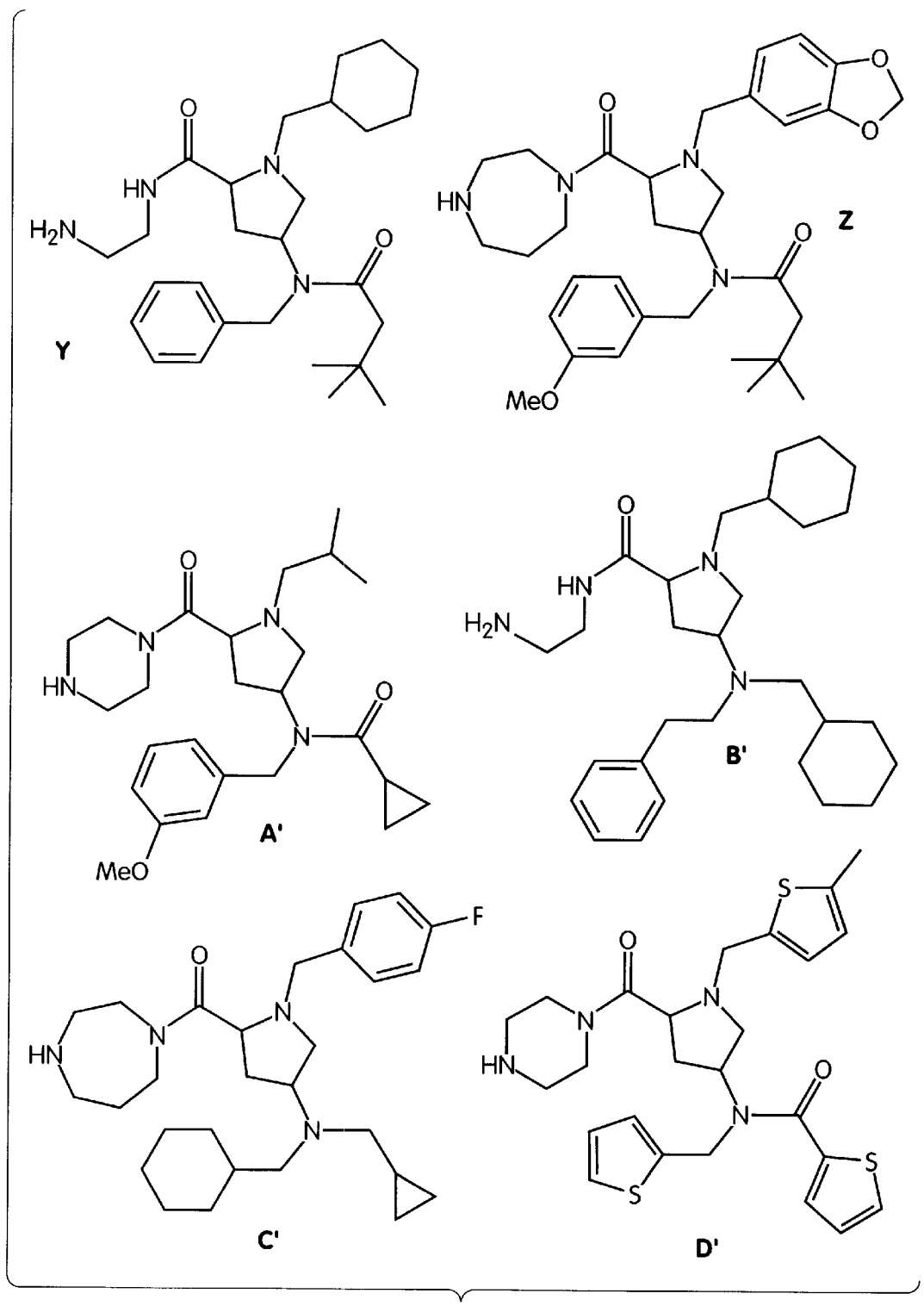
Figure 32F:
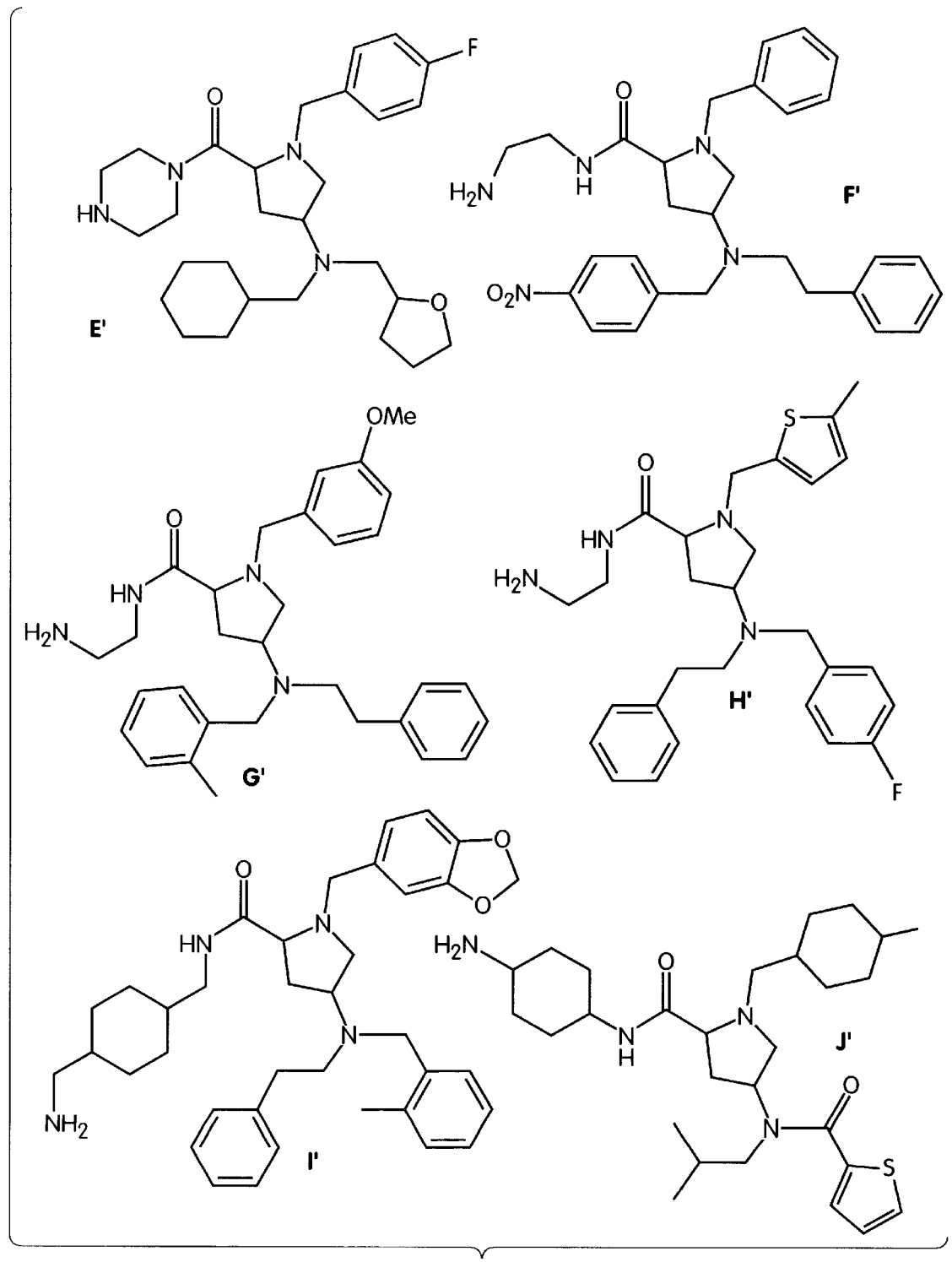
Figure 32G:
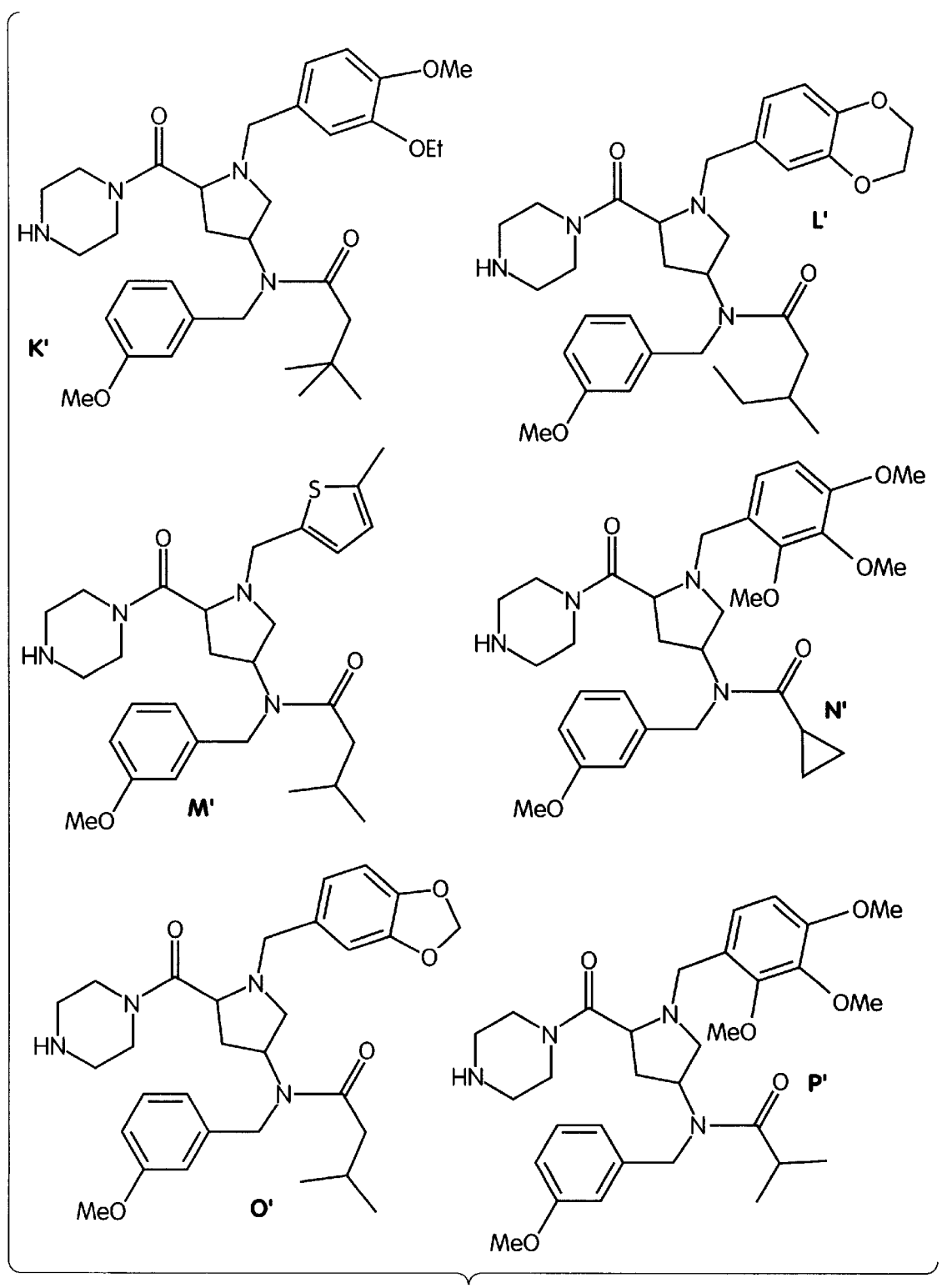
Figure 32H:
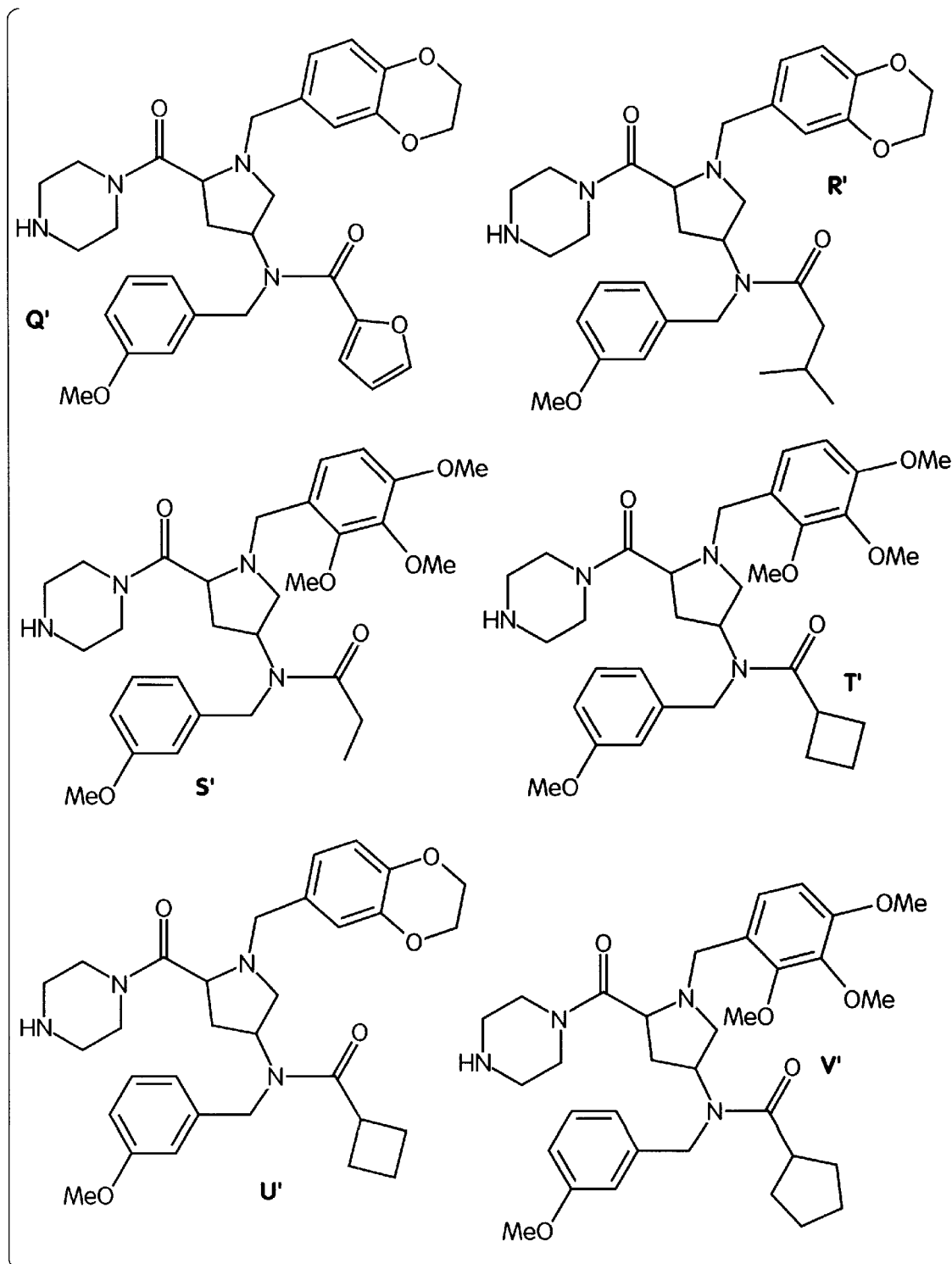
Figure 32I:
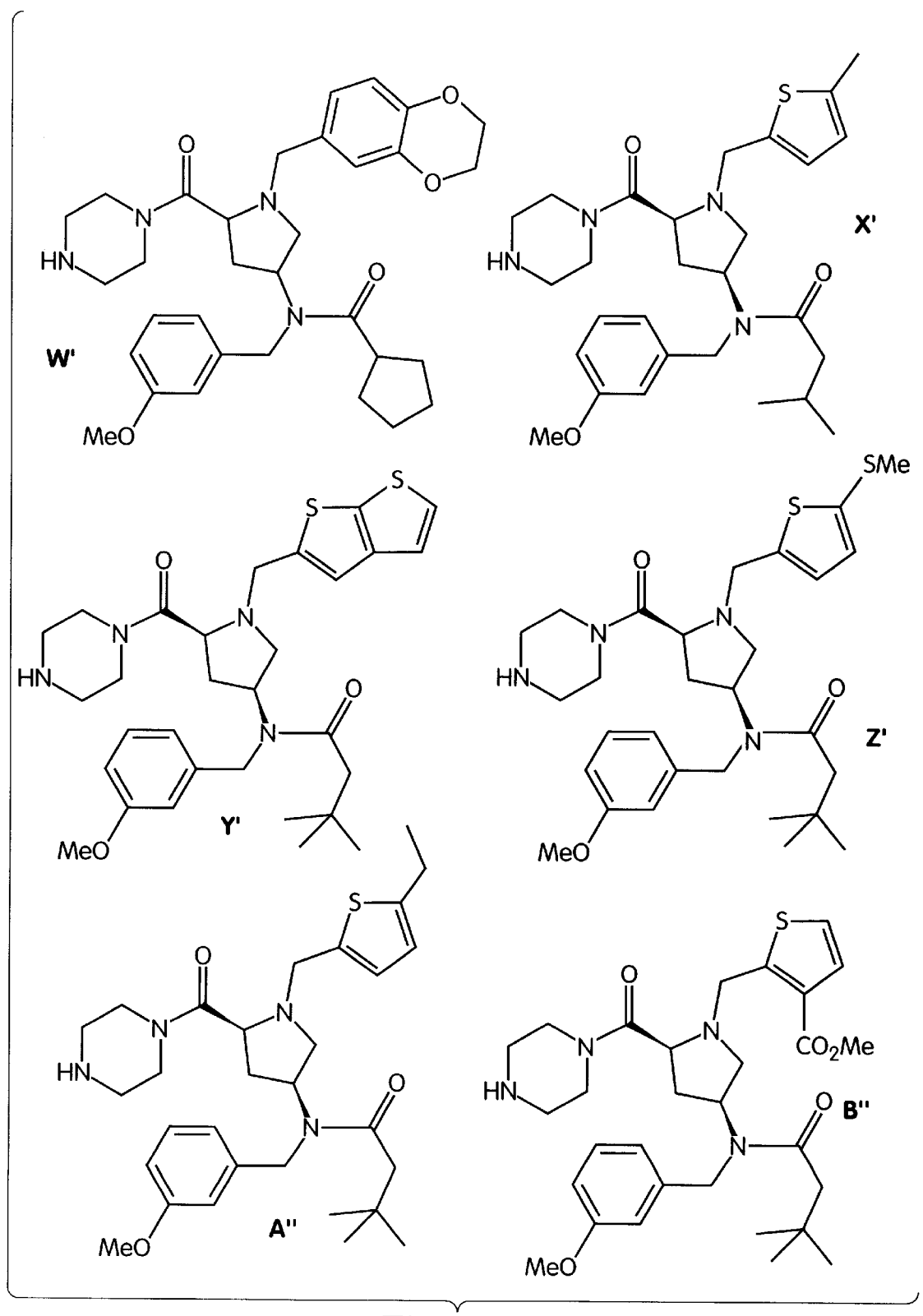
Figure 32J:
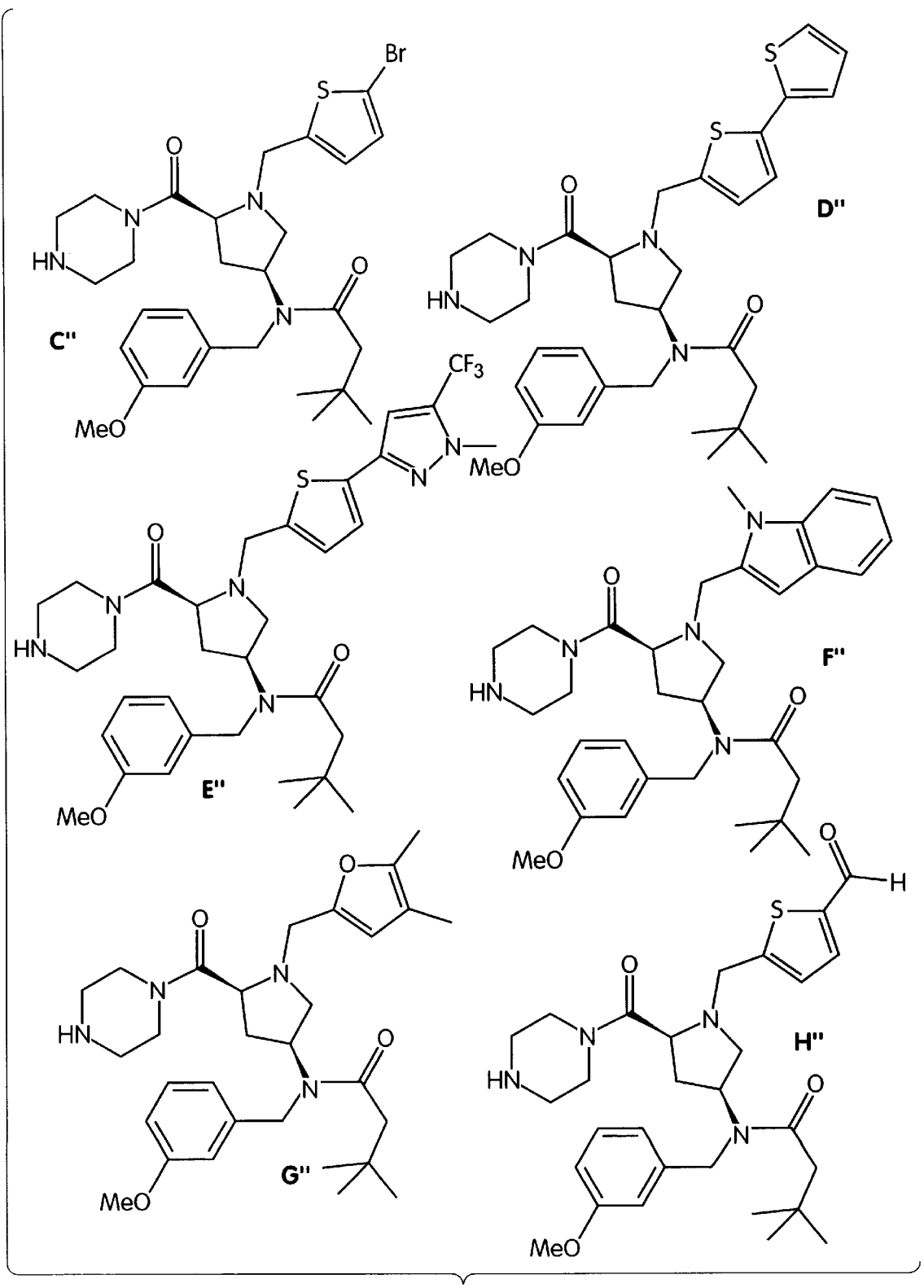
Figure 32K:
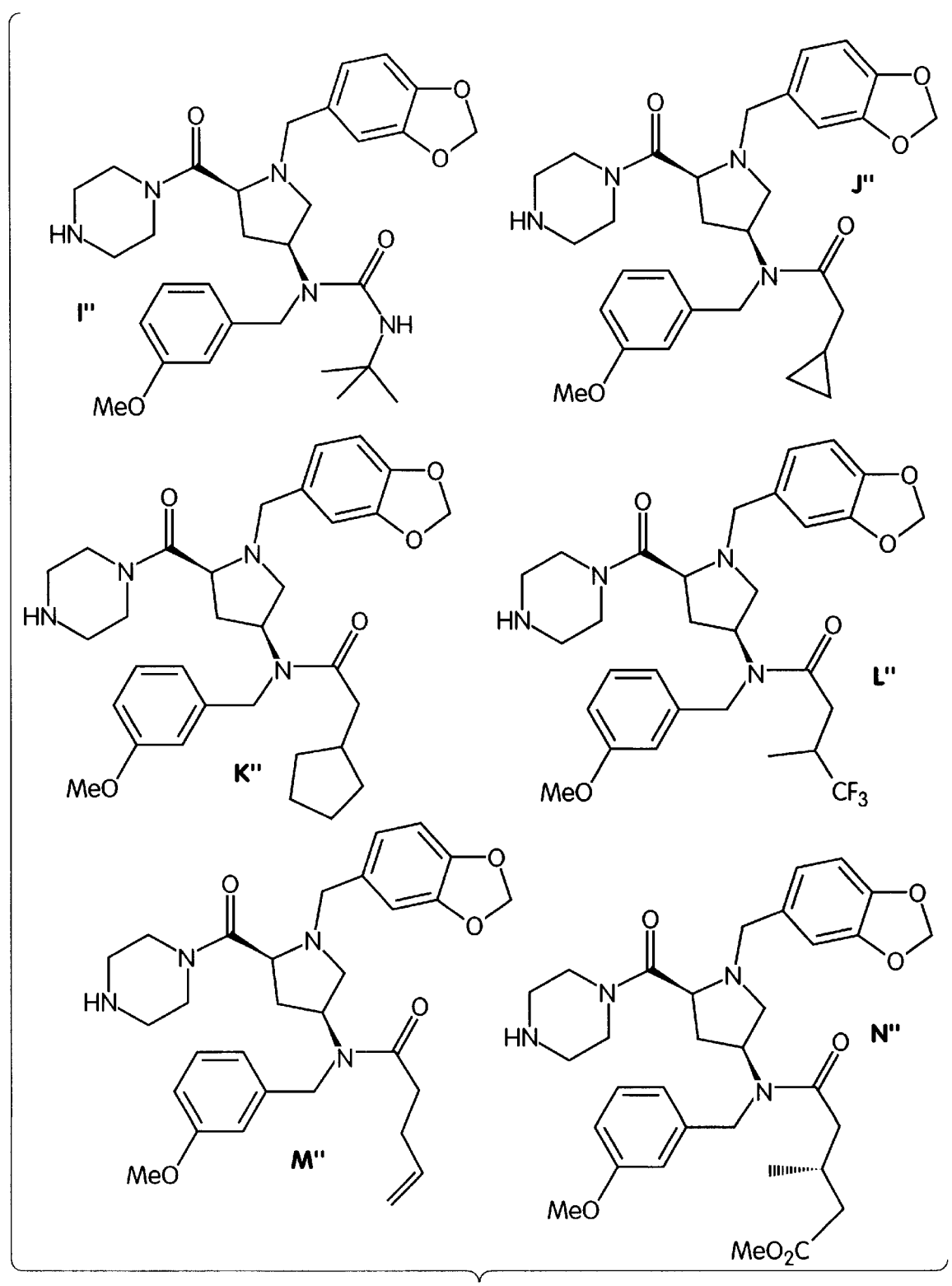
Figure 32L:
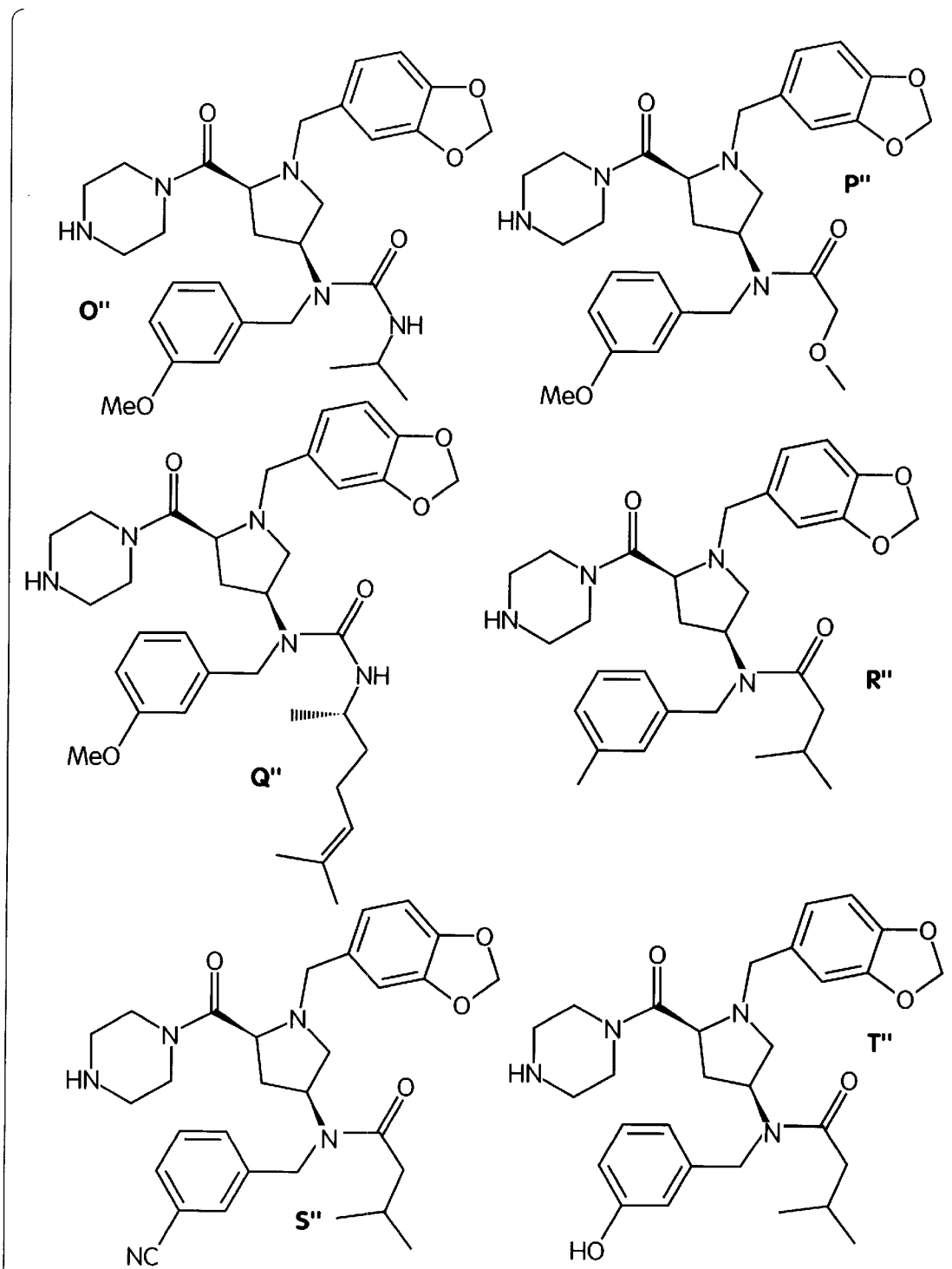
Figure 32M:
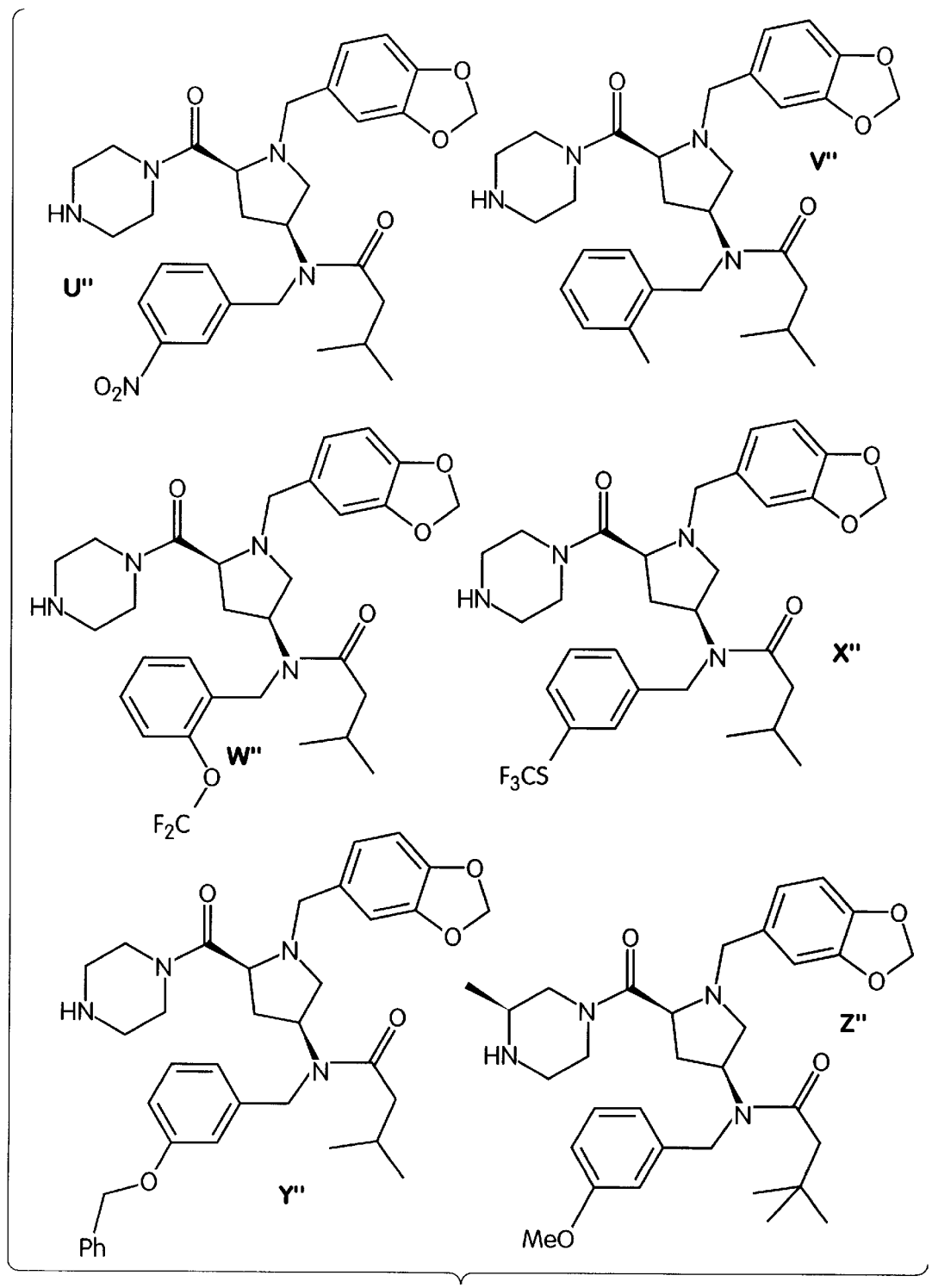
Figure 32N:
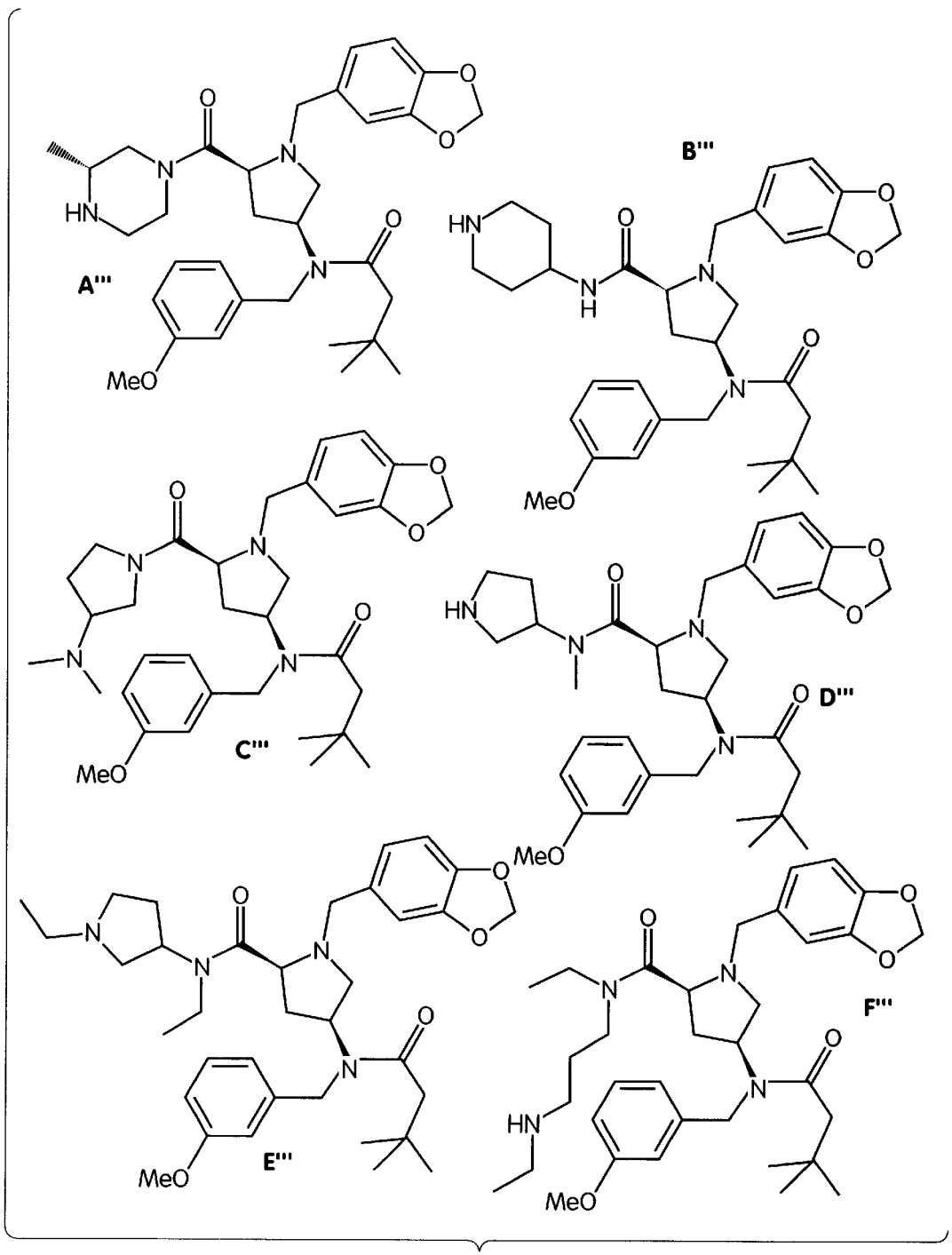
Figure 32O:
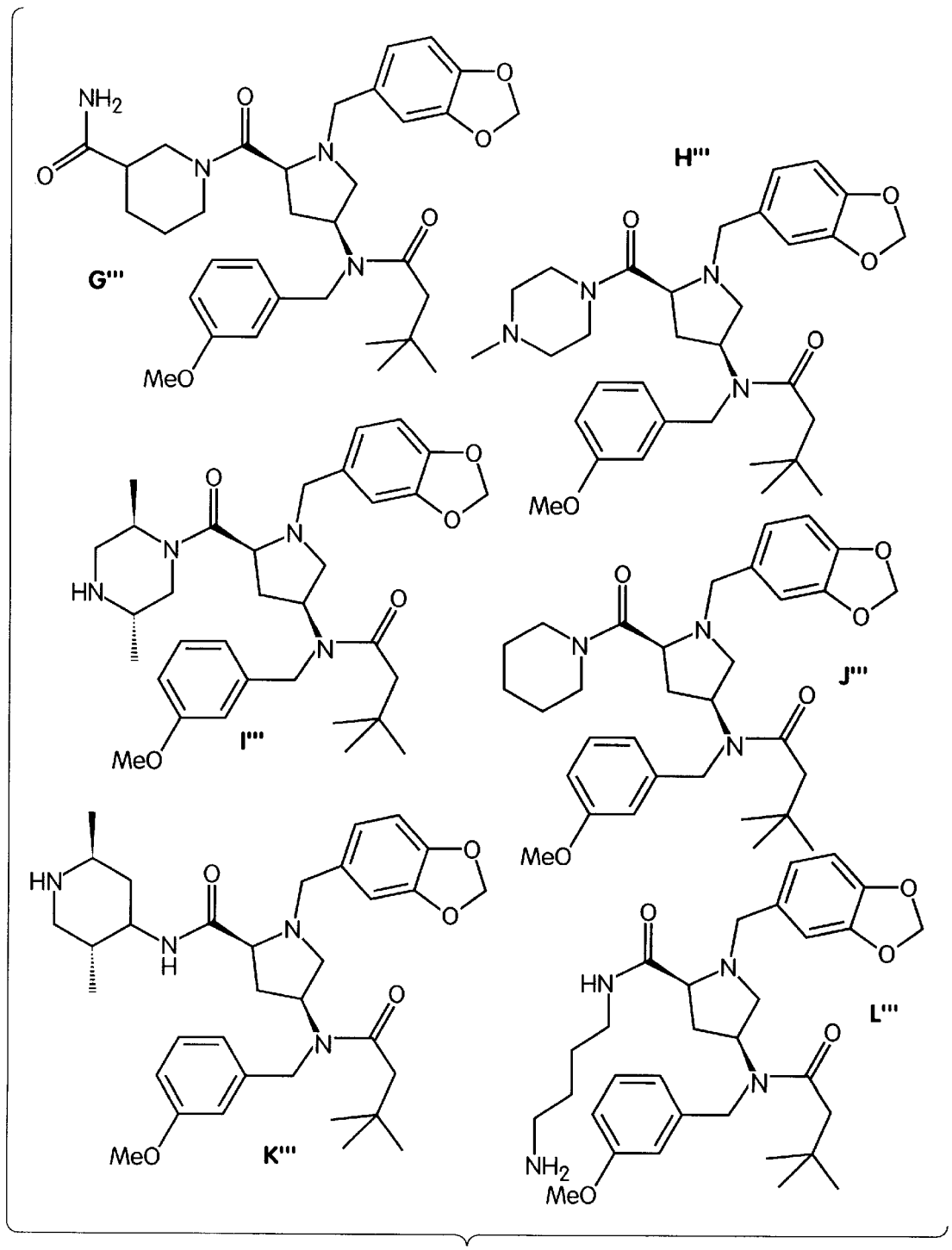

The present invention relates to the discovery that signal transduction pathways regulated by hedgehog, patched (ptc), gli and/or smoothened can be inhibited, at least in part, by small molecules. While not wishing to bound by any particular theory, the activation of a receptor may be the mechanism by which these agents act. For example, the ability of these agents to inhibit proliferation of patched loss-of-function ($ptc^{lof}$) cells may be due to the ability of such molecules to interact with hedgehog, patched, or smoothened, or at least to interfere with the ability of those proteins to activate a hedgehog, ptc, and/or smoothened-mediated signal transduction pathway.

It is, therefore, specifically contemplated that these small molecules which intefere with aspects of hedgehog, ptc, or smoothened signal transduction activity will likewise be capable of inhibiting proliferation (or other biological consequences) in normal cells and/or cells having a patched loss-of-function phenotype, a hedgehog gain-of-function phenotype, or a smoothened gain-of-function phenotype. Thus, it is contemplated that in certain embodiments, these compounds may be useful for inhibiting hedgehog activity in normal cells, e.g., which do not have a genetic mutation that activates the hedgehog pathway. In preferred embodiments, the subject inhibitors are organic molecules having a molecular weight less than 2500 amu, more preferably less than 1500 amu, and even more preferably less than 750 amu, and are capable of inhibiting at least some of the biological activities of hedgehog proteins, preferably specifically in target cells.

Thus, the methods of the present invention include the use of small molecules which agonize ptc inhibition of hedgehog signalling, such as by inhibiting activation of smoothened or downstream components of the signal pathway, in the regulation of repair and/or functional performance of a wide range of cells, tissues and organs, including normal cells, tissues, and organs, as well as those having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In a preferred embodiment, the subject method can be to treat epithelial cells having a phenotype of ptc loss-of-function, hedgehog gain-of-function, or smoothened gain-of-function. For instance, the subject method can be used in treating or preventing basal cell carcinoma or other hedgehog pathway-related disorders.

In certain embodiments, a subject antagonist may inhibit activation of a hedgehog pathway by binding to smoothened. In certain embodiments, a subject antagonist may inhibit activation of a hedgehog pathway by binding to patched.

In another preferred embodiment, the subject method can be used as part of a treatment regimen for malignant medulloblastoma and other primary CNS malignant neuroectodermal tumors.

In another aspect, the present invention provides pharmaceutical preparations comprising, as an active ingredient, a hedgehog antagonist, ptc agonist, or smoothened antagonist such as described herein, formulated in an amount sufficient to inhibit, in vivo, proliferation or other biological consequences of ptc loss-of-function, hedgehog gain-of-function, or smoothened gain-of-function.

The subject treatments using hedgehog antagonists, patched agonists, or smoothened antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Burn wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

An "effective amount" of, e.g., a hedgehog antagonist, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07–1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "hedgehog antagonist" refers to an agent which potentiates or recapitulates the bioactivity of patched, such as to repress transcription of target genes. Preferred hedgehog antagonists can be used to overcome a ptc loss-of-function and/or a smoothened gain-of-function, the latter also being refered to as smoothened antagonists. The term 'hedgehog antagonist' as used herein refers not only to any agent that may act by directly inhibiting the normal function of the hedgehog protein, but also to any agent that inhibits the hedgehog signalling pathway, and thus recapitulates the function of ptc.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signalling pathway would have a 'hedgehog gain-of-function' phenotype, even if hedgehog is not mutated in that cell.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized -by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "nail" refers to the horny cutaneous plate on the dorsal surface of the distal end of a finger or toe.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The loss-of-function may include a loss of the ability of the ptc gene product to regulate the level of expression of Ci genes, e.g., Gli1, Gli2 and Gli3. The term 'ptc loss-of-function' is also used herein to refer to any similar cellular phenotype (e.g., exhibiting excess proliferation) which occurs due to an alteration anywhere in the hedgehog signal transduction pathway, including, but not limited to, a modification or mutation of ptc itself. For example, a tumor cell with an abnormally high proliferation rate due to activation of the hedgehog signalling pathway would have a 'ptc loss-of-function' phenotype, even if ptc is not mutated in that cell.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "smoothened gain-of-function" refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) Nature 384: 177–179). The gene smo is a segment-polarity gene required for the correct patterning of every segment in Drosophila (Alcedo et al., (1996) Cell 86: 221–232). Human homologs of smo have been identified. See, for example, Stone et al. (1996) Nature 384:129–134, and GenBank accession U84401. The smoothened gene encodes an integral membrane protein with characteristics of heterotrimeric G-protein-coupled receptors; i.e., 7-transmembrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) Nature 384: 119–120). Rather, the binding of Sonic hedgehog (SHH) to its receptor, PTCH, is thought to prevent normal inhibition by PTCH of smoothened (SMO), a seven-span transmembrane protein.

Recently, it has been reported that activating smoothened mutations occur in sporadic basal cell carcinoma, Xie et al. (1998) Nature 391: 90–2, and primitive neuroectodermal tumors of the central nervous system, Reifenberger et al. (1998) Cancer Res 58: 1798–803.

The term "therapeutic index" refers to the therapeutic index of a drug defined as $LD_{50}/ED_{50}$.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "acylamino" is art-recognized and refers to a moiety that can be represented by the general formula:

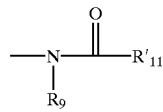

wherein $R_9$ is as defined above, and $R'_{11}$ represents a hydrogen, an alkyl, an alkenyl or —$(CH_2)_m$—$R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

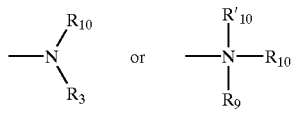

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

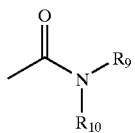

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term. "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

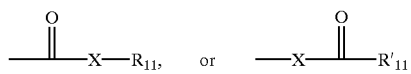

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

A "phosphonamidite" can be represented in the general formula:

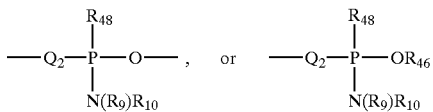

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in the general formula:

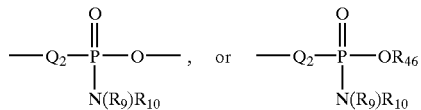

wherein $R_9$ and $R_{10}$ are as defined above, and $Q_2$ represents O, S or N.

A "phosphoryl" can in general be represented by the formula:

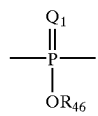

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

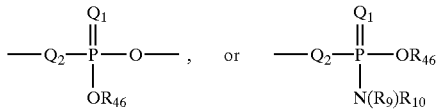

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH₂)$_m$—R₈, m and R₈ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

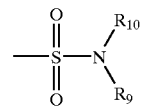

in which $R_9$ and $R_{10}$ are as defined above.

The term "sulfate" is art recognized and includes a moiety that can be represented by the general formula:

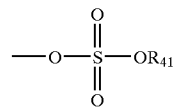

in which $R_{41}$ is as defined above.

The term "sulfonamido" is art recognized and includes a moiety that can be represented by the general formula:

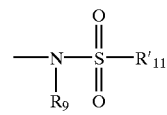

in which $R_9$ and $R'_{11}$ are as defined above.

The term "sulfonate" is art-recognized and includes a moiety that can be represented by the general formula:

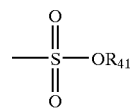

in which $R_{41}$ is an electron pair, hydrogen, alkyl, cycloalkyl, or aryl.

The terms "sulfoxido" or "sulfinyl", as used herein, refers to a moiety that can be represented by the general formula:

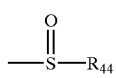

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Compounds of the Invention

As described in further detail below, it is contemplated that the subject methods can be carried out using a variety of different small molecules which can be readily identified, for example, by such drug screening assays as described herein. For example, compounds useful in the subject methods include compounds may be represented by general formula (I):

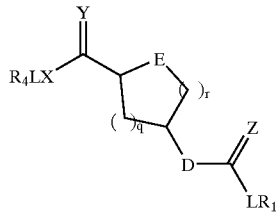

Formula I wherein, as valence and stability permit, $R_1$, $R_2$, $R_3$, and $R_4$, independently for each occurrence, represent H, lower alkyl, —$(CH_2)_n$aryl (e.g., substituted or unsubstituted), or —$(CH_2)_n$heteroaryl (e.g., substituted or unsubstituted);

L, independently for each occurrence, is absent or represents —$(CH_2)_n$—, -alkenyl-, -alkynyl-, —$(CH_2)_n$alkenyl-, —$(CH_2)_n$alkynyl-, —$(CH_2)_nO(CH_2)_p$—, —$(CH_2)_nNR_8(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_8(CH_2)_n$—, or —$S(CH_2)_n$—;

X and D, independently, can be selected from —$N(R_8)$—, —O—, —S—, —$(R_8)N$—$N(R_8)$—, —$ON(R_8)$—, or a direct bond;

Y and Z, independently, can be selected from O or S;

E represents O, S, or $NR_5$, wherein $R_5$ represents $LR_8$ or —(C=O)$LR_8$.

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring;

p represents, independently for each occurrence, an integer from 0 to 10, preferably from 0 to 3;

n, individually for each occurrence, represents an integer from 0 to 10, preferably from 0 to 5; and q and r represent, independently for each occurrence, an integer from 0–2.

In certain embodiments, D does not represent N-lower alkyl. In certain embodiments, D represents an aralkyl- or heteroaralkyl-substituted amine.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, Y and Z are O.

In certain embodiments, the sum of q and r is less than 4, e.g., is 2 or 3.

In certain embodiments, $XLR_4$, taken together, include a cyclic amine, such as a piperazine, a morpholine, a piperidine, a pyrrolidine, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, E is $NR_8$. In certain embodiments, E represents an aralkyl- or heteroaralkyl-substituted amine, e.g., including polycyclic $R_8$.

In certain embodiments, X is not NH. In certain embodiments, X is included in a ring, or, taken together with —C(=Y)—, represents a tertiary amide.

In certain embodiments, compounds useful in the present invention may be represented by general formula (II):

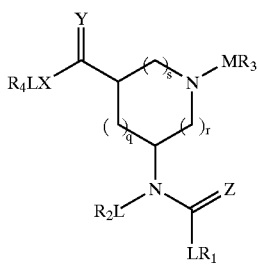

Formula II wherein, as valence and stability permit, $R_1$, $R_2$, $R_3$, $R_4$, $R_8$, L, X, Y, Z, n, p, q, and r are as defined above;

M is absent or represents L, —$SO_2L$—, or —(C=O)L—; and s represents, independently for each occurrence, an integer from 0–2.

In certain embodiments, Y and Z are O.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q, r, and s is less than 5, e.g., is 2, 3, or 4.

In certain embodiments, $XLR_4$, taken together, include a cyclic amine, such as a piperazine, a morpholine, a piperidine, a pyrrolidine, etc.

In certain embodiments, L attached to $R_1$ represents O, S, or $NR_8$, such as NH.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (III):

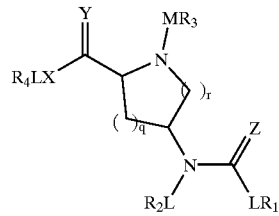

Formula III wherein, as valence and stability permit, $R_1$, $R_2$, $R_3$, $R_4$, $R_8$, L, M, X, Y, Z, n, p, q, and r are as defined above.

In certain embodiments, Y and Z are O.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q and r is less than 4, e.g., is 2 or 3.

In certain embodiments, $XLR_4$, taken together, include a cyclic amine, such as a piperazine, a morpholine, a piperidine, a pyrrolidine, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (IV):

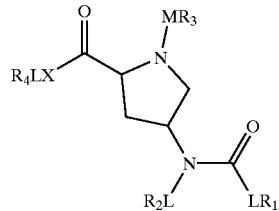

Formula IV wherein, as valence and stability permit, $R_1$, $R_2$, $R_3$, $R_4$, $R_8$, L, M, X, n, and p are as defined above.

In certain embodiments, $XLR_4$, taken together, include a cyclic amine, such as a piperazine, a morpholine, a piperidine, a pyrrolidine, etc.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments L represents a direct bond for all occurrences.

In certain embodiments, compounds useful in the present invention may be represented by general formula (V):

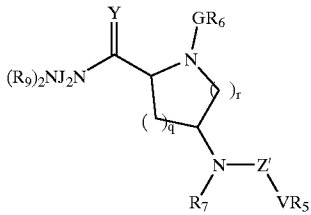

Formula V wherein, as valence and stability permit,

Y, n, p, q, and r are as defined above;

Z' represents —C(=O)—, —C(=S)—, —C(=NH)—, $SO_2$, or SO, preferably —C(=O)—, —C(=S)—;

V is absent or represents O, S, or $NR_8$;

G is absent or represents —C(=O)— or —$SO_2$—;

J, independently for each occurrence, represents H or substituted or unsubstituted lower alkyl or alkylene, such as methyl, ethyl, methylene, ethylene, etc., attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 8 members, which ring includes one or both occurrences of N;

$R_5$ represents substituted or unsubstituted alkyl (e.g., branched or unbranched), alkenyl (e.g., branched or unbranched), alkynyl (e.g., branched or unbranched), cycloalkyl, or cycloalkylalkyl;

$R_6$ represents substituted or unsubstituted aryl, aralkyl, heteroaryl, heteroaralkyl, heterocyclyl, heterocyclylalkyl, cycloalkyl, or cycloalkylalkyl, including polycyclic groups; and $R_7$ represents substituted or unsubstituted aryl, aralkyl, heteroaryl, or heteroaralkyl.

In certain embodiments, Y is O. In certain embodiments, Z' represents $SO_2$, —C(=O)—, or —C(=S)—.

In certain embodiments, the sum of q and r is less than 4.

In certain embodiments, $NJ_2N$, taken together, represent a cyclic diamine, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring which comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

In certain embodiments, compounds useful in the present invention may be represented by general formula (VI):

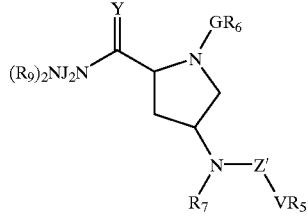

Formula VI wherein, as valence and stability permit, $R_5$, $R_6$, $R_7$, $R_8$, $R_9$, $R_{10}$, G, J, V, Y, Z', n, and p are as defined above.

In certain embodiments, Y is O. In certain embodiments, Z' represents $SO_2$, —(=O)—, or —C(=S)—.

In certain embodiments, $NJ_2N$, taken together, represent a heterocyclic ring, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring which comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

In certain embodiments, the subject compound is selected from the compounds depicted in FIG. 32.

In certain embodiments, the subject antagonists can be chosen on the basis of their selectively for the hedgehog pathway. This selectivity can be for the hedgehog pathway versus other pathways, or for selectivity between particular hedgehog pathways, e.g., ptc-1, ptc-2, etc.

In certain preferred embodiments, the subject inhibitors inhibit ptc loss-of-function, hedgehog gain-of-function, or smoothened gain-of-function mediated signal transduction with an $ED_{50}$ of 1 mM or less, more preferably of 1 μM or less, and even more preferably of 1 nM or less. Similarly, in certain preferred embodiments, the subject inhibitors inhibit activity of the hedgehog pathway with a $K_i$ less than 10 nM, preferably less than 1 nM, even more preferably less than 0.1 nM.

In particular embodiments, the small molecule is chosen for use because it is more selective for one patched isoform over the next, e.g., 10-fold, and more preferably at least 100- or even 1000-fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a $K_i$ at least an order of magnitude lower than its $K_i$ for inhibition of PKC, preferably at least two orders of magnitude lower, even more preferably at least three orders of magnitude lower. In certain embodiments, the $K_i$ for PKA inhibition is less than 10 nM, preferably less than 1 nM, even more preferably less than 0.1 nM.

METHODS OF PREPARATION OF SUBJECT COMPOUNDS

The present invention further provides methods for preparing the subject compounds, as set forth above. For example, in one embodiment, a compound of Formula X may be transformed according to the following scheme:

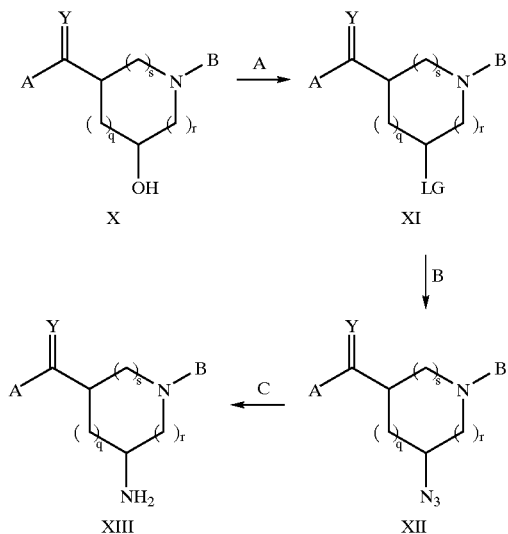

wherein q, s, and r each represent, independently, an integer in the range of 0 to 2, such that the sum of q+s+r is an integer in the range of 2–4;

LG represents a leaving group, such as a halogen (e.g., Cl, Br, or I) or a sulfonate ester (e.g., tosylate, mesylate, triflate, etc.);

A represents an oxygen or sulfur bound to an acid-protecting group or a group having the formula $XLR_4$;

B represents a nitrogen-protecting group or a group having the formula $MR_3$;

$R_3$ and $R_4$, independently for each occurrence, represent H, lower alkyl, —$(CH_2)_n$aryl (e.g., substituted or unsubstituted), or —$(CH_2)_n$heteroaryl (e.g., substituted or unsubstituted);

Y can be selected from O and S;

X is be selected from —$N(R_8)$—, —O—, —S—, or a direct bond;

M is absent or represents L, —$SO_2L$—, or —$(C=O)L$—;

L, independently for each occurrence, is absent or represents —$(CH_2)_n$alkyl-, -alkenyl-, -alkynyl-, —$(CH_2)_n$ alkenyl-, —$(CH_2)_n$alkynyl-, —$(CH_2)_nO(CH_2)_p$—, —$(CH_2)_nNR_8(CH_2)_p$—, —$(CH_2)_nS(CH_2)_p$, —$(CH_2)_n$ alkenyl$(CH_2)_p$—, —$(CH_2)_n$alkynyl$(CH_2)_p$—, —$O(CH_2)_n$—, —$NR_8(CH_2)_n$—, or —$S(CH_2)_n$—;

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring;

p represents, independently for each occurrence, an integer from 0 to 10, preferably from 0 to 3; and n, individually for each occurrence, represents an integer from 0 to 10, preferably from 0 to 5, and wherein step A includes converting the hydroxyl to a leaving group, step B includes displacing the leaving group with an azide, and step C includes reducing the azide to an amine.

In certain embodiments, converting the hydroxyl to a leaving group may be performed by reacting the hydroxyl with a sulfonyl halide to generate a sulfonate ester, e.g., using tosyl chloride or tosyl anhydride to generate a tosylate, mesyl chloride or mesyl anhydride to generate a mesylate, or triflyl chloride or triflyl anhydride to generate a triflate, etc. In certain other embodiments, converting the hydroxyl to a leaving group may be performed by reacting the hydroxyl with an halogenating reagent such as a thionyl halide, a phosphorous trihalide, phosphorous pentahalide, phosphorous oxyhalide, etc. Other techniques for converting a hydroxyl group to a leaving group are well known in the art and may be used in step A.

In certain embodiments, step A further includes displacing a first leaving group with a second leaving group and inverting the stereochemistry of the leaving group-bearing carbon. Thus, for example, if the hydroxyl of the compound of Formula X has a cis stereochemical relationship with the group bearing Y and A, reaction of this compound with mesyl chloride will generate a mesylate in a cis stereochemical relationship with the group bearing Y and A. Reaction of this mesylate with a nucleophilic halide reagent, such as NaI, will result in displacement of the mesylate with iodide, generating a compound of Formula XI wherein the leaving group, iodine, and the group bearing Y and A have a trans stereochemical relationship. Use of this technique permits compounds having either cis or trans stereochemistry, selectively, from a diastereomerically pure starting material, e.g., a pure compound having a cis stereochemical relationship between the hydroxyl and the group bearing Y and A.

In certain embodiments, displacing the leaving group with an azide may be performed using an alkali or alkaline earth metal salt of azide anion, such as sodium azide, using a silyl azide reagent, such as trimethylsilyl azide, or using any other azide reagent, e.g., a nucleophilic azide source, as is well known in the art.

In certain embodiments, reducing the azide to an amine may be performed using a hydride reagent, such as lithium aluminum hydride, lithium trialkylborohydride, etc., using a reducing metal and an acid source, such as zinc metal or samarium diiodide with acetic acid, using catalytic hydrogenation, such as hydrogen and a transition metal catalyst such as platinum or palladium, or by any other suitable means.

In certain embodiments, q+s+r is an integer from 2 to 3. In certain embodiments, s is 0. In certain embodiments, q and r each represent 1.

In certain embodiments, A represents an oxygen bound to an acid-protecting group. For example, the acid protecting group may be a substituted or unsubstituted alkyl, alkenyl, alkynyl, aryl, or aralkyl group. Examples of such groups include methyl, ethyl, trimethylsilylethyl, methylthiomethyl, allyl, benzyl, p-nitrobenzyl, tetrahydropyranyl (THP), t-butyl, or any other suitable group. A wide variety of acid-protecting groups are known in the art and may be employed in this method without departing from the scope and spirit of the invention. In other embodiments, A represents an alkylthio group.

In certain embodiments, B represents a nitrogen-protecting group, such as a substituted or unsubstituted acyl, alkyl, alkenyl, alkynyl, aryl, or aralkyl group, or a group which, when taken together with N, forms a carbamate. Common nitrogen-protecting groups include benzyl, allyl, p-methoxybenzyl, acetyl, trifluoroacetyl, t-butoxycarbonyl, benzyloxycarbonyl, etc. A wide variety of nitrogen-protecting groups are known in the art and may be employed in this method without departing from the scope and spirit of the invention.

In certain embodiments, Y is O.

In certain embodiments, A represents $XLR_4$, which may, taken together, include a cyclic amine, such as a piperazine, a morpholine, a piperidine, a pyrrolidine, etc.

In certain embodiments, $R_3$ includes an aryl or heteroaryl group.

In certain embodiments, M is absent.

In certain embodiments, X is $NR_8$, and preferably is not NH. In certain embodiments, X is included in a ring, or, taken together with —C(=Y)—, represents a tertiary amide.

In certain embodiments, the compound of Formula XIII is enriched for the isomer wherein the amine and the substituent including Y and A have a cis relationship, e.g., >75%, >85%, or even >95% of the cis isomer. In other embodiments, the compound of Formula XIII is enriched for the isomer wherein the two substituents have a trans relationship, e.g., >75%, >85%, or even >95% of the trans isomer. Preferably, such enrichment results from employing an isomerically enriched starting material, e.g., the compound of Formula X is enriched for, >75%, >85%, or even >95% of the cis or trans isomer prior to beginning step A.

Similarly, in another embodiment, a compound of Formula XIV may be transformed according to the following scheme:

wherein
q and r each represent, independently, an integer in the range of 0 to 2, such that the sum of q+r is an integer in the range of 2–4;

LG represents a leaving group, such as a halogen (e.g., Cl, Br, or I) or a sulfonate ester (e.g., tosylate, mesylate, triflate, etc.);

A represents an oxygen or sulfur bound to an acid-protecting group or a group having the formula $NJ_2N(R_9)_2$;

B represents a nitrogen-protecting group or a group having the formula $GR_6$;

G is absent or represents —C(=O)—, —C(=S)—, or —SO$_2$—;

J, independently for each occurrence, represents H or substituted or unsubstituted lower alkyl or alkylene, such as methyl, ethyl, etc., attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 7 members, which ring includes one or both occurrences of N;

$R_6$ represents substituted or unsubstituted aryl, aralkyl, heteroaryl, heteroaralkyl, heterocyclyl, heterocyclylalkyl, cycloalkyl, or cycloalkylalkyl, including polycyclic groups; and Y can be selected from O and S;

and wherein
step A includes converting the hydroxyl to a leaving group,
step B includes displacing the leaving group with an azide, and
step C includes reducing the azide to an amine.

In certain embodiments, converting the hydroxyl to a leaving group may be performed by reacting the hydroxyl with a sulfonyl halide to generate a sulfonate ester, e.g., using tosyl chloride or tosyl anhydride to generate a tosylate, mesyl chloride or mesyl anhydride to generate a mesylate, or triflyl chloride or triflyl anhydride to generate a triflate, etc. In certain other embodiments, converting the hydroxyl to a leaving group may be performed by reacting the hydroxyl with an halogenating reagent such as a thionyl halide, a phosphorous trihalide, phosphorous pentahalide, phosphorous oxyhalide, etc. Other techniques for converting a hydroxyl group to a leaving group are well known in the art and may be used in step A.

In certain embodiments, step A further includes displacing a first leaving group with a second leaving group and inverting the stereochemistry of the leaving group-bearing carbon. Thus, for example, if the hydroxyl of the compound of Formula XIV has a cis stereochemical relationship with the group bearing Y and A, reaction of this compound with mesyl chloride will generate a mesylate in a cis stereochemical relationship with the group bearing Y and A. Reaction of this mesylate with a nucleophilic halide reagent, such as NaI, will result in displacement of the mesylate with iodide, generating a compound of Formula XV wherein the leaving group, iodine, and the group bearing Y and A have a trans stereochemical relationship. Use of this technique permits compounds having either cis or trans stereochemistry, selectively, from a diastereomerically pure starting material, e.g., a pure compound having a cis stereochemical relationship between the hydroxyl and the group bearing Y and A.

In certain embodiments, displacing the leaving group with an azide may be performed using an alkali or alkaline earth metal salt of azide anion, such as sodium azide, using a silyl azide reagent, such as trimethylsilyl azide, or using any other azide reagent, e.g., a nucleophilic azide source, as is well known in the art.

In certain embodiments, reducing the azide to an amine may be performed using a hydride reagent, such as lithium aluminum hydride, lithium trialkylborohydride, etc., using a reducing metal and an acid source, such as zinc metal or samarium diiodide with acetic acid, using catalytic hydrogenation, such as hydrogen and a transition metal catalyst such as platinum or palladium, or by any other suitable means.

In certain embodiments, q+r is an integer from 2 to 3. In certain embodiments, q and r each represent 1.

In certain embodiments, A represents an oxygen bound to an acid-protecting group. For example, the acid protecting group may be a substituted or unsubstituted alkyl, alkenyl, alkynyl, aryl, or aralkyl group. Examples of such groups include methyl, ethyl, trimethylsilylethyl, methylthiomethyl, allyl, benzyl, p-nitrobenzyl, tetrahydropyranyl (THP), t-butyl, or any other suitable group. A wide variety of acid-protecting groups are known in the art and may be employed in this method without departing from the scope and spirit of the invention. In other embodiments, A represents an alkylthio group.

In certain embodiments, B represents a nitrogen-protecting group, such as a substituted or unsubstituted acyl, alkyl, alkenyl, alkynyl, aryl, or aralkyl group, or a group which, when taken together with N, forms a carbamate. Common nitrogen-protecting groups include benzyl, allyl, p-methoxybenzyl, acetyl, trifluoroacetyl, t-butoxycarbonyl, benzyloxycarbonyl, etc. A wide variety of nitrogen-protecting groups are known in the art and may be employed in this method without departing from the scope and spirit of the invention.

In certain embodiments, Y is O.

In certain embodiments, B is $GR_6$, wherein $R_6$ includes at least one heterocyclic ring, such as a thiophene, furan, oxazole, benzodioxane, benzodioxole, pyrrole, indole, etc.

In certain embodiments, A represents $NJ_2N$, which, taken together, may represent a cyclic diamine, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring which comprises an occurrence of J has from 5 to 8 members.

In certain embodiments, the compound of Formula XVII is enriched for the isomer wherein the amine and the substituent including Y and A have a cis relationship, e.g., >75%, >85%, or even >95% of the cis isomer. In other embodiments, the compound of Formula XVII is enriched for the isomer wherein the two substituents have a trans relationship, e.g., >75%, >85%, or even >95% of the trans isomer. Preferably, such enrichment results from employing an isomerically enriched starting material, e.g., the compound of Formula XIV is enriched for, >75%, >85%, or even >95% of the cis or trans isomer prior to beginning step A.

In certain embodiments, an amine having a structure of Formula XIII or XVII may be further transformed, e.g., by performing additional steps towards generating a compound of at least one of Formulae I–VI. Thus, for example, a method according to the present invention might include one or more of the following steps:

D) coupling to the exocyclic amine a group —C(=Z)$LR_1$ or —Z'V$R_5$;

E) coupling to the exocyclic amine a group —$R_7$ or —L$R_2$;

F) coupling to the group bearing Y a group —$NJ_2N(R_9)_2$ or —$XLR_4$;

G) coupling to the nitrogen in the ring a group —$MR_3$ or —$GR_6$;

H) removing a protecting group from the nitrogen in the ring;

I) removing a protecting group from the group bearing Y;

J) placing a nitrogen-protecting group on the exocyclic amine;

K) removing a protecting group from the exocyclic amine, wherein

L, J, $R_9$, M, $R_3$, and $R_6$ are as defined above, $R_1$, $R_2$, $R_3$, and $R_4$, independently for each occurrence, represent H, lower alkyl, —$(CH_2)_n$aryl (e.g., substituted or unsubstituted), or —$(CH_2)_n$heteroaryl (e.g., substituted or unsubstituted);

Z is O or S;

Z' absent or represents —$SO_2$—, —(C=S)—, or —(C=O)—;

V is absent or represents O, S, or $NR_8$;

$R_5$ represents substituted or unsubstituted alkyl (e.g., branched or unbranched), alkenyl (e.g., branched or unbranched), alkynyl (e.g., branched or unbranched), cycloalkyl, or cycloalkylalkyl; and $R_7$ represents substituted or unsubstituted aryl, aralkyl, heteroaryl, or heteroaralkyl.

Any of steps D through K, as may be selected, may be performed in any order, depending on the various reactions and protecting groups used, as is well understood in the art. Various protecting groups suitable for use in the present method have been outlined above, and are well known in the art, as are numerous techniques for attaching and removing such protecting groups, and any of these may be employed in the present method without departing from the scope and spirit of the present invention.

In certain embodiments, step D may be performed by reacting the exocyclic amine with an acylating agent, such as an acid halide, an isocyanate, an isothiocyanate, a haloformate, a halothioformate, an anhydride, a dicarbonate, a sulfonyl halide, a sulfinyl halide, a carbamyl chloride, a thiocarbamyl chloride, or an activated acylating moiety prepared in situ. An acylating agent may be prepared in situ, for example, by reacting a carboxylic acid with an activating agent, such as a carbodiimide (e.g., diisopropylcarbodiimide, dicyclohexylcarbodiimide, 1-(3-dimethylaminopropyl)-3-ethylcarbodiimide, etc.), phosphorous-based reagents (such as BOP—Cl, PyBROP, etc.), oxalyl chloride, phosgene, triphosgene, or any other reagent that reacts with a carboxylic acid group resulting in a reactive intermediate having an increased susceptibility, relative to the carboxylic acid, towards coupling with an amine. A wide variety of such reagents are well known in the art of organic synthesis, especially peptide coupling. Similarly, a primary amine or alcohol can be treated with a phosgene equivalent, such as carbonyl diimidazole, phosgene, triphosgene, diphosgene, etc., or a thiophosgene equivalent, such as thiophosgene, thiocarbonyldiimidazole, etc., to generate an acylating agent (e.g., an isocyanate, isothiocyanate, chloroformamide, or chlorothioformamide, for example) capable of reacting with an amine to form a urea or thiourea, without necessitating isolation or purification of the acylating agent.

In embodiments wherein M or G represents $SO_2$, C=O, or C=S, step G may be performed using reagents and techniques such as those described for step D, above. In embodiments wherein M or G is absent, step G may be performed by reacting the endocyclic amine with an electrophile, such as an alkyl halide or sulfonate, an aralkyl halide or sulfonate, a heteroaralkyl halide or sulfonate, a cycloalkyl halide or sulfonate, a cycloalkylalkyl halide or sulfonate, a heterocyclyl halide or sulfonate, or a heterocyclylalkyl halide or sulfonate. Alternatively, step G may be performed by reductive alkylation, e.g., reacting the endocyclic amine with an appropriately substituted aldehyde in the presence of a reducing agent, such as sodium borohydride.

In certain embodiments, step E may be performed using reductive alkylation or by reacting the exocyclic amine with an electrophile, such as a halide or sulfonate.

In certain embodiments, step F may be performed by reacting an ester, thioester, or xanthate with a compound having the formula, for example, of $HNJ_2N(R_9)_2$ or $HXLR_4$, e.g., in the presence of a Lewis acid, at an elevated temperature, etc. In other embodiments, step F may be performed by reacting a carboxylic acid with an activating agent, such as a carbodiimide (e.g., diisopropylcarbodiimide, dicyclohexylcarbodiimide, 1-(3-dimethylaminopropyl)-3-ethylcarbodiimide, etc.), a phosphorous-based reagent (such as BOP—Cl, PyBROP, etc.), oxalyl chloride, phosgene, triphosgene, or any other reagent that reacts with a carboxylic acid group resulting in a reactive intermediate having an increased susceptibility, relative to the carboxylic acid, towards coupling with a nucleophile. Other techniques for coupling a nucleophile with a carboxylic acid or derivative thereof (such as an ester, thioester, etc.) are well known in the art and may be substituted for those specifically enumerated here.

In certain embodiments, Y and Z are O.

In certain embodiments, $R_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, $XLR_4$, taken together, include a cyclic amine, such as a piperazine, a morpholine, a piperidine, a pyrrolidine, etc.

In certain embodiments, L attached to $R_1$ represents O, S, or $NR_8$, such as NH.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group.

In certain embodiments, M is absent.

In certain embodiments, X is not NH. In certain embodiments, X is included in a ring, or, taken together with —C(=Y)—, represents a tertiary amide.

In certain embodiments, $NJ_2N$, taken together, represent a cyclic diamine, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring which comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

IV. Exemplary Applications of Method and Compositions

Another aspect of the present invention relates to a method of modulating a differentiated state, survival, and/or proliferation of a cell having a ptc loss-of-function, hedgehog gain-of-function, or smoothened gain-of-function, by contacting the cells with a hedgehog antagonist according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The hedgehog antagonist, whether inductive or anti-inductive with respect to proliferation or differentiation of a given tissue, can be, as appropriate, any of the preparations described above.

For example, the present method is applicable to cell culture techniques wherein, whether for genetic or biochemical reasons, the cells have a ptc loss-of-function, hedgehog gain-of-function, or smoothened gain-of-function phenotype. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a hedgehog antagonist of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be affected by contact with hedgehog antagonists of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a hedgehog antagonist.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6–8, more preferably close to pH 7, even more particularly about pH 7.4. Cells should be cultured at a temperature close to physiological temperature, preferably between 30° C.–40° C., more preferably between 32° C.–38° C., and most preferably between 35° C.–37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070–1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3–4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3–10 days in vitro, the proliferating clusters (neurospheres) are fed every 2–7 days, and more particularly every 2–4 days by gentle centrifugation and resuspension in medium containing growth factor.

After 6–7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a hedgehog antagonist.

To further illustrate other uses of the subject hedgehog antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog antagonists employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The hedgehog antagonists can be used alone, or can be used in combination with other neurotrophic factors which act to more particularly enhance a particular differentiation fate of the neuronal progenitor cell.

In addition to the implantation of cells cultured in the presence of the subject hedgehog antagonists, yet another aspect of the present invention concerns the therapeutic application of a hedgehog antagonist to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubulated by use of a prosthetic device, hedgehog antagonists can be added to the prosthetic device to regulate the rate of growth and regeneration of the dendridic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the hedgehog antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog antagonists can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog antagonists of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog antagonists can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising hedgehog antagonists can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) Curr Biol 7:801–4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject hedgehog antagonists can be used to control or regulate the proliferation and/or differentiation of pancreatic tissue both in vivo and in vitro.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and smoothened signaling may be indicated in disease progression, the subject inhibitors, can be used to enhance regeneration of the tissue after antitumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearence of embryonal traits in mature β-cells can be observed. By utilizing the subject hedgehog antagonists, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) *Biochem Biophys Res Commun* 238:658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., basal cell carcinoma, medulloblastoma, meningioma, etc.), tumors evidenced in pct knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising hedgehog antagonists can be used in the in vitro generation of skeletal tissue, such as from skeletogenic stem cells, as well as the in vivo treatment of skeletal tissue deficiencies. The present invention particularly contemplates the use of hedgehog antagonists to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog antagonist, particularly an antagonist selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject antagonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed*

*Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog antagonist during certain stages of the culturing process in order to manage the rate of differentiation of chondrocytes and the formation of hypertrophic chrondrocytes in the culture.

In another embodiment, the implanted device is treated with a hedgehog antagonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog antagonists of the present invention can be employed as part of a method for regulating the rate of bone loss in a subject. For example, preparations comprising hedgehog antagonists can be employed, for example, to control endochondral ossification in the formation of a "model" for ossification.

In yet another embodiment of the present invention, a hedgehog antagonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a preferred embodiment, the hedgehog antagonist can be used as a contraceptive. In similar fashion, hedgehog antagonists of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a hedgehog antagonist effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use. of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g. resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of an hedgehog antagonist can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of hedgehog antagonists can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing an hedgehog antagonist preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog protein results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin,. a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, hedgehog antagonists can be used to manage hirsutism, a disorder marked by abnormal hairiness. The subject method can also provide a process for extending the duration of depilation.

Moreover, because a hedgehog antagonist will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, hedgehog antagonists can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concommitant relief of the inhibition of follicle cell proliferation.

The subject method can also be used in the treatment of folliculitis, such as folliculitis decalvans, folliculitis ulerythematosa reticulata or keloid folliculitis. For example, a cosmetic prepration of an hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflarnmatory or non-inflammatory. components. To illustrate, therapeutic preparations of a hedgehog antagonist, e.g., which promotes quiescense or differentiation can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activiation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a hedgehog antagonist composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale,* a yeast. Treatment with an antiproliferative hedgehog antagonist, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaley, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

For example, it is contemplated that the subject method could be used to inhibit angiogenesis. Hedgehog is known to stimulate angiogenesis. Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The ptc-1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of ptc-1 expression. In addition, hedgehog proteins stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels.

Given that hedgehog promotes angiogenesis, hedgehog antagonists are expected to act as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases caused by, supported by or associated with angiogenesis include ocular neovascular disease, age-related macular degeneration, diabetic retinopathy, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Stevens Johnson disease, periphigoid radial keratotomy, corneal graph rejection, rheumatoid arthritis, osteoarthritis chronic inflammation (eg., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important is in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is anticipated that the invention will be useful for the treatment and/or prevention of respiratory distress syndrome or other disorders resulting from inappropriate lung surface tension. Respiratory distress syndrome results from insufficient surfactant in the alveolae of the lungs. The lungs of vertebrates contain surfactant, a complex mixture of lipids and protein which causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

Lung tissue of premature infants shows high activity of the hedgehog signaling pathway. Inhibition of this pathway using hedgehog antagonists increases the formation of lamellar bodies and increases the expression of genes involved in surfactant biosynthesis. Lamellar bodies are subcellular structures associated with surfactant biosynthesis. For these reasons, treatment of premature infants with a hedgehog antagonist should stimulate surfactant biosynthesis and ameliorate RDS. In cases where adult RDS is associated with hedgehog pathway activation, treatment with hedgehog antagonists should also be effective.

It is further contemplated that the use of hedgehog antagonists may be specifically targeted to disorders where the affected tissue and/or cells evince high hedgehog pathway activation. Expression of gli genes is activated by the hedgehog signaling pathway, including gli-1, gli-2 and gli-3. gli-1 expression is most consistently correlated with hedgehog signaling activity across a wide range of tissues and disorders, while gli-3 is somewhat less so. The gli genes encode transcription factors that activate expression of many genes needed to elicit the full effects of hedgehog signaling. However, the Gli-3 transcription factor can also act as a repressor of hedgehog effector genes, and therefore, expression of gli-3 can cause a decreased effect of the hedgehog signaling pathway. Whether Gli-3 acts as a transcriptional activator or repressor depends on post-translational events, and therefore it is expected that methods for detecting the activating form (versus the repressing form) of Gli-3 protein would also be a reliable measure of hedgehog pathway activation. gli-2 gene expression is expected to provide a reliable marker for hedgehog pathway activation. The gli-1 gene is strongly expressed in a wide array of cancers, hyperplasias and immature lungs, and serves as a marker for the relative activation of the hedgehog pathway. In addition, tissues, such as immature lung, that have high gli gene expression are strongly affected by hedgehog inhibitors. Accordingly, it is contemplated that the detection of gli gene expression may be used as a powerful predictive tool to identify tissues and disorders that will particularly benefit from treatment with a hedgehog antagonist.

In preferred embodiments, gli-1 expression levels are detected, either by direct detection of the transcript or by detection of protein levels or activity. Transcripts may be detected using any of a wide range of techniques that depend primarily on hybridization of probes to the gli-1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE)(preferably compared against a standard wherein the position of the Gli proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify posttranscriptional modifications to proteins including proteolytic events, ubiquitination, phosphorylation, lipid modification etc. Gli activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to Gli binding sites on DNA.

In preferred embodiments, gli transcript levels are measured and diseased or disordered tissues showing abnormally high gli levels are treated with a hedgehog antagonist. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a hedgehog antagonist. In addition, there is substantial correlative evidence that cancers of urothelial cells (e.g., bladder cancer, other urogenital cancers) will also have elevated gli-1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high gli expression and would be particularly amenable to treatment with a hedgehog antagonist.

Expression of ptc-1 and ptc-2 is also activated by the hedgehog signaling pathway, but these genes are inferior to the gli genes as markers of hedgehog pathway activation. In certain tissues only one of ptc-1 or ptc-2 is expressed although the hedgehog pathway is highly active. For example, in testicular development, Indian hedgehog plays an important role and the hedgehog pathway is activated, but only ptc-2 is expressed. Accordingly, these genes are individually unreliable as markers for hedgehog pathway activation, although simultaneous measurement of both genes are contemplated as a useful indicator for tissues to be treated with a hedgehog antagonist.

Ailments which may be treated by the subject method are disorders specific to non-humans, such as mange.

In still another embodiment, the subject method can be used in the treatment of human cancers, particularly basal cell carcinomas and other tumors of epithelial tissues such as the skin. For example, hedgehog antagonists can be employed, in the subject method, as part of a treatment for basal cell nevus syndrome (BCNS), and other other human carcinomas, adenocarcinomas, sarcomas and the like.

In a preferred embodiment, the subject method is used as part of a treatment ot prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) *Science* 277:1109–13; Xie et al. (1997) *Cancer Res* 57:2369–72; Oro et al. (1997) *Science* 276:817–21; Xie et al. (1997) *Genes Chromosomes Cancer* 18:305–9; Stone et al. (1996) *Nature* 384:129–34; and Johnson et al. (1996) *Science* 272:1668–71.

The subject method can also be used to treatment patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations comprising hedgehog antagonists. The hedgehog antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active. substances is known in the art. Except insofar as any conventional media or agent is incompatible with the activity of the hedgehog antagonist, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the hedgehog antagonists suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a hedgehog antagonist at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutic effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The hedgehog antagonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by overcoming a ptc loss-of-function, hedgehog gain-of-function, or smoothened gain-of-function in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$ cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog antagonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the hedgehog antagonists in the proper medium. Absorption enhancers can also be used to increase the flux of the hedgehog antagonists across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

VI. Synthetic Schemes and Identification of Active Antagonists

The subjects steroidal alkaloids, and congeners thereof, can be prepared readily by employing the cross-coupling technologies of Suzuki, Stille, and the like. These coupling reactions are carried out under relatively mild conditions and tolerate a wide range of "spectator" functionality.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog antagonist lead compounds, as well as to refine the specificity, toxicity, and/or cytotoxic-kinetic profile of a lead compound. For instance, ptc, hedgehog, or smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject hedgehog antagonists. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lemer et al. PCT publication WO93/20242). Accordingly, a variety of libraries on the order of about 100 to 1,000,000 or more diversomers of the subject hedgehog antagonists can be synthesized and screened for particular activity or property.

In an exemplary embodiment, a library of candidate hedgehog antagonists diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate antagonists or a substituent of a synthetic intermediate. According to the Still et al. technique, the library is synthesized on a set of beads, each bead including a set of tags identifying the particular diversomer on that bead. The bead library can then be "plated" with ptc loss-of-function, hedgehog gain-of-function, or smoothened gain-of-function cells for which an hedgehog antagonist is sought. The diversomers can be released from the bead, e.g. by hydrolysis.

The structures of the compounds useful in the present invention lend themselves readily to efficient synthesis. The nature of the structures, as generally described by formulas I to IV, allows the assembly of such compounds using some combination of $R_1$, $R_2$, $R_3$, and $R_4$ moieties, as set forth above. For example, these subunits can be attached to the core ring through common acylation or alkylation reactions. The vast majority of such reactions, including those depicted in FIGS. 11, 12, 15, and 16 are both extremely mild and extremely reliable, and are thus perfectly suited for combinatorial chemistry. The facile nature of such a combinatorial approach towards the generation of a library of test compounds is apparent in the exemplary scheme below (P=protecting group), wherein the various groups of a compound according to the above formulae are linked combinatorially (e.g., using one of the methods described above). Even greater diversity may be attained by, for example, utilizing a range of reactive functionalities when appending a subunit, e.g., using a range of R—L—C(O)Cl, PO—Ar—L—NCO, PO—Ar—L—SO$_2$Cl, etc. when appending an $R_1$ subunit.

Many variations on the above and related pathways permit the synthesis of widely diverse libraries of compounds which may be tested as inhibitors of hedgehog function.

PREPARATION OF EXEMPLARY COMPOUNDS OF THE PRESENT INVENTION

A series of compounds conforming to the general structures disclosed herein were prepared and tested for biological activity (vide infra). A suitable core structure can be readily prepared from commercially available trans-4-hydroxy-L-proline as summarized in the scheme below:

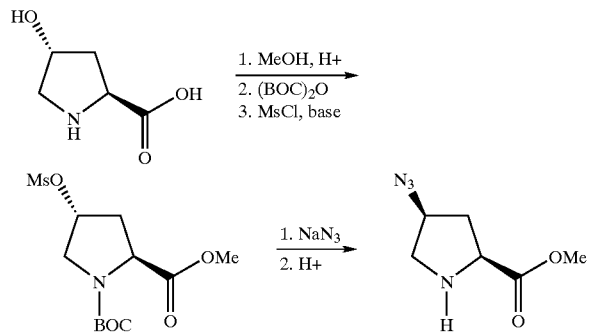

Trans-4-hydroxy-L-proline methyl ester hydrochloride

Acetyl chloride (249 mL, 3.47 mol) was added dropwise to methanol (2090 mL) with stirring and cooling to maintain the temperature below 30° C. After complete addition, stirring was continued for a further 60 min. before addition of trans-4-hydroxy-L-proline (325 g, 2.48 mol) as a solid. The reaction mixture was heated to reflux for 24 h, cooled to 0° C., and tert-butyl methyl ether (TBME, 5220 mL) was added slowly over 30 min. The precipitated solid was collected on a filter and washed with ice-cold TMBE (2×1 L). The product was dried at 40° C. overnight in a vacuum to yield 424 g of the desired ester.

Trans-1-(tert-butoxycarbonyl)-4-hydroxy-L-proline methyl ester

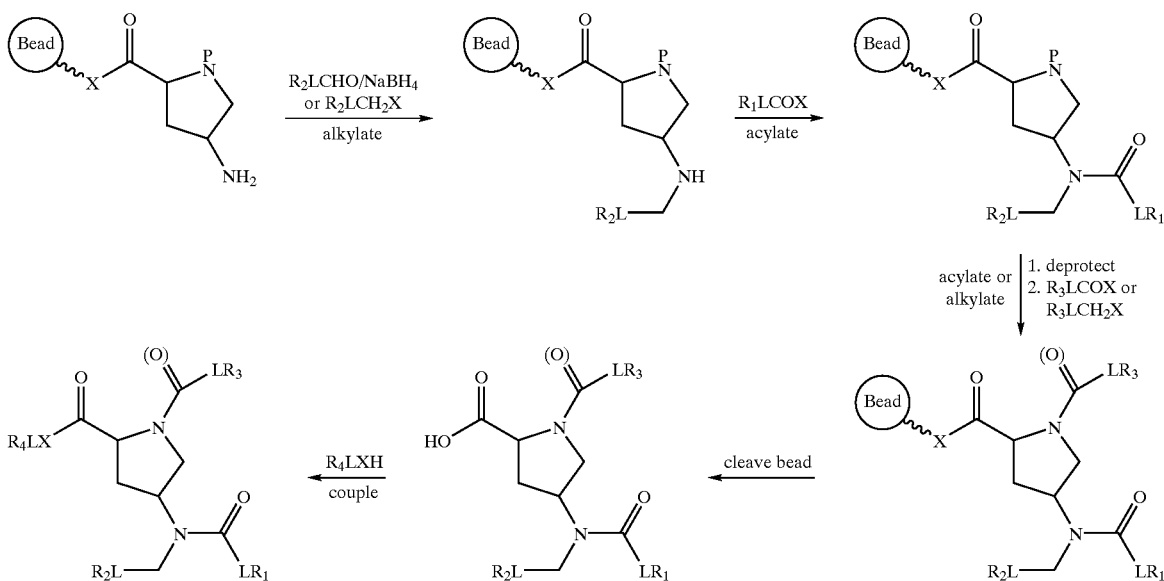

The product ester of the previous reaction (423 g, 2.32 mol) was suspended in dichloromethane (6.5 L). Under stirring and cooling, triethylamine (1019 mL, 7.32 mol) was added over 30 min., followed by di-tert-butyl dicarbonate (588 g, 2.70 mol) over 30 min. to maintain the internal temperature below 15° C. After complete addition, the mixture was stirred at room temperature for 3 hours, followed by addition of 1 M aqueous citric acid solution (650 mL). The mixture was stirred 1 hour, and the organic layer was separated, washed with 1 M aqueous $KHCO_3$ (920 mL), water (2×1 L), and dried over $MgSO_4$ in the presence of activated charcoal (15 g). The solvent was removed in vacuo and the residue purified by flash chromatography (2×1800 g silica gel, 3:1 to 2:1 hexane:EtOAc eluent) to give the desired carbarnate (489 g).

(4R)-1-(tert-butoxycarbonyl)-4-[(methylsulfonyl)oxy]-L-proline methyl ester

The carbamate above (478 g, 1.95 mol), N-diisopropylethylamine (DIPEA, 373 mL, 2.15 mol), and 4-dimethylaminopyridine (DMAP, 23.8 g, 0.195 mol) were dissolved in dichloromethane (7650 mL). Methanesulfonyl chloride (167 mL, 2.15 mol) in dichloromethane (950 mL) was added dropwise over 50 min. with cooling to maintain a temperature below 10° C. The mixture was stirred at −6° C. for 2 h, water (750 mL) was added, the mixture was stirred 15 min. more, and the layers were separated. The organic layer was washed with 1 M aqueous $KHCO_3$ (950 mL), 1 M aq. citric acid (2×950 mL), and water (750 mL) and dried over $MgSO_4$. The solvent was removed in vacuo and the residue crystallized with hexane (1.9 L). The crystalline mesylate was collected on a filter, washed with hexane (2×500 mL), and dried at 40° C. in vacuo to give 624 g of the product.

(4S)-1-(tert-butoxycarbonyl)-4-azido-L-proline methyl ester

A solution of the above mesylate (624 g, 1.93 mol) and sodium azide (716 g, 11.01 mol) in dimethylformamide (DMF, 3120 mL) was stirred for 22 h at 60° C., the solution was cooled to 0° C., water (3 L) was added over 40 min. to keep the temperature below 20° C., and EtOAC (3 L) was added. The mixture was stirred vigorously 20 min, the layers were separated, and the aqueous phase extracted with EtOAc (3 L). The combined organic layers were washed with water (750 mL), 0.1 M aq. HCl (400 mL), and water (750 mL), then dried over $MgSO_4$. The solvent was removed in vacuo and the residue purified by flash chromatography (2×1800 g silica gel, 2:1 hexane:EtOAc) to give the desired azide (516 g).

(4S)-4-azido-L-proline methyl ester hydrochloride

A saturated solution of HCl in dioxane (1940 mL) was prepared at 10–16° C., and a solution of the azide (523 g, 1.94 mmol) in dioxane (480 mL) was added dropwise with stirring and cooling over 30 min. to keep the temperature below 25° C. After complete addition, the reaction mixture was stirred at room temperature for 2 hours, TBME (2 L) was added, and the resulting mixture stirred at 0° C. for 1 hour. The precipitated solid was collected on filter paper, washed with TBME (4×500 mL), and dried at 40° C. in vacuo to give the desired hydrochloride salt (348 g).

Subject compounds can be prepared from the above core, or from related compounds or derivatives, using solution-phase or solid-phase techniques, as shown in the schemes below:

Scheme 1

Solution-Phase Route 1

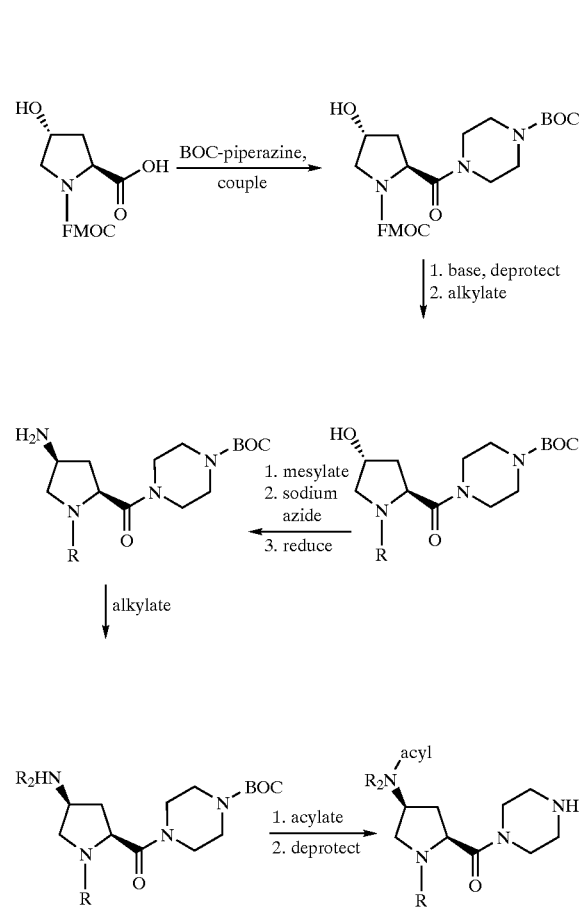

Scheme 2

Solution-Phase Route 2

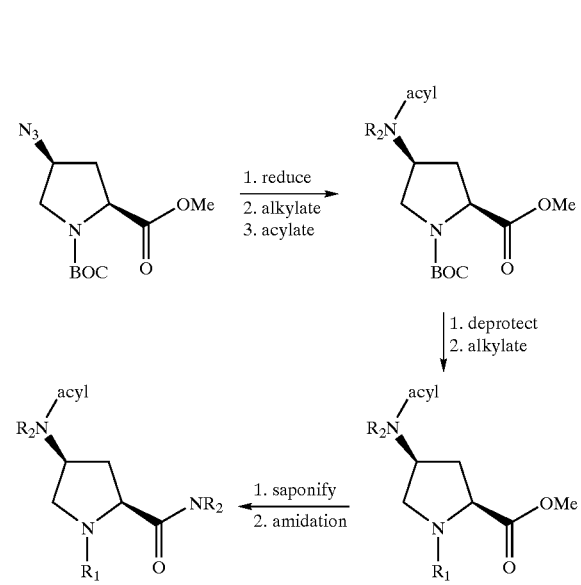

Scheme 3
Solid-Phase Route

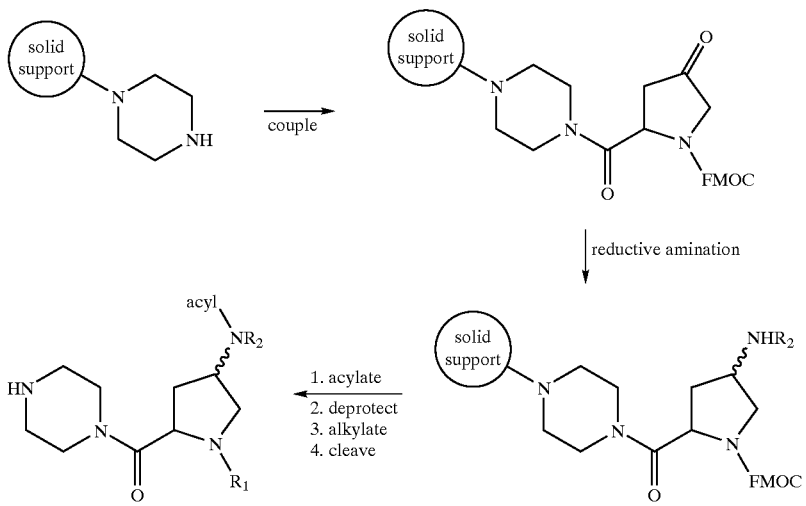

These routes, together with the exemplary solid-phase route, provide access to a wide range of compounds having different substituents and stereochemical relationships. One of ordinary skill in the art will appreciate that the use of piperazine in the above schemes is exemplary only, and other amines can be employed to obtain an even more diverse array of subject compounds. Similarly, the use of BOC, FMOC, and other protecting groups is exemplary only, and one of skill in the art can select other protecting groups suitable for the functional group and the subsequent reaction conditions without departing from the scope or spirit of the present invention. Furthermore, although the above schemes typically begin with the trans-hydroxy-L-proline compound, all isomers of this compound are commercially available, including cis/trans and D/L compounds, providing access to a wide range of diastereomerically pure intermediates and subject compounds. A trans-aminoproline core can be obtained from a trans-hydroxyproline starting material by forming an intermediate cis-bromoproline (by forming, for example, a triflate or mesylate of the hydroxyl and displacing the sulfonate with bromide ion), followed by a second displacement with azide, to provide net retention of the trans stereochemical relationship, as is well known in the art. Alternatively, diastereomeric mixtures may be prepared, as in the above Scheme 3, followed by an optional separation of the isomers.

b. Screening Assays

There are a variety of assays available for determining the ability of a compound to agonize ptc function or antagonize smoothened or hedgehog function, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are hedgehog antagonists.

In addition to cell-free assays, test compounds can also be tested in cell-based assays. In one embodiment, cell which have a ptc loss-of-function, hedgehog gain-of-function, or smoothened gain-of-function phenotype can be contacted with a test agent of interest, with the assay scoring for, e.g., inhibition of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are the patched gene (Hidalgo and Ingham, 1990 *Development* 110, 291–301; Marigo et al., 1996 ) and the vertebrate homologs of the drosophila cubitus interruptus gene, the GLI genes (Hui et al. (1994) *Dev Biol* 162:402–413). Patched gene expression has been shown to be induced in cells of the limb bud and the neural plate that are responsive to Shh. (Marigo et al. (1996) *PNAS* 93:9346–51; Marigo et al. (1996) *Development* 122:1225–1233). The Gli genes encode putative transcription factors having zinc finger DNA binding domains (Orenic et al. (1990) *Genes & Dev* 4:1053–1067; Kinzler et al. (1990) *Mol Cell Biol* 10:634–642). Transcription of the Gli gene has been reported to be upregulated in response to hedgehog in limb buds, while transcription of the Gli3 gene is downregulated in response to hedgehog induction (Marigo et al. (1996) *Development* 122:1225–1233). By selecting transcriptional regulatory sequences from such target genes, e.g., from patched or Gli genes, that are responsible for the up- or down-regulation of these genes in response to hedgehog signalling, and operatively linking such promoters to a reporter gene, one can derive a transcription based assay which is sensitive to the ability of a specific test compound to modify hedgehog-mediated signalling pathways. Expression of the reporter gene, thus, provides a valuable screening tool for the development of compounds that act as antagonists of hedgehog.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc loss-of-function, hedgehog gain-of-function, smoothened gain-of-function, or stimulation by SHH itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or antagonized the gain-of-function hedgehog or smoothened signal), e.g., the test compound is a potential hedgehog antagonist.

EXEMPLIFICATION

The invention now being generally described, it will be more readily understood by reference to the following examples which are included merely for purposes of illustration of certain aspects and embodiments of the present invention, and are not intended to limit the invention.

SYNTHESIS OF EXEMPLARY INHIBITORS

N-1-[(3R,5S)-1-(1,3-benzodioxol-5-ylmethyl)-5-(piperazinocarbonyl)tetrahydro-1H-3-pyrrolyl]-N-1-(4-methoxybenzyl)-3,3-dimethylbutanamide. "Trans-aminoproline"

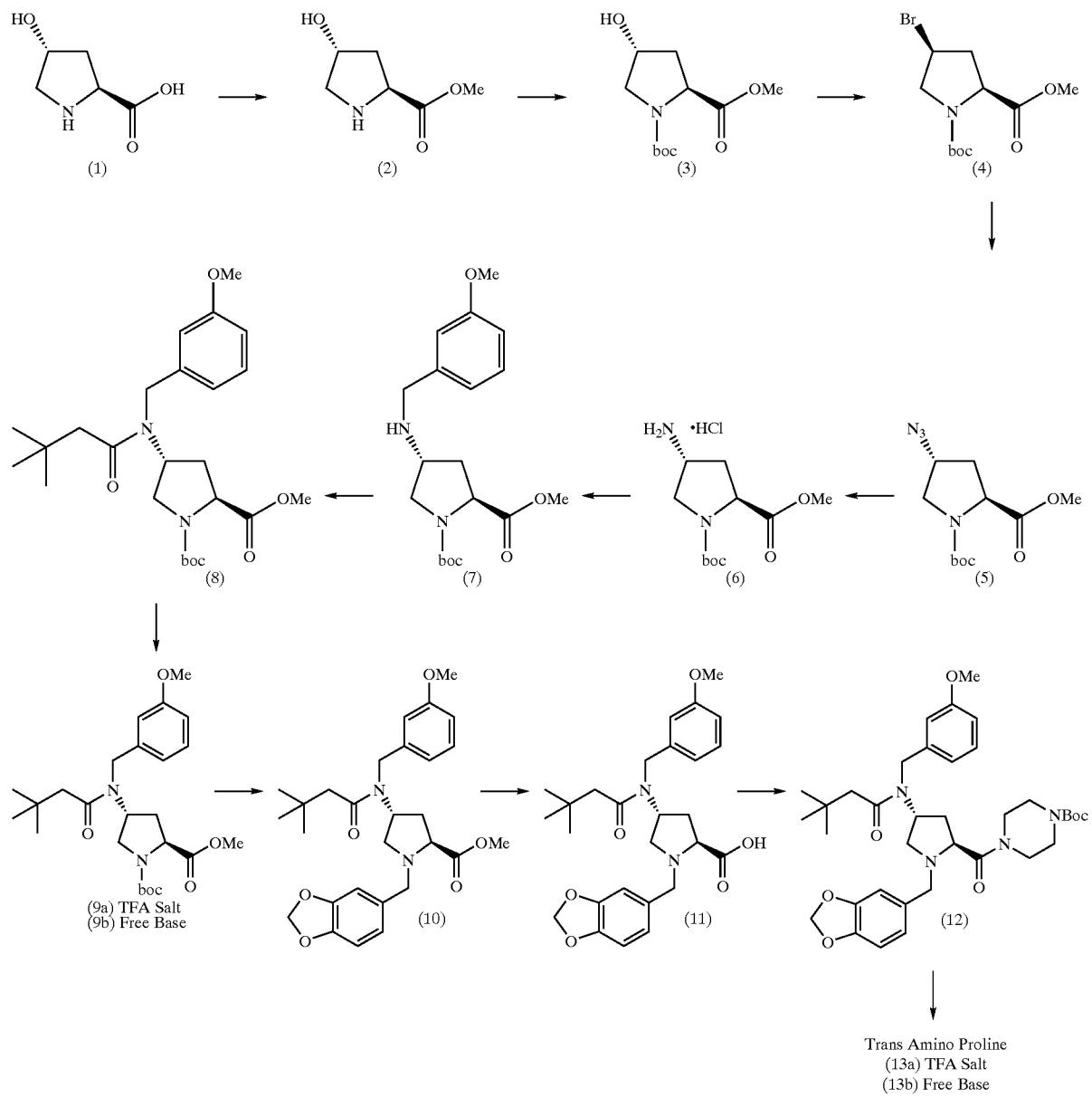

1-(tert-Butyl) 2-methyl(2S,4S)-4-bromotetrahydro-1H-1,2-pyrroledicarboxylate (4)

1-(tert-Butyl) 2-methyl(2S,4R)-4-hydroxytetrahydro-1H-1,2-pyrroledicarboxylate (3) (2.0 g, 8.15 mmol) was weighed into an oven-dried flask and azeotropically dried using toluene. Dichloromethane (16 mL) and carbon tetrabromide (10.81 g, 8.15 mmol) were added and the solution was stirred, cooled to 0° C. and treated with triphenylphosphine (8.5 g, 32.41 mmol). The mixture was stirred for 5 h at 0° C., then methanol (1.8 mL) was added and stirring was continued overnight at room temperature. The mixture was diluted with diethyl ether (80 ml) and the resulting suspension was filtered and washed with diethyl ether (30 ml). The solvents were combined and evaporated under reduced pressure and the crude product was purified by silica gel column chromatography eluting with hexane/ethyl acetate (19:1 to 4:1, v/v) to give the title bromide (4) (1.0 g, 40%) as a colourless oil:

$\delta_H$ (360 MHz; CDCl$_3$) 1.41 and 1.46 (2×s, 9H, rotamers), 2.38–2.46 (m, 1H), 2.75–2.87 (m, 1H), 3.67–3.74 (m, 1H), 3.76 (s, 3H), 3.96–4.07 (m, 1H) and 4.24–4.42 (m, 2H); LRMS (from LC-MS) (ES+) m/z 210 (100).

1-(tert-Butyl) 2-methyl(2S,4R)-4-azidotetrahydro-1H-1,2-pyrroledicarboxylate (5)

A dispersion of sodium azide (0.90 g, 13.84 mmol) and 1-(tert-butyl)-2-methyl (2S,4S)-4-bromotetrahydro-1H-1,2-pyrroledicarboxylate (4) (1.0 g, 3.24 mmol) in anhydrous dimethylformamide (32 mL) was heated for 64 h under an atmosphere of nitrogen. The mixture was cooled to room temperature, poured into ice-cold water and extracted with ethyl acetate. The organic extracts were combined, washed with water and brine, dried (MgSO$_4$) and evaporated under reduced pressure. The crude product was purified by silica gel column chromatography eluting with hexane-ethyl acetate (3:1 to 1:1, v/v) to give the title azide (5) (0.88 g, 93%) as a pale yellow oil:

$\delta_H$ (360 MHz; CDCl$_3$) 1.41 and 1.46 (2×s, 9H, rotamers), 2.13–2.20 (m, 1H), 2.27–2.38 (m, 1H), 3.45–3.49 and 3.57–3.60 (2×m, 1H, rotamers), 3.68–3.73 (m, 1H), 3.74–3.75 (2×s, 3H, rotamers), 4.15–4.23 (m, 1H) and 4.30–4.35 and 4.39–4.43 (2×m, 1H, rotamers); LRMS (from LC-MS) (ES+) m/z 171 [(M+H)$^+$—C$_5$H$_9$O$_2$] (100).

1-(tert-Butyl) 2-methyl(2S,4R)-4-ammoniotetrahydro-1H-1,2-pyrroledicarboxylate chloride (6)

Palladium on carbon (10%, 0.5 g) was added to a solution of 1-(tert-butyl)-2-methyl(2S,4R)-4-azidotetrahydro-1H-1,2-pyrroledicarboxylate (5) (0.81 g, 3.0 mmol) in 2% v/v hydrochloric acid in ethanol (8 mL). The reaction mixture was evacuated and purged with nitrogen (three times), then placed under an atmosphere of hydrogen and vigorously stirred at room temperature overnight. The mixture was filtered through a pad of Celite and evaporated under reduced pressure to give the crude product. This was triturated with diethyl ether at 0° C. and the resulting slurry was filtered, washed with ice-cold diethyl ether and dried under vacuum. The title salt (6) was obtained in quantitative yield:

$\delta_H$ (360 MHz; CD$_3$OD) 1.46 and 1.51 (2×s, 9H, rotamers), 2.35–2.47 (m, 2H), 3.50–3.55 (m, 1H), 3.74–3.86 [m, 4H, {containing at 3.79 and 3.80 (2×s, 3H, rotamers)}], 3.89–3.95 (m, 1H) and 4.46–4.50 (m, 1H); LRMS (from LC-MS) (ES+) m/z 210 (100).

1-(tert-Butyl) 2-methyl(2S,4R)-4-[3-methoxybenzyl)amino]tetrahydro-1H-1,2-pyrroledicarboxylate (7)

A solution of 1-(tert-butyl) 2-methyl(2S,4R)-4-ammoniotetrahydro-1H-1,2-pyrroledicarboxylate chloride (6) (0.83 g, 2.96 mmol) and 3-methoxybenzaldehyde (0.38 g, 2.8 mmol) in trimethyl orthoformate (8 mL) was stirred for 45 min at room temperature. The solution was treated slowly with sodium cyanoborohydride (0.28 g, 4.46 mmol) and the course of the reaction was monitored by TLC analysis. Once completed (~1.5 h), the reaction was quenched with saturated aqueous potassium hydrogensulfate solution and extracted with dichloromethane. The pH value of the aqueous phase was adjusted to 9 and back-extracted with dichloromethane. The combined organic extracts were dried (MgSO$_4$) and evaporated under reduced pressure to give the title amine (7) in quantitative yield:

$\delta_H$ (360 MHz; CDCl$_3$) 1.40 and 1.45 (2×s, 9H, rotamers), 2.07–2.19 (m, 2H), 3.18–3.23 and 3.32–3.36 (2×m, 1H), 3.43–3.53 (m, 1H), 3.70–3.74 [m, 4H, {containing at 3.72 and 3.73 (2×s, 3H, rotamers)}] 3.81 (s, 3H), 4.32–4.36 and 4.40–4.44 (2×m, 1H), 6.79–6.81 (m, 1H), 6.87–6.89 (m, 2H) and 7.24 (t, 1H); LRMS (from LC-MS) (ES+) m/z 265 [(M+H)$^+$—C$_5$H$_9$O$_2$] (100).

1-(tert-Butyl) 2-Methyl (2S,4R)-4-[(3,3-dimethylbutanoyl)(3-methoxybenzyl)amino]tetrahydro-1H-2-pyrrolecarboxylate (8)

A solution of 1-(tert-butyl)-2-methyl(2S,4R)-4-[3-methoxybenzyl)amino]tetrahydro-1H-1,2-pyrroledicarboxylate (7) (0.3 g, 0.82 mmol) and N,N-diisopropylethylamine (0.106 g, 0.82 mmol) in anhydrous dichloromethane (0.8 mL) was stirred at room temperature under an atmosphere of nitrogen. The solution was treated dropwise with tert-butylacetyl chloride (0.133 g, 0.99 mmol) and stirred overnight. The solvent was evaporated under reduced pressure and the residue was purified by silica gel column chromatography (hexane-ethyl acetate, 2:1, v/v) to give the title amide (8) (1.0 g, 40%) as a colourless oil:

$\delta_H$ (360 MHz; CDCl$_3$) 1.01 and 1.05 (2×s, 9H, rotamers), 1.37 and 1.41 (2×s, 9H, rotamers), 1.87–2.56 [m, 4H (containing at 2.16 (s, 2H)], 3.17–3.35 (m, 1H), 3.62–3.85 [m, 7H, {containing at 3.70 and 3.79 (2×s, 6H)}] 4.21–4.24 and 4.28–4.35 (2×m, 1H, rotamers), 4.40–4.58 (m, 2H), 4.73–4.95 and 5.03–5.21 (2×m, 1H, rotamers), 6.54–6.88 (m, 3H) and 7.19–7.31 (m, 1H); LRMS (from LC-MS) (ES+) m/z 363 (100).

(2S,4R)-4-[(3,3-dimethylbutanoyl)(3-methoxyanilino)]-2-(methoxycarbonyl)tetrahydro-1H-2-pyrrolium 2,2,2-trifluoroacetate (9a)

1-(tert-Butyl) 2-methyl(2S,4R)-4-[(3,3-dimethylbutanoyl)(3-methoxybenzyl)amino]-tetrahydro-1H-2-pyrrolecarboxylate (8) (0.01 g, 21.6 µmol) was added to a 30% solution of trifluoroacetic acid in dichloromethane (0.5 mL) at room temperature and stirred for 30 min. The solution was evaporated to dryness under reduced pressure to give the title pyrrolium salt (9a) in quantitative yield:

$\delta_H$ (360 MHz; CDCl$_3$) 1.05 (s, 9H), 2.38–2.57 (m, 4H), 3.59–3.68 (m, 2H), 3,75 (s, 3H), 3.79 (s, 3H), 4.09–4.15 (m, 1H), 4.52–4.63 (m, 2H), 4.78–4.94 (m, 1H), 6.66 (s, 1H), 6.70 (d, 1H), 6.86–6.88 (dd, 1H) and 7.31 (t, 1H).

Methyl (2S,4R)-1-(1,3-benzodioxol-5-ylmethyl)-4-[(3,3-dimethylbutanoyl)(3-methoxybenzyl)amino]tetrahydro-1H-2-pyrrolecarboxylate (10)

1-(tert-Butyl) 2-methyl(2S,4R)-4-[(3,3-dimethylbutanoyl)(3-methoxybenzyl)amino]-tetrahydro-1H-2-pyrrolecarboxylate (8) (0.15 g, 0.32 mmol) was added to a solution of 30% v/v trifluoroacetic acid in dichloromethane (3 mL) at room temperature. The mixture was stirred for 30 min and evaporated to dryness under vacuum. The residue was partitioned between dichloromethane and saturated aqueous potassium carbonate and shaken vigorously for 5 mins. The organic layer was separated, dried (MgSO$_4$) and evaporated under reduced pressure to give 140 mg of crude methyl (2S,4R)-4-[(3,3-dimethylbutanoyl)-3-methoxyanilino]tetrahydro-1H-2-pyrrolecarboxylate (9b) which was used in the following reaction without further purification.

A solution of the crude amine (9b) (140 mg) prepared above, piperonal (74 mg, 0.49 mmol) and glacial acetic acid (2 drops) in 1,2-dichloroethane (0.5 mL) was stirred for 30 min at room temperature. 95% Sodium cyanoborohydride (32 mg, 0.48 mmol) was added in small portions and stirring was continued for 1 h. The reaction was quenched with saturated aqueous sodium bicarbonate solution (2 mL), extracted with dichloromethane, dried (MgSO$_4$) and evaporated under reduced pressure. The residue was purified by silica gel column chromatography eluting with dichloromethane-ethyl acetate (90:10–75:25) to give the title pyrrole (10) (115 mg, 71.4%) as a pale yellow oil:

$\delta_H$ (360 MHz; CDCl$_3$) 0.98–1.08 (m, 9H), 2.09–2.59 [m, 4H, {containing at 2.13 (s, 2H)}], 2.96–3.07 (m, 1H), 3.47–3.85 (m, 1H), 4.46–4.63 (m, 1H), 4.83–4.94 (m, 1H), 5.92–5.95 (m, 2H), 6.63–6.89 (m, 6H) and 7.15–7.34 (m, 1H); LRMS (from LC-MS) (ES+) m/z 497 [(M+H)$^+$] (100).

(2S,4R)-1-(1,3-benzodioxol-5-ylmethyl)-4-[(3,3-dimethylbutanoyl)(3-methoxybenzyl)amino]tetrahydro-1H-2-pyrrolecarboxylic acid (11)

Lithium hydroxide monohydrate (17 mg, 0.405 mmol) was added to a solution of methyl(2S,4R)-1-(1,3-benzodioxol-5-ylmethyl)-4-[(3,3-dimethylbutanoyl)(3-methoxybenzyl)amino]tetrahydro-1H-2-pyrrolecarboxylate (10) (100 mg, 0.20 mmol) in 66% v/v methanol in water (1.0 mL). The mixture was stirred overnight at room temperature, then the solvent was removed under reduced pressure and the residue partitioned between dichloromethane (1.0 mL) and water (1.0 ml). The aqueous phase was acidified with 1.0 M aqueous citric acid and the two layers were vigorously stirred for 10 min at room temperature. The layers were separated and the aqueous layer was back-extracted with dichloromethane. The combined dichloromethane extracts were dried (MgSO$_4$) and evaporated under reduced pressure to give the title acid (11) (70 mg, 72%) as an off-white solid:

$\delta_H$ (360 MHz; CDCl$_3$) 1.00 and 1.03 (2×s, 9H, rotamers), 2.17–2.39 (m, 3H), 2.62–2.71 (m, 1H), 3.28–3.34 (m, 1H), 3.47–3.56 (m, 1H), 3.76 (m, 3H), 3.96–4.13 (m, 1H), 4.21–4.26 (m, 2H), 4.36–4.58 (m, 3H), 5.93 (d, 2H), 6.62–6.90 (m, 6H) and 7.21–7.25 (m, 1H); LRMS (from LC-MS) (ES+) m/z 483 [(M+H)$^+$] (1 00).

tert-Butyl 4-({(2S,4R)-1-(1,3-benzodioxol-5-ylmethyl)-4-[(3,3-dimethylbutanoyl)-3-methoxyanilino]tetrahydro-1H-2-pyrrolyl}carbonyl)-1-piperazinecarboxylate (12)

A mixture of (2S,4R)-1-(1,3-benzodioxol-5-ylmethyl)-4-[(3,3-dimethylbutanoyl)(3-methoxybenzyl)amino]tetrahydro-1H-2-pyrrolecarboxylic acid (11) (60 mg, 0.12 mmol), O-benzotriazol-1-yl-N,N,N',N'-tetramethyluronium tetrafluoroborate (48 mg, 0.15 mmol) and N,N-diisopropylethylamine (54 μL, 0.31 mmol) in dimethylformamide (1 mL) was stirred at room temperature for 1.5 h. The mixture was diluted with water and extracted with ethyl acetate. The aqueous. phase was back-extracted with ethyl acetate and the combined extracts were dried (MgSO$_4$) and evaporated to dryness under reduced pressure. The residue was partially purified by silica gel column chromatography eluting with 100% dichloromethane, dichloromethane/ethyl acetate (4:1, v/v) and 100% ethyl acetate to give the crude product, contaminated with N,N-dimethylformamide. Dichloromethane was added and the resulting solution was washed with water. The aqueous layer was back extracted with dichloromethane and the combined organic extracts were dried (MgSO$_4$) and evaporated under reduced pressure to give the title piperazine (12) (33.1 mg, 41%):

LRMS (from LC-MS) (ES+) m/z 651 [(M+H)$^+$] (100).

N1-[(3R,5S)-1-(1,3-benzodioxol-5-ylmethyl)-5-(piperazinocarbonyl)tetrahydro-1H-3-pyrroliumyl]-N1-(3-methoxybenzyl)-3,3-dimethylbutanamide 2,2,2-trifluoroacetate (13a).

A solution of tert-butyl 4-({(2S,4R)-1-(1,3-benzodioxol-5-ylmethyl)-4-[(3,3-dimethylbutanoyl)-3-methoxyanilino]tetrahydro-1H-2-pyrrolyl}carbonyl)-1-piperazinecarboxylate (12) (24 mg, 36.9 μmol) in dichloromethane (0.8 mL) was treated with trifluoroacetic acid (0.1 mL, 1.3 mmol). The mixture was stirred at room temperature and the course of the reaction was monitored by TLC analysis. Once completed, the solvent was evaporated under reduced pressure to give the title trifluoroacetate salt (13a) in quantitative yield. This salt was used in the following experiment without further purification:

LRMS (from LC-MS) (ES+) m/z 551 [(M+H)$^+$] (100).

N1-[(3R,5S)-1-(1,3-benzodioxol-5-ylmethyl)-5-(piperazinocarbonyl)tetrahydro-1H-3-pyrrolyl]-N1-(4-methoxybenzyl)-3,3-dimethylbutanamide (13b)

A biphasic mixture of dichloromethane (0.8 mL) and water (0.8 mL) containing 26 mg of crude N1-[(3R,5S)-1-(1,3-benzodioxol-5-ylmethyl)-5-(piperazinocarbonyl)tetrahydro-1H-3-pyrroliumyl]-N1-(3-methoxybenzyl)-3,3-dimethylbutanamide 2,2,2-trifluoroacetate (13a) was vigorously stirred and treated dropwise with 2.0 M aqueous sodium hydroxide solution until the pH value of the aqueous phase was adjusted to 12. The layers were separated and the aqueous layer was extracted with dichloromethane (2×1 mL). The organic extracts were combined, dried (MgSO$_4$) and evaporated under reduced pressure to give the title piperazine (13b) (12.7 mg, 59%):

LRMS (from LC-MS) (ES+) m/z 551 [(M+H)⁺] (100).

N1-[(3S,5S)-1-(1,3-benzodioxol-5-ylmethyl)-5-(piperazinocarbonyl)tetrahydro-1H-3-pyrrolyl]-N1-(4-methoxybenzyl)-3,3-dimethylbutanamide. "Cis-aminoproline"

1-(tert-Butyl) 2-methyl(2S,4S)-4-ammoniotetrahydro-1H-1,2-pyrroledicarboxylate chloride (16)

ether at 0° C. The resulting slurry was filtered, washed with ice-cold tert-butyl methyl ether and dried under vacuum to give the title hydrochloride salt (16) (0.74 g, 71%) as a white solid:

$\delta_H$ (360 MHz; $D_2O$) 1.21 and 1.26 (2×s, 9H, rotamers), 1.85–2.03 (m, 1H), 2.52–2.65 (m, 1H), 3.29–3.48 (m, 1H), 3.58–3.83 9(m, 5H) and 4.14–4.34 (m, 1H); LRMS (from LC-MS) (ES+) m/z 189 (100).

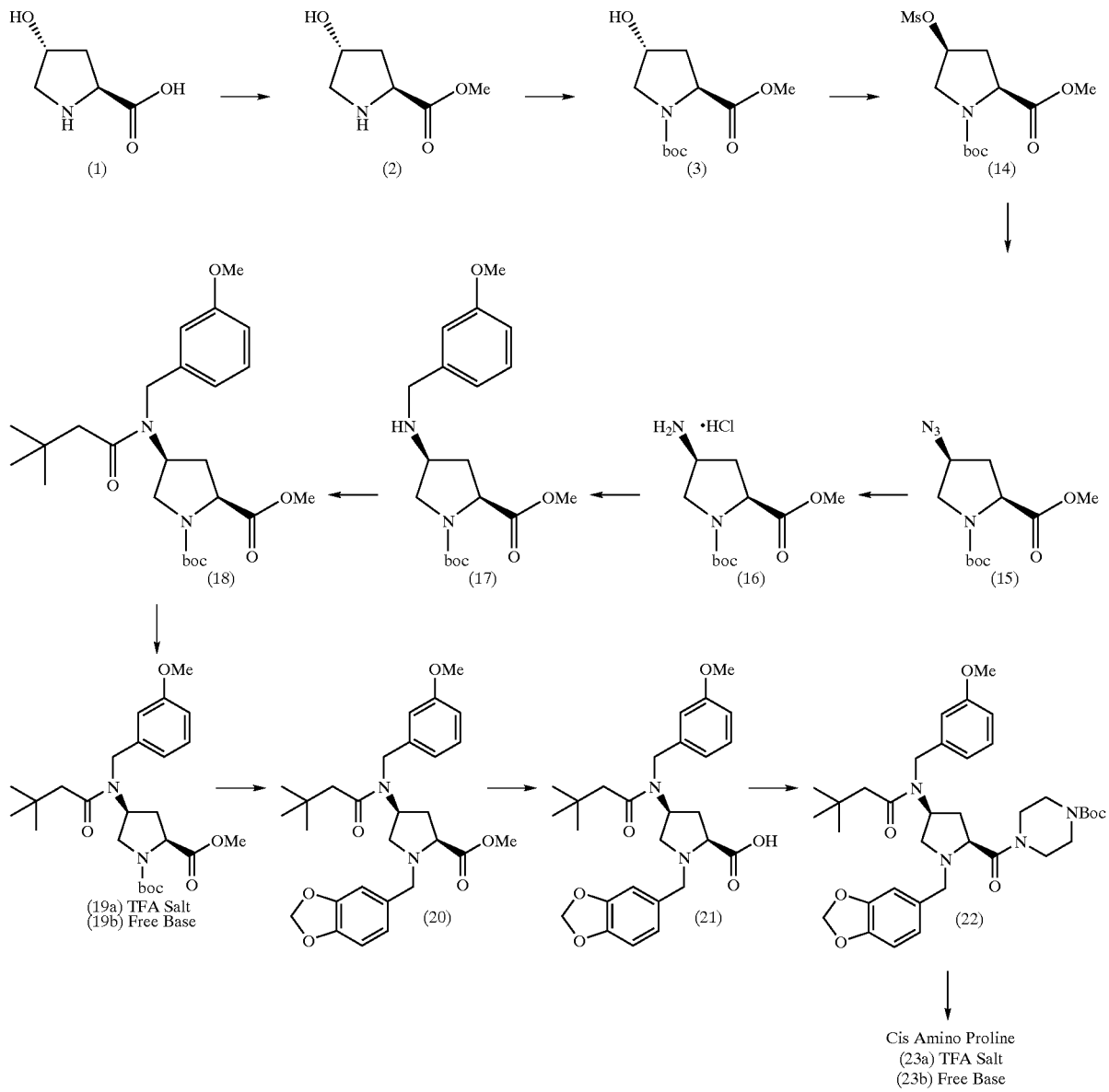

Cis Amino Proline
(23a) TFA Salt
(23b) Free Base

A suspension of palladium on carbon (10%, 0.25 g) and 1-(tert-butyl)-2-methyl (2S,4S)-4-azidotetrahydro-1H-1,2-pyrroledicarboxylate (15) (1.00 g, 3.7 mmol) in a degassed solution of 2% v/v hydrochloric acid in ethanol (10 mL) was vigorously stirred at room temperature under an atmosphere of hydrogen (1 atm). After stirring overnight, the mixture was filtered through a pad of Celite and washed thoroughly with ethanol. The filtrate was evaporated under reduced pressure and the residue was triturated with tert-butyl methyl 1-(tert-Butyl) 2-methyl(2S,4S)-4-[3-methoxybenzyl)amino]tetrahydro-1H-1,2-pyrroledicarboxylate (17)

A solution of 1-(tert-butyl) 2-methyl(2S,4S)-4-ammoniotetrahydro-1H-1,2-pyrroledicarboxylate chloride (16) (3.00 g, 10.70 mmol) and 3-methoxybenzaldehyde (1.30 mL, 10.7 mmol) in trimethyl orthoformate (8 mL) was stirred for 45 min at room temperature. Sodium triacetoxyborohydride (2.26 g, 10.70 mmol) was added to the solution in small portions over 30 mins and the course of the reaction was monitored by TLC analysis. Once completed (about 30 min), the reaction was quenched with saturated aqueous sodium hydrogencarbonate solution (15 mL) and extracted with ethyl acetate (15 mL). The organic extract was washed with saturated aqueous sodium hydrogencarbonate solution (2×15 mL), dried (MgSO$_4$) and evaporated under reduced pressure. The residue was purified by flash column chromatography on silica gel using 100% dichloromethane and then 100% ethyl acetate as eluents to give the title amine (17) (2.48 g, 64%) as a yellow oil:

1-(tert-Butyl) 2-Methyl (2S,4S)-4-[(3,3-dimethylbutanoyl)(3-methoxybenzyl)amino] tetrahydro-1H-2-pyrrolecarboxylate (18)

A stirred solution of 1-(tert-butyl) 2-methyl(2S,4S)-4-[3-methoxybenzyl)amino]tetrahydro-1H-1,2-pyrroledicarboxylate (17) (1.37 g, 3.76 mmol) and triethylamine (0.63 mL, 4.52 mmol) in anhydrous dichloromethane (14 mL) was treated dropwise with tert-butylacetyl chloride (0.53 mL, 3.82 mmol). After stirring overnight at room temperature, the mixture was diluted with dichloromethane (50 mL) and washed with 1.0 M aqueous citric acid solution (2×50 mL). The layers were separated and the aqueous layers were back-extracted with dichloromethane (25 mL). The combined organic layers were washed with saturated aqueous sodium hydrogencarbonate solution, dried (MgSO$_4$) and evaporated under reduced pressure. The residue was purified by silica gel column chromatography (hexane/ethyl acetate, 2:1, v/v) to give the title amide (18) (1.5 g, 86%) as a pale yellow oil:

$\delta_H$ (360 MHz; CDCl$_3$) 1.00 and 1.06 (2×s, 9H, rotamers), 1.38 and 1.42 (2×s, 9H, rotamers), 1.81–1.93 (m, 1H), 2.15 (s, 2H) 2.30–2.51 (m, 1H), 3.18–3.25 (m, 1H), 3.62–3.85 [m, 4H, {containing at 3.69 (s, 3H)}], 3.78 (m, 3H), 4.15–4.25 (m, 1H), 4.45–4.61 (m, 2H), 5.10–5.23 (m, 1H), 6.64–6.82 (m, 3H) and 7.13–7.31 (m, 1H); LRMS (from LC-MS) (ES+) m/z 363 (100).

(2S,4S)-4-[(3,3-dimethylbutanoyl)(3-methoxyanilino)]-2-(methoxycarbonyl)tetrahydro-1H-2-pyrrolium 2,2,2-trifluoroacetate (19a)

1-(tert-Butyl) 2-methyl(2S,4S)-4-[(3,3-dimethylbutanoyl)(3-methoxybenzyl)amino]-tetrahydro-1H-2-pyrrolecarboxylate (18) (524 mg, 1.13 mmol) was added to a 21% v/v solution of trifluoroacetic acid in dichloromethane (6.6 mL) at room temperature. The mixture was stirred for 50 min and then evaporated to dryness under reduced pressure to give 0.98 g of a mixture of the title pyrrolium salt (19a) and trifluoroacetic acid:

$\delta_H$ (360 MHz; CDCl$_3$) 1.08 (s, 9H), 2.34–2.42 (m, 1H), 2.47 (s, 3H), 2.63–2.72 (m, 1H), 3.61–3.71 (m, 2H), 3.82 (s, 3H), 3.83 (s, 3H), 4.07–4.14 (m, 1H), 4.43–4.54 (m, 1H), 4.57–4.67 (m, 2H), 6.68–6.74 (m, 2H), 6.90–6.93 (dd, 1H) and 7.34 (t, 1H).

Methyl (2S,4S)-1-(1,3-benzodioxol-5-ylmethyl)-4-[(3,3-dimethylbutanoyl)(3-methoxybenzyl)amino] tetrahydro-1H-2-pyrrolecarboxylate (20)

1-(tert-Butyl) 2-methyl(2S,4S)-4-[(3,3-dimethylbutanoyl)(3-methoxybenzyl)amino]-tetrahydro-1H-2-pyrrolecarboxylate (18) (138 mg, 0.38 mmol) was added to a solution of 30% v/v trifluoroacetic acid in dichloromethane (3 mL) at room temperature. The mixture was stirred for 30 min and evaporated to dryness under reduced pressure. The residue was partitioned between dichloromethane and saturated aqueous potassium carbonate and shaken vigorously for 5 mins. The organic layer was separated, dried (MgSO$_4$) and evaporated under reduced pressure to give 140 mg of crude methyl(2S,4R)-4-[(3,3-dimethylbutanoyl)-3-methoxyanilino]tetrahydro-1H-2-pyrrolecarboxylate (19b), which was used in the following reaction without further purification.

A solution of methyl(2S,4S)-4-[(3,3-dimethylbutanoyl)(3-methoxybenzyl)amino]tetrahydro-1H-2-pyrrolecarboxylate (19b) (138 mg, 0.38 mmol), piperonal (58 mg, 0.39 mmol) and glacial acetic acid (225 µL, 3.93 mmol) in tetrahydrofuran (2.8 mL) was stirred for 30 min at room temperature. 95% Sodium cyanoborohydride (125 mg, 1.88 mmol) was added in small portions and stirring was continued for 45 min at the same temperature. After dilution with ethyl acetate (5 mL), the reaction mixture was washed with saturated aqueous sodium hydrogencarbonate solution (2×5 mL) and brine (5 mL), dried (MgSO$_4$) and evaporated under reduced pressure. The residue was purified by silica gel column chromatography eluting with 100% dichloromethane and dichloromethane-ethylacetate (4:1, v/v) to give the title pyrrole (20):

$\delta_H$ (360 MHz; CDCl$_3$) 0.89 and 0.99 (2×s, 9H, rotamers), 1.65–1.79 (m, 1H), 1.87–2.11 [m, 3H, {containing at 1.94 (s, 2H)}], 2.21–2.66 (m, 2H), 3.04–3.15 (m, 2H), 3.56 (s, 3H), 3.67–3.74 [m, 4H, {containing at 3.67 (s, 3H)}], 4.43–4.64 (m, 2H), 4.74–4.92 (m, 1H), 5.10–5.14 (m, 1H), 5.74–5.88 (m, 2H), 6.49–6.78 (m, 6H) and 7.02–1.10 (m, 1H); LRMS (from LC-MS) (ES+) m/z 497 [(M+H)$^+$] (100).

(2S,4S)-1-(1,3-benzodioxol-5-ylmethyl)-4-[(3,3-dimethylbutanoyl)(3-methoxybenzyl)amino] tetrahydro-1H-2-pyrrolecarboxylic acid (21)

Lithium hydroxide monohydrate (17 mg, 0.405 mmol) was added to a solution of methyl(2S,4S)-1-(1,3-benzodioxol-5-ylmethyl)-4-[(3,3-dimethylbutanoyl)(3-methoxybenzyl)amino]tetrahydro-1H-2-pyrrolecarboxylate (20) (100 mg, 0.20 mmol) in 66% v/v methanol in water (1.0 mL). The mixture was stirred overnight at room temperature, then the solvent was removed under reduced pressure and the residue partitioned between dichloromethane (1.0 mL) and water (1.0 ml). The aqueous phase was acidified with 1.0 M aqueous citric acid solution and the two layers were vigorously stirred for 10 min at room temperature. The layers were separated and the aqueous layer was back-extracted with dichloromethane. The combined dichloromethane extracts were dried (MgSO$_4$) and evaporated under reduced pressure. The residue was purified by flash column chromatography on silica gel using dichloromethane/ethyl acetate (1:1, v/v) and then dichloromethane/methanol (9:1, v/v) as eluents to give the title acid (21) (88 mg, 91%) as an off-white solid:

$\delta_H$ (360 MHz; CDCl$_3$) 0.95 (s, 9H), 2.18 [m, 3H, {containing at 2.18 (s, 2H)}], 2.62–2.87 (m, 1H), 3.17–3.28 (m, 1H), 3.42–3.47 (m, 1H), 3.73 (m, 3H), 3.82–3.93 (m, 1H), 3.94–4.60 (m, 1H), 4.41–4.65 (m, 4H), 5.90–5.94 (m, 2H), 6.63–6.93 (m, 6H) and 7.21–7.25 (m, 1H); LRMS (from LC-MS) (ES+) m/z 483 [(M+H)$^+$] (100).

tert-Butyl 4-({(2S,4S)-1-(1,3-benzodioxol-5-ylmethyl)-4-[(3,3-dimethylbutanoyl)-3-methoxyanilino]tetrahydro-1H-2-pyrrolyl}carbonyl)-1-piperazinecarboxylate (22)

A mixture of (2S,4S)-1-(1,3-benzodioxol-5-ylmethyl)-4-[(3,3-dimethylbutanoyl)(3-methoxybenzyl)amino] tetrahydro-1H-2-pyrrolecarboxylic acid (21) (96.5 mg, 0.20 mmol), O-benzotriazol-1-yl-N,N,N',N'-tetramethyluronium tetrafluoroborate (77 mg, 0.24 mmol) and N,N-diisopropylethylamine (87 μL, 0.50 mmol) in dimethylformamide (1 mL) was stirred for 1.5 h at room temperature. The mixture was diluted with water and extracted with ethyl acetate. The aqueous phase was back-extracted with ethyl acetate and the combined organic extracts were dried (MgSO$_4$) and evaporated to dryness under reduced pressure. The residue was purified by silica gel column chromatography using hexane-ethyl acetate (1:1, v/v) and then 100% ethyl acetate as eluents to give the title piperazine (22) (89 mg, 68%):

$\delta_H$ (360 MHz; CDCl$_3$) 0.95 and 0.97 (2×s, 9H, rotamers), 1.46 (s, 9H), 1.74 (s, 2H), 2.01–2.24 and 2.38–2.44 (2×m, 2H, rotamers), 2.55–2.59 and 2.70–2.81 (2×m, 2H, rotamers), 3.09–3.58 (m, 9H), 3.74–3.85 [m, 4H, {containing at 3.76 and 3.79 (2×s, 3H, rotamers)}], 3.94–4.05 and 4.06–4.19 (2×m, 1H, rotamers), 4.24–4.41 and 4.61–4.69 (2×m, 2H, rotamers), 4.86–4.96 and 5.11–5.21 (2×m, 1H, rotamers), 5.89–6.01 (m, 2H, rotamers), 6.58–6.98 (m, 6H), and 7.13–7.18 and 7.25–7.27 (2×m, 1H, rotamers); LRMS (from LC-MS) (ES+) m/z 651 [(M+H)$^+$] (100).

N1-[(3S,5S)-1-(1,3-benzodioxol-5-ylmethyl)-5-(piperazinocarbonyl)tetrahydro-1H-3-pyrroliumyl]-N1-(3-methoxybenzyl)-3,3-dimethylbutanamide 2,2,2-trifluoroacetate (23a)

A solution of tert-butyl 4-({(2S,4S)-1-(1,3-benzodioxol-5-ylmethyl)-4-[(3,3-dimethylbutanoyl)-3-methoxyanilino]tetrahydro-1H-2-pyrrolyl}carbonyl)-1-piperazinecarboxylate (22) (21.7 mg, 33.3 μmol) in dichloromethane (0.5 mL) was treated with a 95% v/v solution of trifluoroacetic acid in dichloromethane (0.1 mL, 1.2 mmol). The mixture was stirred at room temperature and the course of the reaction was monitored by TLC analysis. Once completed (1 h), the solvent was evaporated under reduced pressure to give 22.8 mg of a mixture of the title trifluoroacetate salt (23a), ethyl acetate and trifluoroacetic acid. This salt was used in the following experiment without further purification:

$\delta_H$ (360 MHz; CDCl$_3$) 0.98 (s, 9H), 2.08–2.18 (m, 1H), 2.32 (d, 1H), 2.43 (d, 1H), 2.73–2.82 (m, 1H), 3.30–3.73 (m, 8H), 3.77 (s, 3H), 3.90–3.96 (m, 1H), 4.06–4.19 (m, 1H), 4.36–4.46 (m, 2H), 4.57 (d, 1H), 4.65–4.73 (m, 1H), 5.57–6.01 (m, 2H), 6.61–6.66 (m, 2H), 6.76–6.91 (m, 4H), and 7.29 (t, 1H); LRMS (from LC-MS) (ES+) m/z 551 [(M+H)$^+$] (100).

N-1-[(3S,5S)-1-(1,3-benzodioxol-5-ylmethyl)-5-(piperazinocarbonyl)tetrahydro-1H-3-pyrrolyl]-N1-(4-methoxybenzyl)-3,3-dimethylbutanamide (23b)

A biphasic mixture of dichloromethane (0.5 mL) and water (0.5 mL) containing 22.8 mg of crude N-1-[(3S,5S)-1-(1,3-benzodioxol-5-ylmethyl)-5-(piperazinocarbonyl)tetrahydro-1H-3-pyrroliumyl]-N-1-(3-methoxybenzyl)-3,3-dimethylbutanamide 2,2,2-trifluoroacetate (23a) was treated with 2.0 M aqueous sodium hydroxide solution until the pH value of the aqueous layer was adjusted to 12. The mixture was vigorously stirred for 5 min at room temperature and the layers were separated. The aqueous layer was extracted with dichloromethane (2×0.5 mL) and the combined organic extracts were dried (MgSO$_4$) and evaporated under reduced pressure to give the title piperazine (23b) (14.5 mg, 79%):

$\delta_H$ (360 MHz; CDCl$_3$) 0.97 and 1.09 (2×s, 9H, rotamers), 1.66–1.79 [m, 3H, {containing at 1.79 (s, 2H)}], 2.03 (d, 1H), 2.13 (d, 1H), 2.32–2.47 (m, 1H), 2.54–2.88 (m, 5H), 3.05–3.12 (m, 1H), 3.29–3.67 (m, 5H), 3.76 (s, 3H), 3.86 (d, 1H), 4.66 (d, 1H), 4.97 (d, 1H), 5.08–5.22 (m, 1H), 5.89–5.92 (m, 2H), 6.59–6.6.81 (m, 6H) and 7.09–7.18 (m, 1H); LRMS (from LC-MS) (ES+) m/z 551 [(M+H)$^+$] (100).

Variations of the protecting group scheme can increase the efficiency and speed with which compounds of the subject invention may be prepared. The schemes below, which can be readily executed by one of skill in the art based on the disclosure above together with known methods in the art, provide rapid, efficient routes to compounds which may inhibit hedgehog activity. As will be understood, the particular moieties, groups, and reactions (e.g., electrophilic or reductive alkylation of the amine) may be varied to produce a wide range of compounds having a structure according to any of Formula I–VI, for example. See also J. W. Mickelson, K. L. Belonga and E. J. Jacobsen, J. Org. Chem., 1995, 60, 4177–4183.

Scheme 1

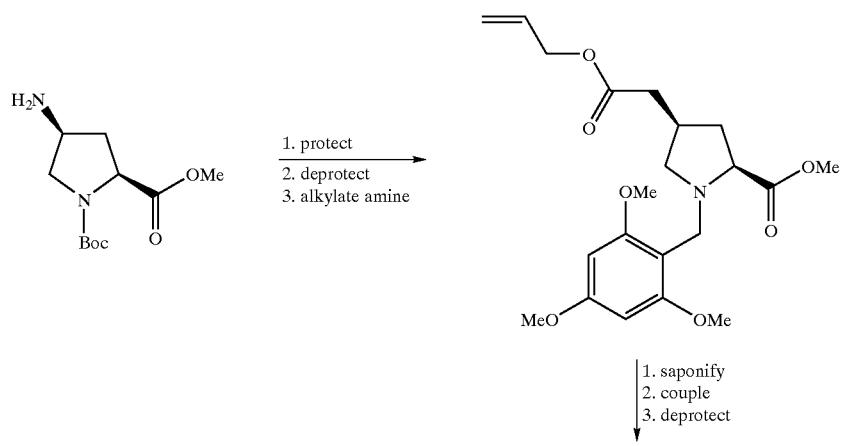

-continued
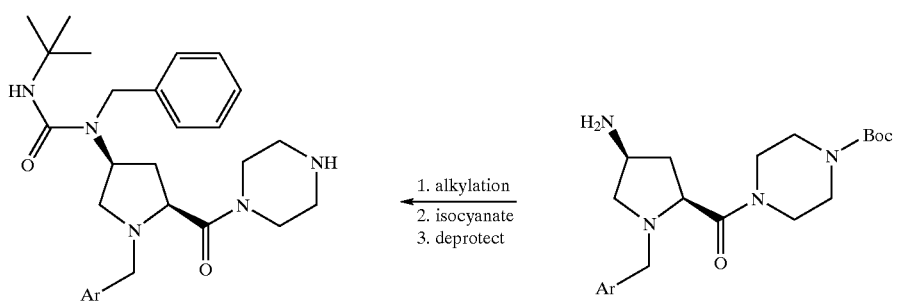
Scheme 2
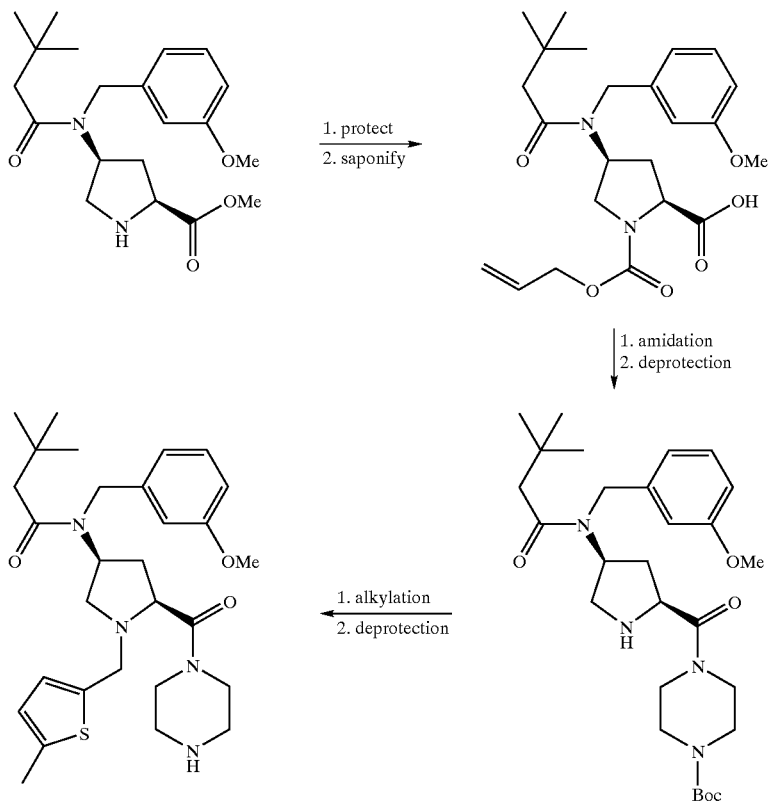
Scheme 3
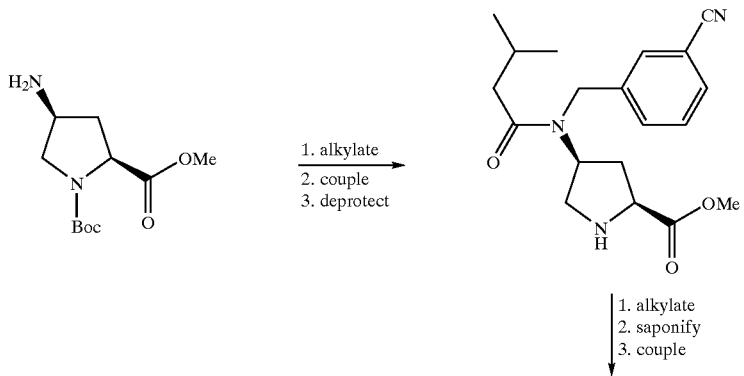

-continued
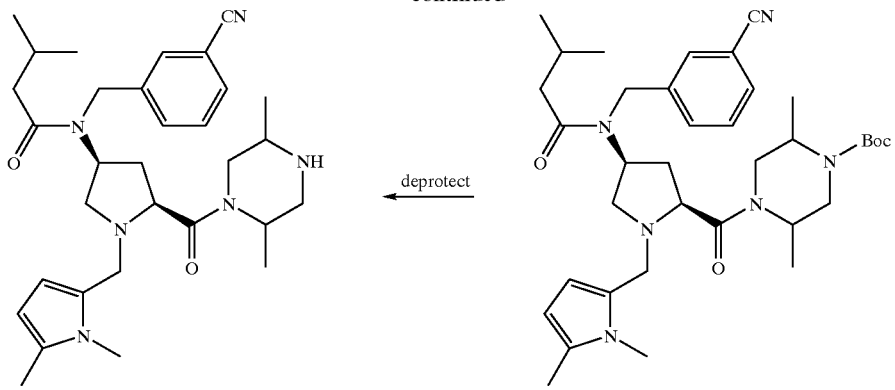
Scheme 4
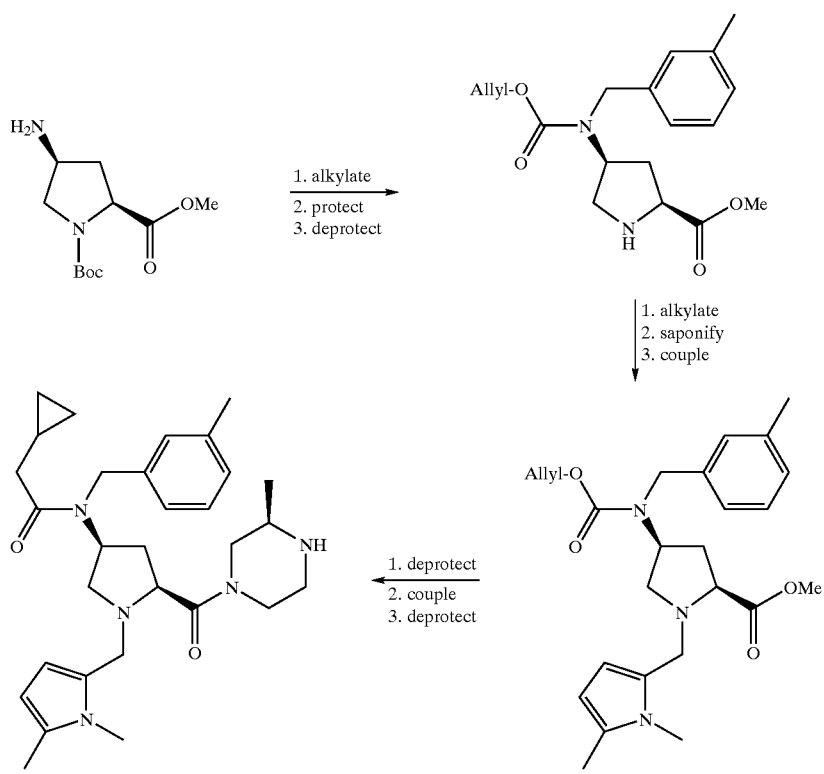
SOLID PHASE ROUTE
The synthetic route used to carry out the production on this template is described in Scheme 5.
Scheme 5
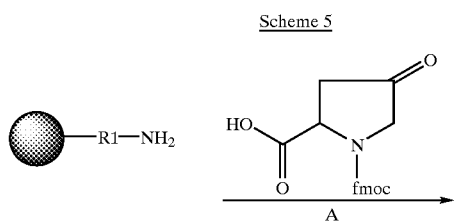
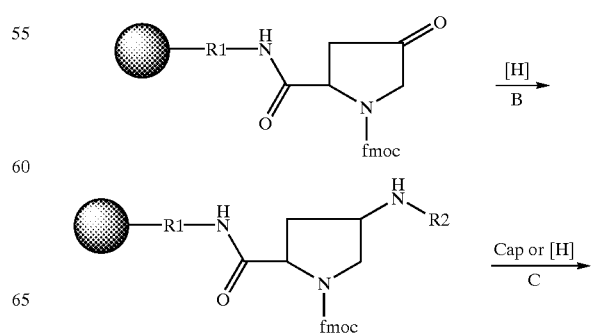

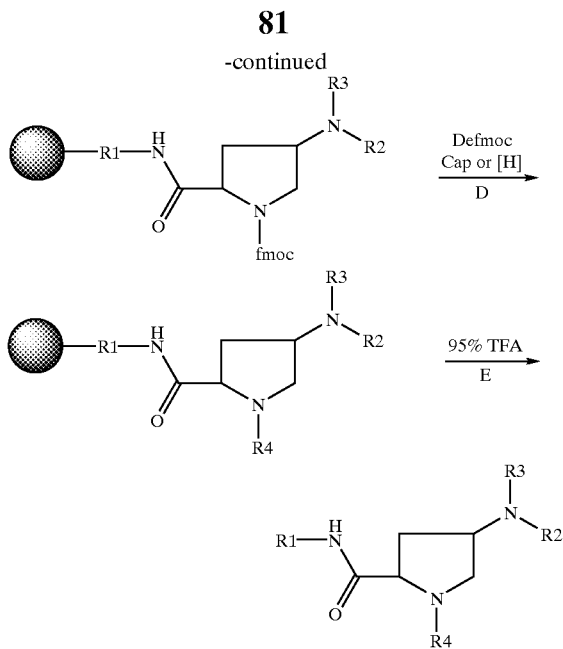

Washing Protocols
  Method 1: water (3×), acetone (2×), N,N-dimethylformamide (3×), water (2×), acetone (1×), N,N-dimethylformamide (3×), water (2×), acetone (3×), methanol (3×), acetone (3×) and methanol (3×);
  Method 2: dichloromethane, hexane, N,N-dimethylformamide, dichloromethane, hexane, dichloromethane and hexane;
  Method 3: water, N,N-dimethylformamide, water, 1.0 M aqueous sodium hydroxide solution, water, N,N-dimethylformamide, water, 1.0 M aqueous sodium hydroxide solution, water, N,N-dimethylformamide, dichloromethane, methanol, dichloromethane and methanol
  Method 4: N,N-dimethylformamide, dichloromethane, N,N-dimethylformamide, dichloromethane, methanol, dichloromethane , methanol (2×) and ether (2×).
  Method 5: N,N-dimethylformamide, dichloromethane, N,N-dimethylformamide, dichloromethane, methanol, dichloromethane and methanol (2×).
Resin swelling in solvents was based on a standard of 10 mL of solvent per gram of resin.

Step A: The Preparation of (Nitrophen-4'-yloxycarboxy)benz-4-yloxymethyl Polystyrene-(Wang PNP Carbonate Polystyrene)

Hydroxybenz-4-yloxymethyl Polystyrene (Wang Resin)

Sodium methoxide (233 g, 4.31 mol) was added slowly to a stirred mixture of chloromethyl polystyrene (2.4 kg, 3.6 mol functionalised loading) and 4-hydroxybenzyl alcohol (581 g, 4.68 mol) in N,N-dimethylacetamide (10 L) under nitrogen. After dilution with N,N-dimethylacetamide (13 L), the mixture was heated at 50 C. for 5 h and then filtered via cannula through a P-ETFE mesh (70 µm). The crude product was washed extensively using the sequence listed in method 1, then dried under vacuum at 60 C. to give 2630 g of the title resin.

(Nitrophen-4'-yloxycarboxy)benz-4-yloxymethyl Polystyrene-(Wang PNP Carbonate Polystyrene)

4-Methylmorpholine (660 mL, 6.0 mol) was added dropwise over 2 h to a stirred mixture of hydroxybenz-4-yloxymethyl polystyrene (2000 g, 2.5 mol functionalised loading) and 4-nitrophenol chloroformate (1209 g, 6.0 mol) in dichloromethane (22 L) at 0 C. under nitrogen. The mixture was warmed gradually to room temperature, stirred overnight and filtered via cannula through a P-ETFE mesh (70 µm). The crude resin was washed extensively using the sequence listed in method 2, then dried under vacuum at room temperature to give 2728 g of a mixture of the title resin and 4-methylmorpholine hydrochloride.

Step B: The Preparation of Wang Resin-bound Diamines
* General Method (for Piperazine, Homopiperazine and trans-1,4-diaminocyclohexane)

Crude (nitrophen-4'-yloxycarboxy)benz-4-yloxymethyl polystyrene (1002.5 g, ~0.9 mol functionalised loading) was swollen over 15 min in a mixture of anhydrous dichloromethane and N,N-dimethylformamide (1:1, v/v, 9 L) under nitrogen. N,N-diisopropylamine (626 mL, 5 mol equivalents) and the appropriate diamine (5 mol equivalents) were added and the mixture was stirred vigorously overnight at room temperature. The mixture was filtered through a P-ETFE mesh (70 µm), washed extensively using the sequence listed in method 3 and dried under vacuum at 60 C. to give the resin-bound diamine.

Ethylenediamine Bound to Wang Resin

Crude (nitrophen-4'-yloxycarboxy)benz-4-yloxymethyl polystyrene (1002.5 g, ~0.9 mol functionalised loading) was swollen over 15 min in dichloromethane (7 L) under nitrogen and treated with ethylenediamine (181 mL, 2.7 mol). The resulting thick, yellow suspension was diluted with dichloromethane (2 L) and vigorously stirred overnight at room temperature. The mixture was filtered through a P-ETFE mesh (70 µm), washed extensively using the sequence listed in method 3 and dried under vacuum at 60 C. to give the title resin-bound diamine.

m-Xylylenediamine Bound to Wang Resin

Crude (nitrophen-4'-yloxycarboxy)benz-4-yloxymethyl polystyrene (1002.5 g, ~0.9 mol functionalised loading) was swollen in tetrahydrofuran (7 L) over 15 min under nitrogen and treated with a solution of m-xylylenediamine (828 mL, 6.27 mol) in tetrahydrofuran (1 L). The resulting thick, yellow suspension was diluted with dichloromethane (2 L) and vigorously stirred overnight at room temperature. The mixture was filtered through a P-ETFE mesh (70 µm), washed extensively using the sequence listed in method 3 and dried under vacuum at 60 C. to give the title resin-bound diamine.

Step C: Building Block Loading onto Wang Diamine

The appropriate resin was swollen in N,N-dimethylformamide over 15 min, then gently agitated and treated with 1-[9H-9-fluorenylmethoxycarbonyl]-4-oxo-2 (S)-pyrrolidinecarboxylic acid (2 equivalents). After 30 min, 1-hydroxybenzotriazole hydrate (2 equivalents) and N,N'-diisopropylcarbodiimide (2 equivalents) were added and the resin suspension was agitated gently overnight at room temperature. After filtration, the resin was washed extensively using the sequence listed in method 4 and dried under vacuum at 40 C.

Step D: Reductive Amination at C-4

The appropriate resin was swollen in a 50% v/v mixture of anhydrous tetrahydrofuran and methanol over 15 min, gently agitated and treated with glacial acetic acid (10 equivalents). The appropriate amine (5 equivalents) and sodium cyanoborohydride (5 equivalents) were added and the resin suspension was agitated gently overnight at room temperature. After filtration, the resin was washed extensively using the sequence listed in method 4 and dried under vacuum at 40 C.

Step E: Reductive Alkylation or Capping

Reductive Alkylation

The appropriate resin was swollen in anhydrous N,N-dimethylfornamide, then gently agitated and treated with glacial acetic acid (10 equivalents). The appropriate aldehyde (5 equivalents) and sodium triacetoxyborohydride (5 equivalents) were added and the resin suspension was agitated cautiously for 1 h at room temperature. The pressure that developed in the reaction vessel over this period was then released and gentle agitation of the suspension was continued overnight at room temperature. The resin was then filtered, washed extensively using the sequence listed in method 4 and dried under vacuum at 40 C.

Acid Chlorides Capping

The appropriate acid chloride (5 equivalents) and N,N-diisopropylethylamine (10 equivalents) were added to a gently agitated suspension of the appropriate resin in a 50% v/v mixture of anhydrous tetrahydrofuran and chloroform. After gentle agitation at room temperature overnight, the resin was filtered, washed extensively using the sequence listed in method 4 and dried under vacuum at 40 C.

Step F: N-Fmoc Deprotection

Resin analogues were suspended in a 20% v/v solution of piperidine in N,N-dimethylformamide and gently agitated for 30 min at room temperature. The resin suspension was subsequently filtered and washed with N,N-dimethylformamide. This treatment of the resin with piperidine in N,N-dimethylfornamide was repeated once more to ensure complete N-Fmoc-deprotection. After standing for 30 min, the resin was filtered, washed using the sequence listed in method 4 and dried under vacuum at 40 C.

Step G: Reductive Alkylation or Capping at N1

Reductive Alkylation

The appropriate resin (~60 mg per well in a 2 ml filter block) was swollen in anhydrous N,N-dimethylformamide (1 mL), then gently agitated and treated with glacial acetic acid (~50 μL, 10 equivalents). The appropriate aldehyde (5 equivalents) and sodium triacetoxyborohydride (~85 mg, 5 equivalents) were added and the filter blocks were then gently agitated at room temperature overnight. Each resin was subsequently filtered and washed using the sequence listed in method 5.

Acid Chlorides Capping

The appropriate resin (~60 mg per well in a 2 ml filter block) was swollen in a 50% v/v mixture of anhydrous tetrahydrofuran and chloroform (1 mL), then gently agitated and treated with the appropriate acid chloride (5 equivalents) and N,N-diisopropylethylamine (~150 μl, 10 equivalents). After gentle agitation of the filter blocks overnight at room temperature, the resins were filtered and washed using the sequence listed in method 5.

Step H: Cleavage of Final Product from Wang Resin Using TFA

The appropriate resin was swollen in DCM and the final product cleaved by addition of 95% v/v TFA in dichloromethane. Four separate aliquots of TFA (2×300 μL, 75 μL, and 500 μL) were added and the filtrates obtained from these were collected in plates containing 96 wells. Filtrates obtained from addition of aliquots 1,2 and 4 were collected using the same 96 well plate. The filtrate obtained after addition of aliquot 3 (75 μL) was collected separately using an analytical 96 well plate. All fractions were subsequently evaporated under reduced pressure using a Genevac apparatus to give the final product.

BIOLOGICAL ASSAYS

Lead Compound Discovery/High-throughput Screening Assay

Compounds to be tested are dissolved in DMSO to a concentration of 10 mM, and stored at −20° C. To activate the Hedgehog pathway in the assay cells, an octylated (lipid-modified) form of the N-terminal fragment of the Sonic Hedgehog protein (OCT-SHH) is used. This N-terminal SHH fragment is produced bacterially.

Compounds may be tested in the "Gli-Luc" assay below, using the cell line 10T(s12), wherein the cells contain a Hedgehog-responsive reporter construct utilizing Luciferase as the reporter gene. In this way, Hedgehog pathway signaling activity can be measured via the Gli-Luc response.

10t1/2(s12) cells are plated in a 96-well micro-titer plate (MTP) at 20,000 cells/well in full medium [DMEM with 10% FBS]. Then plates are placed in the incubator for incubation overnight (O/N), at 37° C. and 5% $CO_2$. After 24 h, the medium is replaced with Luciferase-assay medium (DMEM with 0.5% FBS). Compounds are thawed and diluted in assay medium at 3:1000 (about 300-fold) resulting in a starting concentration of about 30 μM.

Subsequently, 150 μl of each 30 μM sample is added to the first wells (in triplicate). The MTP samples are then diluted at 3-fold dilutions to a total of seven wells, ultimately resulting in a regiment of seven dilutions in triplicate, for each compound. Next, the protein ligand OCT-SHH is diluted in Luciferase-assay medium and added to each well at a final concentration of 0.3 μg/ml. Plates are then returned to the incubator for further incubation O/N, at 37° C. and 5% $CO_2$. After about 24 h, plates are removed from the incubator and the medium is aspirated/discarded. Wells are washed once with assay buffer [PBS+1 mM $Mg^{2+}$ and 1 mM $Ca^{2+}$]. Then 50 μl of assay buffer is added to each well. The Luciferase assay reagent is prepared as described by the vendor (LucLite kit from Packard), and 50 μl is added to each well. Plates are incubated at room temperature (RT) for about 30 minutes after which the signals are read, again at RT, on a Topcount (Packard).

Compounds identified in this assay are depicted in FIG. 32. Testing of individual diastereomers of the depicted compounds in the above assay has demonstrated that cis isomers tend to exhibit greater activity, sometimes by more than 100-fold, than their trans isomer counterparts. Furthermore, ammonium salt derivatives, such as TFA salts, of the subject compounds have been shown to show similar or greater activity in the above assay.

Activities of particular compounds are presented below in Table 1:

TABLE 1

| Compound | $IC_{50}$ (μM) | Compound | $IC_{50}$ (μM) |
|---|---|---|---|
| A | <1 | B | <1 |
| C | <1 | D | <1 |
| E | <0.1 | F | <1 |
| G | <1 | H | <0.1 |
| I | <10 | J | <0.1 |
| K | <0.1 | L | <10 |
| M | <1 | N | <1 |
| O | <0.1 | P | <0.1 |
| Q | <1 | R | <1 |
| S | <1 | T | <1 |
| U | <1 | V | <1 |
| W | <1 | X | <10 |
| Y | <10 | Z | <1 |
| A' | <10 | B' | <10 |
| C' | <10 | D' | <10 |

TABLE 1-continued

| Compound | IC$_{50}$ ($\mu$M) | Compound | IC$_{50}$ ($\mu$M) |
|---|---|---|---|
| E' | <10 | F' | <10 |
| G' | <10 | H' | <10 |
| I' | <10 | J' | <10 |
| K' | <10 | L' | <10 |
| M' | <0.1 | N' | <1 |
| O' | <0.1 | P' | <10 |
| Q' | <10 | R' | <1 |
| S' | <10 | T' | <1 |
| U' | <1 | V' | <1 |
| W' | <1 | X' | <0.1 |
| Y' | <1 | Z' | <1 |
| A" | <1 | B" | <1 |
| C" | <1 | D" | <10 |
| E" | <10 | F" | <10 |
| G" | <1 | H" | <10 |
| I" | <0.1 | J" | <0.1 |
| K" | <1 | L" | <1 |
| M" | <1 | N" | <1 |
| O" | <1 | P" | <10 |
| Q" | <10 | R" | <1 |
| S" | <1 | T" | <1 |
| U" | <10 | V" | <1 |
| W" | <10 | X" | <10 |
| Y" | <10 | Z" | <1 |
| A''' | <1 | B''' | <1 |
| C''' | <10 | D''' | <10 |
| E''' | <10 | F''' | <1 |
| G''' | <10 | H''' | <10 |
| I''' | <10 | J''' | <10 |
| K''' | <10 | L''' | <10 |

Ptc-null Assay
Methods

Ptc-null cells were cultured for 3 days in the presence of vehicle; jervine, a known Patched pathway antagonist (i) used here as a positive control; or 1 $\mu$M of compound D. Total ribonucleic acid (RNA) was isolated from the cells and used for reverse transcriptase-polymerase chain reaction (RT-PCR). Specific primers for the detection of mouse gli-1 mRNA were used in the PCR, and the actin gene was used to demonstrate that equivalent amounts of mRNA samples were compared in the experiment. The gli-1 and actin mRNA samples were then loaded on 1.5% agarose gel and were detected by staining with ethidium bromide. The same samples were analyzed by the quantitative real-time polymerase chain reaction method to quantify the levels of gli-1 mRNA.

Results

Figure 33A:
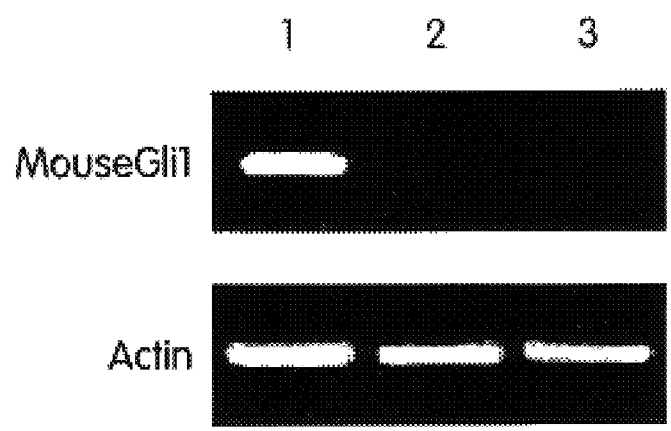
FIG. 33A shows gli-1 mRNA expression in cells treated with vehicle (Lane 1); 5 μM jervine, the positive control compound (Lane 2); and 1 μM D (Lane 3). Compared with vehicle, D and jervine significantly decreased the expression of gli-1 mRNA.
Figure 33B:
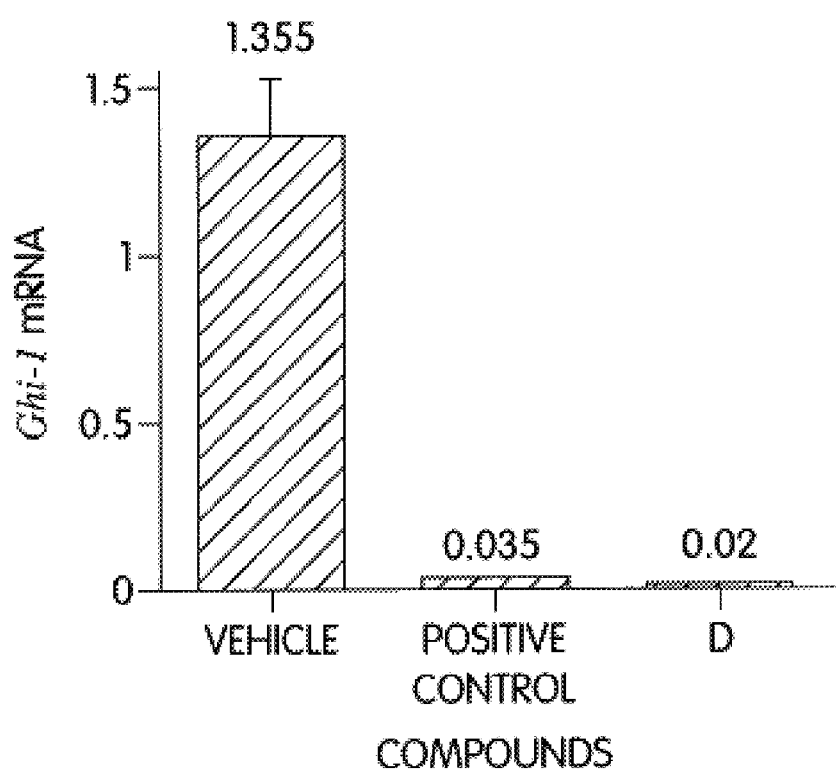
FIG. 33B demonstrates that D and jervine inhibited the gli-1 mRNA levels as measured by quantitative real-time PCR.

FIG. 33A shows the results of a representative experiment. It shows gli-1 mRNA expression in cells treated with a vehicle control (Lane 1); 5 $\mu$M jervine, the positive control compound (Lane 2); and 1 $\mu$M D (Lane 3). Compared with vehicle, D and jervine significantly decreased the expression of gli-1 mRNA in ptc-null cells. The levels of actin mRNA were equivalent in all conditions, indicating that equal quantities of RNA were analyzed in the experiment. This qualitative result was confirmed by the quantitative real-time PCR analysis (FIG. 33B), which shows that D and jervine downregulated the gli-1 mRNA levels.

Together, these experiments confirm that exposure of ptc-null cells to D for 3 days downregulates the Patched pathway, as demonstrated by the inhibition of the expression of gli-1 mRNA transcripts.

Embryonic Mouse Skin Punch Assay: Effect of Prolonged Exposure to D
Methods

A novel cell culture assay was established to determine the effects of D on activation of the Patched pathway in skin. In this system, activation of the Patched pathway results in increased expression of the ptc gene.

To monitor the activity of the Patched pathway in embryonic skin, we cultured pieces of skin from transgenic Patched pathway reporter mice. These mice were genetically engineered to harbor a foreign gene (lacZ). The lacZ gene encodes a bacterial beta-galactosidase. The gene was inserted in the ptc locus but allowed for normal ptc function. Ptc activation in response to Shh-induced Patched pathway activation can then be monitored by the production of the lacZ gene product, beta-galactosidase, which is detectable by the enzymatic conversion of the substrate X-gal into a blue-colored reaction product.

Day 17.5 embryonic skin was explanted as 2 mm circular punches from these transgenic reporter mice and cultured for 5 to 7 days in the presence of Shh protein (FIG. 34). Shh protein should upregulate the expression of the ptc gene, hence increase the amount of X-gal staining in these cultures. To test the effect of D, skin punches were cultured for 6 days in the presence of both Shh protein and D (FIG. 35).

Results

Figure 34A:
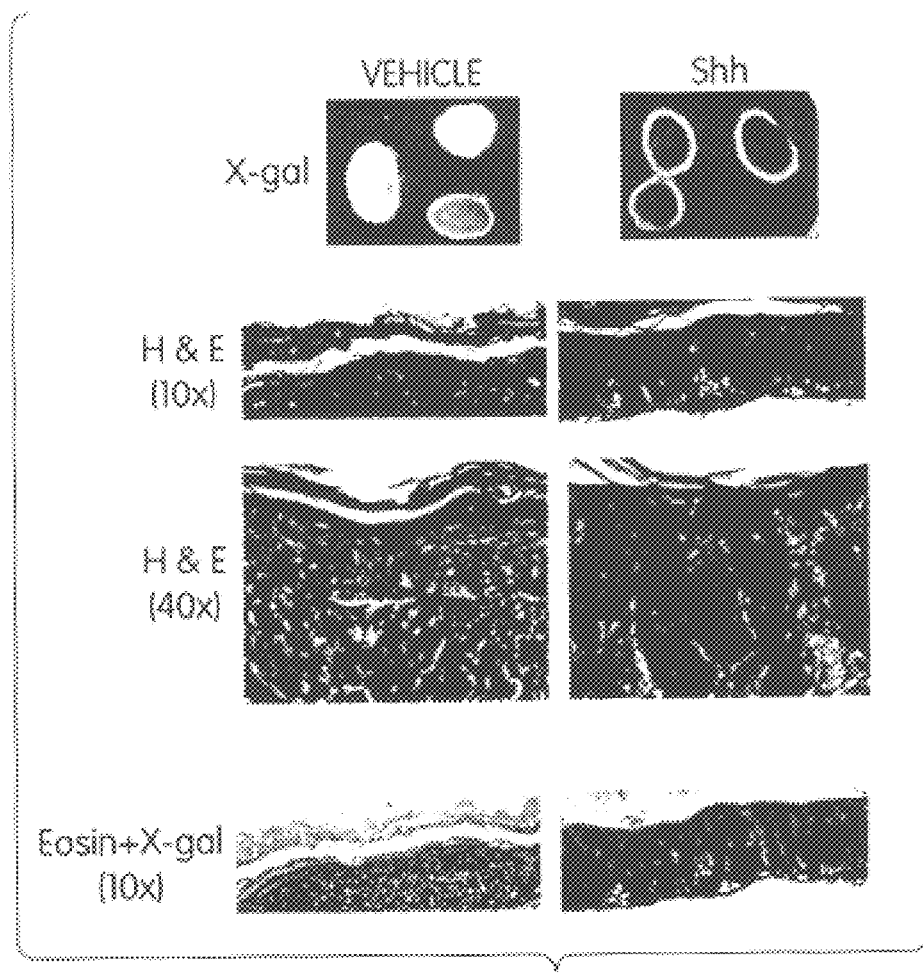
FIG. 34A shows that adding Shh protein to cultured skin explants resulted in ptc activation as indicated by the blue staining of these cultures (X-gal). Histology samples show intensely stained cells with basophilic nuclei and a high nucleus to cytoplasm ratio (H&E [10×] and H&E [40×]). These structures resemble BCCs in that they are arranged in clusters throughout the dermal layer and are separated by palisades of normal appearing dermal cells. Blue staining indicates that the Patched pathway was active in cells within the BCC-like structures (Eosin+X-gal).

As expected, adding Shh protein to cultured skin explants resulted in ptc activation as indicated by the blue X-gal staining of these cultures (FIG. 34A—X-gal).

Hematoxylin and eosin (H&E) staining of sectioned skin punches revealed intensely stained cells with basophilic nuclei and a high nucleus to cytoplasm ratio (FIG. 34A—H&E [10×] and H&E [40×]). These structures resemble BCCs in that they were arranged in clusters throughout the dermal layer and were separated by palisades of normal appearing dermal cells.

Figure 34B:
FIG. 34B illustrates that BCC-like clusters, one of which is indicated by the arrow, in the mouse skin punch expressed keratin-14 (brown reaction product), a marker of undifferentiated keratinocytes. Undifferentiated basal cells in the epidermis were also keratin-14-positive. Human BCCs are reported to express keratin-14.

X-gal staining demonstrated that the Patched pathway was active in cells within these BCC-like structures (FIG. 34A—Eosin+X-gal). Consistent with published results and similar to human BCCs, the BCC-like clusters in the mouse skin punch expressed keratin-14, a marker of undifferentiated keratinocytes (FIG. 34B).

Figure 35A:
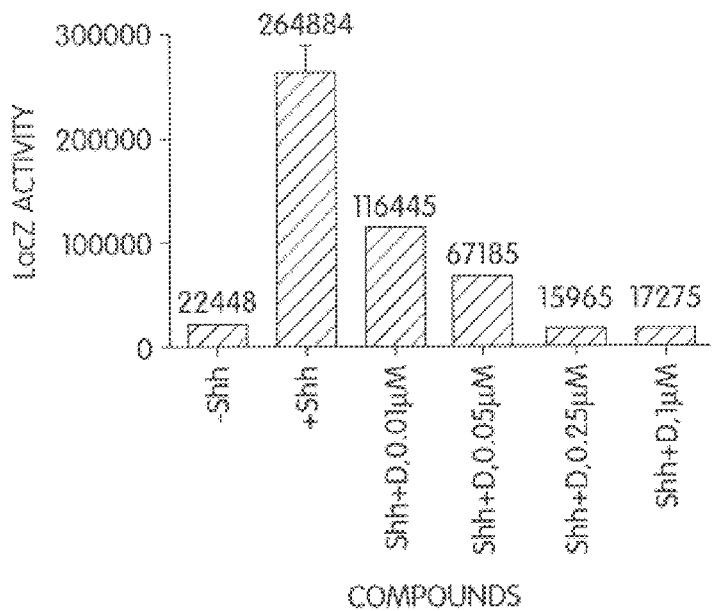
FIG. 35A demonstrates that increasing concentrations of D are associated with a dose-dependent decrease in the amount of lacZ reporter enzyme activity. Lower levels of lacZ activity are indicative of decreased Patched pathway activity in the presence of Shh protein.
Figure 35B:
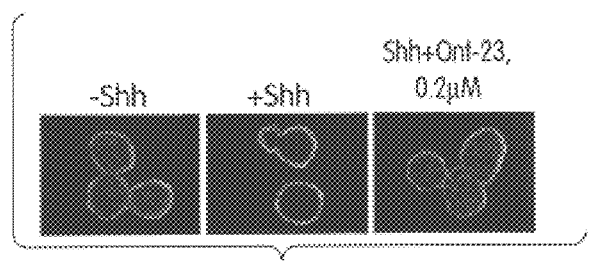
FIG. 35B shows staining of D-treated explants and demonstrates that 0.2 μM D decreased X-gal staining compared with the intense X-gal staining of skin punches treated with Shh protein alone, indicating the downregulation of the expression of the ptc gene.

Skin punches were cultured for 6 days in the presence of both Shh protein and D to test the effect of D. FIG. 35 demonstrates the dose-dependent effect of D on the level of Patched pathway activity in Shh-treated skin punches. Increasing concentrations of D (from 0.01 to 1 $\mu$M) led to a dose-dependent decrease in the amount of pathway activity, as monitored by the amount of lacZ reporter enzyme activity (FIG. 35A). Reporter enzyme staining of D treated explants demonstrated that 0.2 $\mu$M D decreased X-gal staining compared with the intense X-gal staining of skin punches treated with Shh protein alone (FIG. 35B). This indicates that D blocked the activation of the Patched pathway and downregulated the expression of the ptc gene.

Figure 35C:
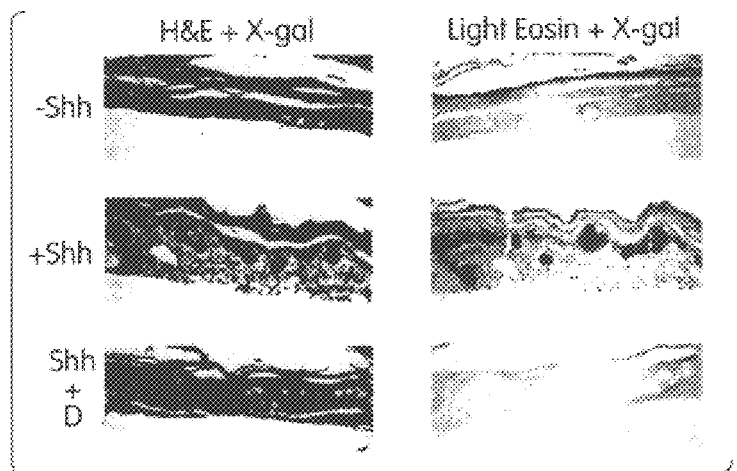
FIG. 35C portrays histology samples of skin punches treated with D (bottom row), suggesting that treatment inhibited the appearance of Shh-induced BCC-like structures.

The next experiment demonstrated that inhibiting the Patched pathway with D would prevent the formation of BCC-like structures. FIG. 35C shows that D completely blocked the formation of BCC-like structures without affecting the integrity of normal skin cells. This confirms that D can prevent the appearance of BCC-like structures produced by activating the Patched pathway, the same pathway that underlies the human disease.

Embryonic Mouse Skin Punch Assay: Effect of Short-term Pretreatment with D
Methods Transgenic mouse-derived skin punches were treated with vehicle or D for 5 hours in the absence of Shh. After the pretreatment, the vehicle or D was removed. The skin punches were washed twice and then cultured in the presence of Shh for 6 days. At the end of the experiment, the skin punches were fixed and stained with X-gal to determine Patched pathway activity.

Results

Figure 36:
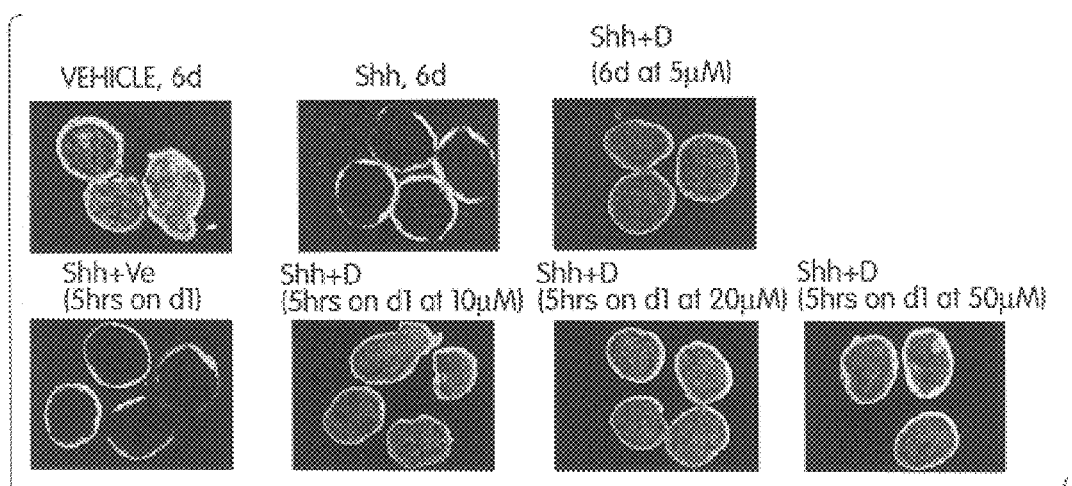
FIG. 36 depicts that skin punches treated for 6 days with exogenous Shh protein alone showed intense X-gal staining compared with those treated with vehicle alone (top row). Skin punches pretreated with D at 10, 20 and 50 μM for 5 hours before being exposed to exogenous Shh protein demonstrated complete inhibition of Shh protein-induced upregulation of the Patched pathway (bottom row—3 slides on the right). No inhibition was seen when the skin punches pretreated with vehicle were exposed to exogenous Shh protein, as shown by intense X-gal staining (bottom row on the left). The short period of pretreatment was essentially equivalent to 6-day exposure to D in terms of the level of ptc inhibition (compare top and bottom rows).

Skin punches treated for 6 days with exogenous Shh protein alone showed intense X-gal staining (i.e., activation) compared with those treated with vehicle alone (FIG. 36, top row). Skin punches pretreated with D at 10, 20 and 50 μM for 5 hours before being exposed to exogenous Shh protein demonstrated complete inhibition of Shh protein-induced upregulation of the Patched pathway, as indicated by the absence of X-gal staining (FIG. 36, bottom row—3 slides on the right). Intense X-gal staining indicative of upregulation of the Patched pathway was seen in skin punches pretreated with vehicle before exposure to Shh protein (FIG. 36, bottom row, left). The short period of pretreatment was essentially equivalent to 6-day exposure to D in terms of the level of ptc inhibition (compare top and bottom rows in FIG. 36).

This result suggests that D binds tightly to its target and that the kinetics of dissociation are slow or irreversible. The data also suggest that D might have the capacity to prevent the development of BCC.

Embryonic Mouse Skin Punch Assay: Long-term Treatment of Pre-existing BCC-Like Structures with D Methods Day 17.5 embryonic skin punches from transgenic Patched pathway reporter mice were cultured in the presence of Shh protein for 7 days to allow for the development of BCC-like structures. The Shh protein was removed at the end of the 7 days. The cultures were then exposed to Shh protein plus either vehicle or D for 3 days. The cultures were analyzed histologically after 10 days to assess the formation of BCC-like structures that are indicative of activation of the Patched pathway.

Results

Figure 37A:
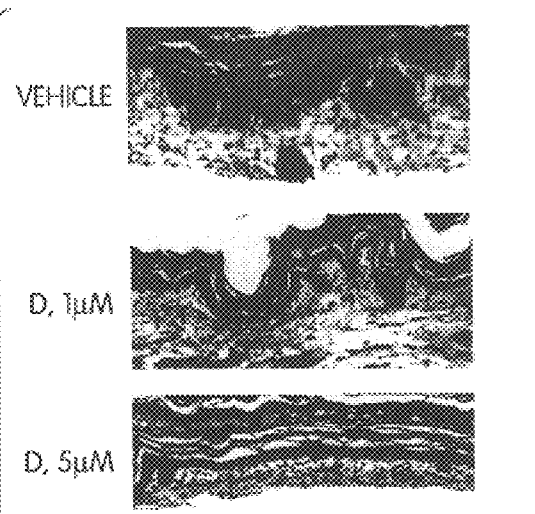
FIG. 37A shows that D, at either 1 or 5 μM, significantly reduced the size and number of Shh-induced BCC-like structures in treated skin punches, as compared with vehicle treated explants.

Histological analysis showed that D, at either 1 or 5 μM, significantly reduced the size and number of Shh-induced BCC-like structures in treated skin punches, as compared with vehicle treated explants (FIG. 37A). Thus, it appears that exposing existing BCC-like structures to D for 3 days induced the regression of these structures. Furthermore, D did not appear to have general cytotoxic effects on skin cells, as determined by their normal histology.

Figure 37B:
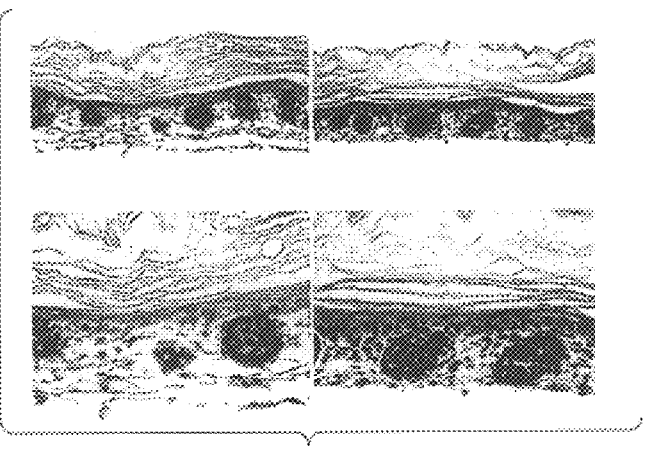
FIG. 37B illustrates that after 2 days of exposure to 5 μM D (right) or vehicle (left), apoptotic nuclei, indicated by the brown color in the slides on the right, appeared within the BCC-like structures.

One possible mechanism for D-induced regression of BCC-like structures may be apoptosis of the activated cells. To investigate this possibility, parallel explants were exposed to 5 μM D for 2 days and were then stained by the terminal deoxynucleotidyltransferase mediated d-UTP nick end-labeling (TUNEL) method, which is used to detect apoptotic nuclei. After 2 days of exposure to 5 μM D, the number of apoptotic nuclei (indicated by the brown color in the slides on the right) within the BCC-like structures was significantly higher than in the vehicle control on the left (FIG. 37B). Taken together, these results suggest that D-induced regression of BCC-like structures results, at least in part, from stimulating the cellular suicide pathway of cells in which the Patched pathway is activated.

Embryonic Mouse Skin Punch Assay: Short-term Treatment of Pre-existing BCC-like Structures with D Methods Day 17.5 embryonic skin punches from transgenic Patched pathway reporter mice were cultured in the presence of Shh protein for 7 days. The Shh protein was removed at the end of the 7 days. The skin punches were then exposed to vehicle or 1 or 5 μM D for 5 hours on days 7 and 9. After each exposure to vehicle or D, the vehicle or D was washed off and the skin punches were cultured again in the presence of Shh protein. Cultures were analyzed by X-gal staining after 10 days in vitro to assess the activity of the Patched pathway.

Results

Figure 38A:
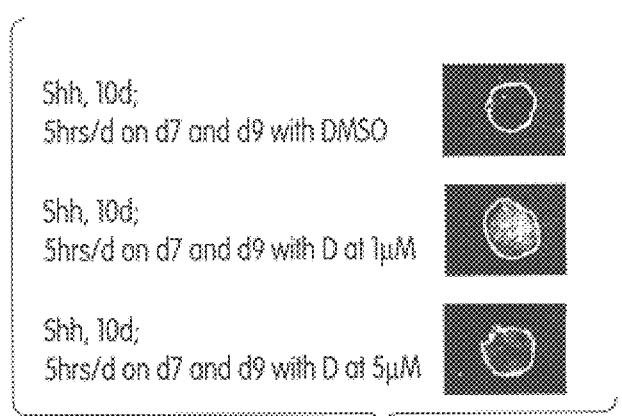
FIG. 38A demonstrates that short-term treatment with D reduced the amount of X-gal staining, suggesting a downregulation of pathway activity, compared with vehicle.
Figure 38B:
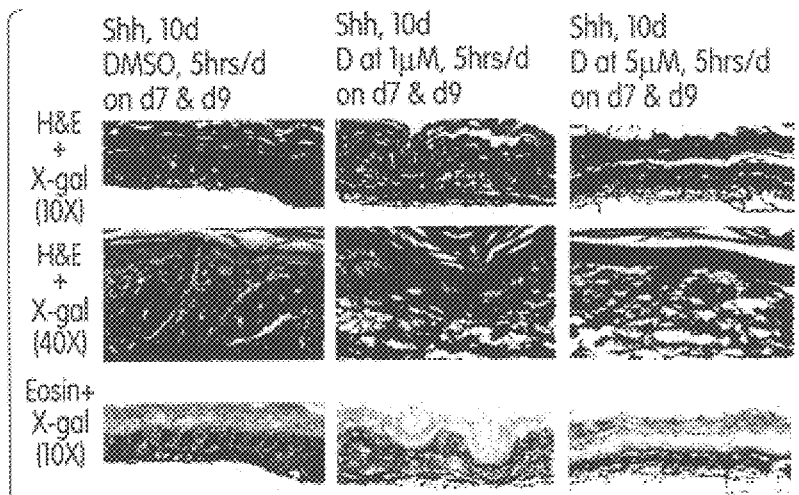
FIG. 38B shows that even at a concentration of 1 μM, D induced the regression of X-gal-positive BCC-like structures compared with vehicle.
Figure 38C:
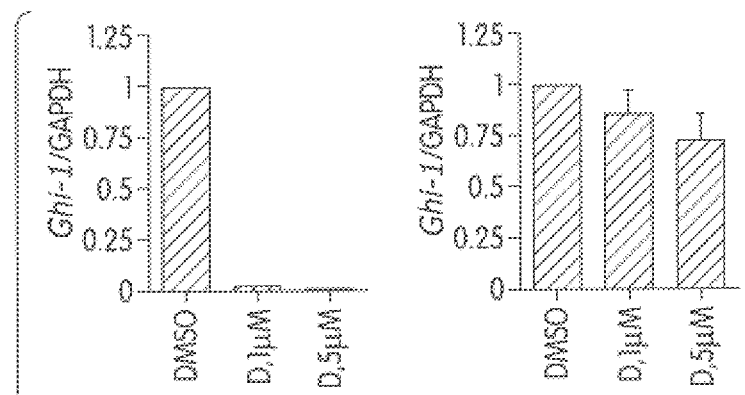
FIG. 38C portratys that short-term treatment with D completely downregulated gli-1 transcription (left). This effect appeared to be specific to the Patched pathway and was not due simply to general cytotoxicity, as shown by the fairly constant mRNA levels of a housekeeping enzyme, GAPDH (right).

Short-term treatment with D reduced the amount of X-gal staining associated with exposure to Shh protein (FIG. 38A), suggesting a downregulation of pathway activity in skin explants. Histological analysis showed that even at a concentration of 1 μM, D induced the regression of X-gal-positive BCC-like structures (FIG. 38B). Quantification of the gli-1 mRNA levels in D-treated punches demonstrated that short-term treatment with D completely downregulated gli-1 transcription (FIG. 38C, left side). This effect appeared to be specific to the Patched pathway and not due to general cytotoxicity, as shown by the relatively constant mRNA levels of a housekeeping enzyme, glyceraldehyde-3-phosphate dehydrogenase or GAPDH (FIG. 38C, right side). These results demonstrate that under certain conditions of short-term exposure, D has the capacity to inhibit the activity of the Patched pathway in cultured embryonic skin explants. Furthermore, D at concentrations of both 1 and 5 μM caused the regression of existing Shh-induced BCC-like structures.

Adult BCC Mouse Skin Punch Assay

Methods

Ptc heterozygous transgenic mice were irradiated 3 times weekly for 6 months, during which time many small, and often microscopic, BCC tumors developed. Four-mm diameter skin punch explants, presumably containing BCC structures, were cultured for 6 days in the presence of vehicle, the positive control (jervine), or 5 μM D. At the end of the experiment, the explants were analyzed by X-gal staining to detect the level of Patched pathway activity, by histology to determine the effect of treatment on the morphology of ultraviolet radiation-induced BCCs, and by quantifying the level of gli-1 mRNA expression to characterize the extent of pathway inhibition.

Results

Figure 39A:
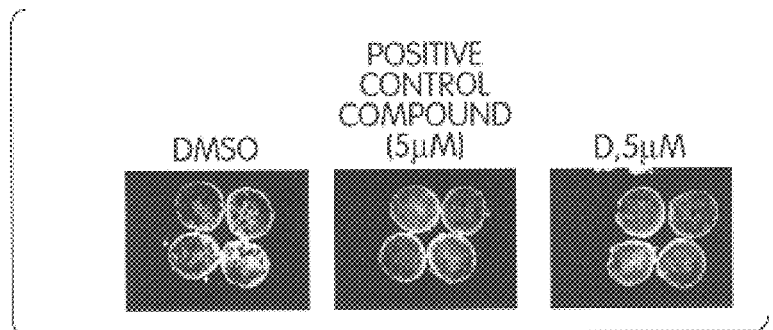
FIG. 39A: X-gal staining of the treated explants showed that skin punches cultured in the presence of vehicle alone developed intensely stained blue foci indicative of an upregulation of the Patched pathway and BCC structures. Compared with vehicle, 5 μM D, like the jervine positive control, greatly decreased the number and size of BCC structures (blue spots).
Figure 39B:
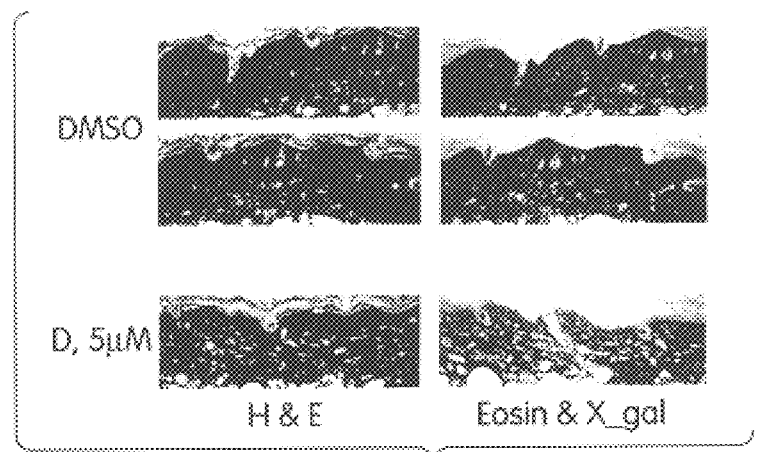
FIG. 39B: Histology samples showed that 5 μM D reduced the number of ultraviolet-induced BCC structures, as compared with the vehicle control.
Figure 39C:
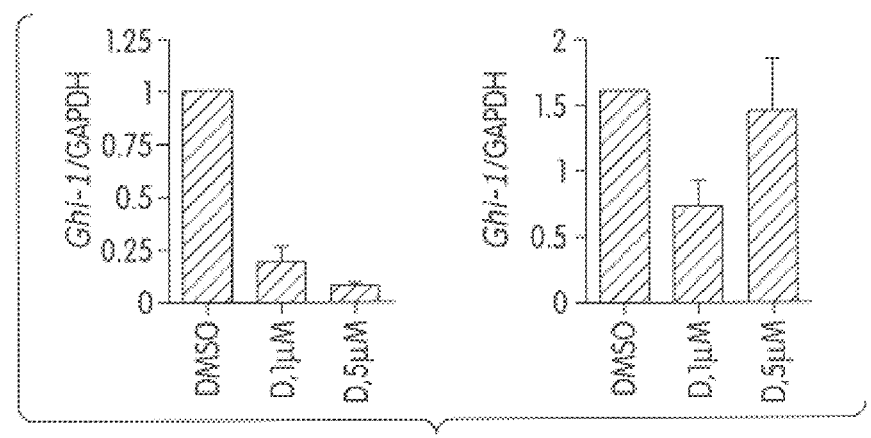
FIG. 39C: In skin punches from transgenic mice D, at concentrations of 1 and 5 μM, significantly inhibited the level of gli-1 mRNA compared with skin punches from mice treated with vehicle alone (left). This inhibition did not appear to be caused by non-specific cytotoxicity, as statistical comparison (using ANOVA) of the mRNA levels of the gene that encodes the housekeeping GAPDH enzyme among groups showed no significant difference in general cellular metabolic activity (right).

X-gal staining of the treated explants shows that skin punches cultured in the presence of vehicle alone developed intensely stained blue foci indicative of a focal upregulation of the Patched pathway and BCC structures (blue spots in FIG. 39A). Compared with vehicle, 5 μM D, like the positive control, decreased the number and size of established BCC structures. Histological analysis of sectioned explants demonstrated that D induced the regression of ultraviolet radiation-induced BCC tumors, as compared with the vehicle control (FIG. 39B). In skin punches from these heterozygous transgenic mice, the levels of gli-1 mRNA were high because of the activation of ptc target genes. D at concentrations of 1 and 5 μM also significantly inhibited the level of gli-1 mRNA levels compared with vehicle alone. Quantification of gli-1 mRNA levels shows the almost complete inhibition of target gene activation by D (FIG. 39C). This inhibition did not appear to be caused by non-specific cytotoxicity, as statistical comparison of the levels of the housekeeping GAPDH enzyme between treated and vehicle conditions shows no significant difference among groups in general cellular metabolic activity. Thus, these results demonstrate that D inhibits the Patched pathway and induces the regression of ultraviolet radiation-induced, BCNS-like, BCC tumors in cultured skin explants.

These data confirm the results of previous experiments and suggest that D might be effective in treating BCC.

Human BCC Explant Culture

Methods

Specimens obtained from surgical procedures (such as Mohs surgery or curettage) were cultured on fresh, living, day 17 embryonic mouse dermis from which all epidermal cells have been removed by digestion using dispase. Since dispase treatment digests basement membrane components, Matrigel, a commercially available basement membrane preparation, was applied between the dermis and BCC. Cultures were assembled on top of a plastic grid and incubated for 3 days (with or without D at a concentration of 10 µM) in a medium suitable for the long-term culture of human skin. After culture, the samples were processed for routine histology and subjected to quantitative in situ hybridization. Briefly, 7 µm sections of paraformaldehyde-fixed, paraffin-embedded tissue containing large basal cell islands were cleared, re-hydrated, digested with proteinase K, acetylated and hybridized with [$^{33}$P]-labeled RNA probes overnight. After high stringency post-hybridization washes, slides were exposed to a PhosphorImager screen in the dark at room temperature for 4–7 days. After developing, the [$^{33}$P]-signal was scanned using a Storm Scanner (Molecular Dynamics). Individual basal cell islands were selected and the signal quantified and expressed in average counts/pixel using ImageQuant 1.0 software.

Results

Figure 40A:
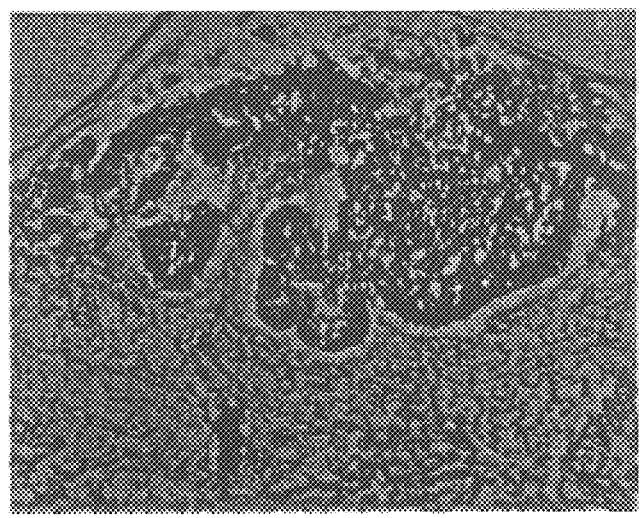
FIG. 40A: The morphological features characteristic of BCCs, such as islands of undifferentiated basal cells, and in some cases, palisading of peripheral cells and stromal clefting were maintained when cultures were stained with H&E.
Figure 40B:
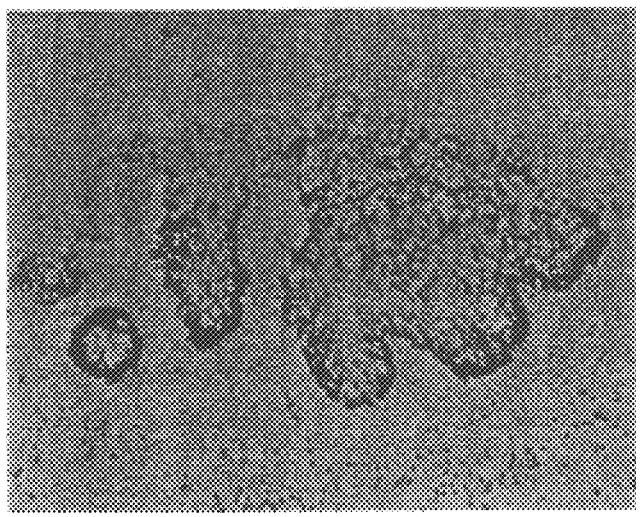
FIG. 40B: The GLI-1 gene, a pivotal indicator of Patched signaling, remained active at high levels, as indicated in red.
Figure 41:
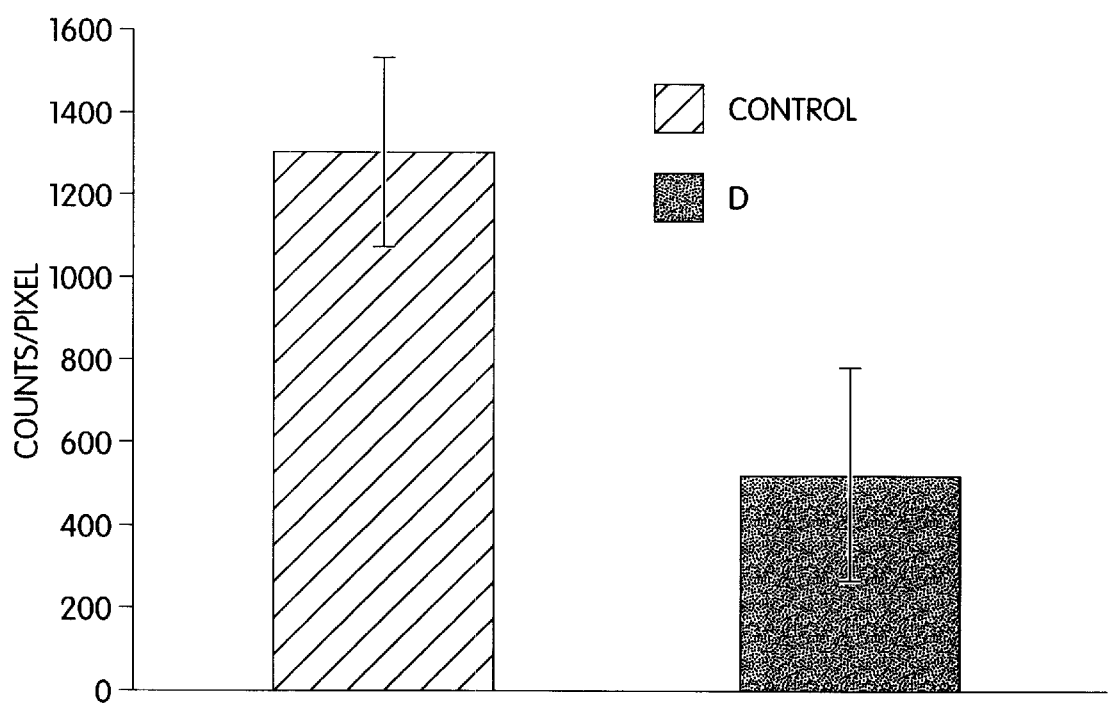
FIG. 41: Quantitative in situ hybridization shows that the level of GLI-1 expression is reduced in the D-treated samples as compared to vehicle-treated controls.

The morphological features characteristic of BCCs, such as islands of undifferentiated basal cells, and in some cases, palisading of peripheral cells and stromal clefting (FIG. 40A) were maintained when BCCs were cultured in this system. Likewise, the differentiation markers that were expressed are identical in pattern to those of the pre-culture controls, as determined by immunohistochemical staining (data not shown). The GLI-1 gene, a pivotal indicator of Patched signaling, remained active at high levels in untreated cultures, as determined from sections exposed to $^{33}$P-labeled RNA probes (FIG. 40B). Quantitative in situ hybridization showed that the level of GLI-1 expression was greatly reduced in the D-treated samples as compared to vehicle-treated controls (FIG. 41).

Preparation of Compounds of the Present Invention a. Illustrative Synthetic Schemes Exemplary synthesis schemes for generating hedgehog antagonists useful in the methods and compositions of the present invention are shown in FIGS. 1–31.

The reaction conditions in the illustrated schemes of FIGS. 1–31 are as follows:
1) $R_1CH_2CN$, $NaNH_2$, toluene (Arzneim-Forsch, 1990, 40, 11, 1242)
2) $H_2SO_4$, $H_2O$, reflux (Arzneim-Forsch, 1990, 40, 11, 1242)
3) $H_2SO_4$, EtOH, reflux (Arzneim-Forsch, 1990, 40, 11, 1242)
4) NaOH, EtOH, reflux
5) $(Boc)_2O$, 2M NaOH, THF
6) LiHDMS, $R_1X$, THF (Merck Patent Applic # WO 96/06609)
7) Pd—C, $H_2$, MeOH
8) t-BuONO, CuBr, HBr, $H_2O$ (J. Org. Chem. 1977, 42, 2426)
9) $ArB(OH)_2$, $Pd(PPh_3)_4$, Dioxane (J. Med. Chem. 1996, 39, 217–223)
10) $R_{12}(H)C=CR_{13}R_{14}$, $Pd(OAc)_2$, $Et_3N$, DMF (Org. React. 1982, 27, 345)
11) $Tf_2O$, THF (J. Am. Chem. Soc. 1987, 109, 5478–5486)
12) $ArSnBu_3$, $Pd(PPh_3)_4$, Dioxane (J. Am. Chem. Soc. 1987, 109, 5478–5486)
13) $KMnO_4$, Py, $H_2O$ (J. Med. Chem. 1996, 39, 217–223)
14) $NaOR_1$, THF
15) $NaSR_1$, THF
16) $HNR_1R_{13}$, THF
17) HONO, $NaBF_4$ (Adv. Fluorine Chem. 1965, 4, 1–30)
18) $Pd(OAc)_2$, NaH, DPPF, $PhCH_3$, $R_1OH$ (J. Org. Chem. 1997, 62, 5413–5418)
19) i. $R_1X$, $Et_3N$, $CH_2Cl_2$, ii. $R_{13}X$
20) $SOCl_2$, cat DMF
21) $CH_2N_2$, $Et_2O$
22) $Ag_2O$, $Na_2CO_3$, $Na_2S_2O_3$, $H_2O$ (Tetrahedron Lett. 1979, 2667)
23) $AgO_2CPh$, $Et_3N$, MeOH (Org. Syn., 1970, 50, 77; J. Am. Chem. Soc. 1987, 109, 5432)
24) LiOH, THF—MeOH
25) $(EtO)_2P(O)CH_2CO_2R$, BuLi, THF
26) $MeO_2CCH(Br)=P(Ph)_3$, benzene
27) KOH or KOtBu
28) Base, $X(CH_2)_nCO_2R$
29) DPPA, $Et_3N$, toluene (Synthesis 1985, 220)
30) HONO, $H_2O$
31) $SO_2$, CuCl, HCl, $H_2O$ (Synthesis 1969, 1–10, 6)
32) Lawesson's reagent, toluene (Tetrahedron Asym. 1996, 7, 12, 3553)
33) $R_2M$, solvent
34) 30% $H_2O_2$, glacial $CH_3CO_2H$ (Helv. Chim. Acta. 1968, 349, 323)
35) triphosgene, $CH_2Cl_2$ (Tetrahedron Lett., 1996, 37, 8589)
36) i. $(EtO)_2P(O)CHLiSO_2Oi$-Pr, THF, ii. NaI
37) $Ph_3PCH_3I$, $NaCH_2S(O)CH_3$, DMSO (Synthesis 1987, 498)
38) $Br_2$, $CHCl_3$ or other solvent (Synthesis 1987, 498)
39) BuLi, $Bu_3SnCl$
40) $ClSO_2OTMS$, $CCl_4$ (Chem. Ber. 1995, 128, 575–580)
41) MeOH—HCl, reflux
42) LAH, $Et_2O$ or $LiBH_4$, EtOH or $BH_3$—THF (Tetrahedron Lett., 1996, 37, 8589)
43) MsCl, $Et_3N$, $CH_2Cl_2$ (Tetrahedron Lett., 1996, 37, 8589)
44) $Na_2SO_3$, $H_2O$ (Tetrahedron Lett., 1996, 37, 8589)
45) $R_2R_4NH$, $Et_3N$, $CH_2Cl_2$
46) $R_2M$, solvent
47) $CH_3NH(OCH_3)$, EDC, HOBt, DIEA, $CH_2Cl_2$ or DMF (Tetrahedron Lett, 1981, 22, 3815)
48) MeLi, THF
49) mCPBA, $CH_2Cl_2$
50) HONO, $Cu_2O$, $Cu(NO_3)_2$, $H_2O$ (J. Org. Chem. 1977, 42, 2053)
51) $R_1M$, solvent
52) HONO, NaS(S)COEt, $H_2O$ (Org. Synth. 1947, 27, 81)
53) $HSR_2$ or $HSR_4$, $CH_2Cl_2$
54) i-BuOC(O)Cl, $Et_3N$, $NH_3$, THF
55) $R_2R_4NH$, $CH_2Cl_2$, $NaBH(OAC)_3$
56) $R_2R_4NH$, MeOH/$CH_3CO_2H$, $NaBH_3CN$
57) $R_2OH$, EDC, HOBt, DIEA, $CH_2Cl_2$ or DMF
58) $R_2OH$, HBTU, HOBt, DIEA, $CH_2Cl_2$ or DMF
59) $R_2R_4NH$, EDC, HOBt, DIEA, $CH_2Cl_2$ or DMF
60) $R_2R_4NH$, HBTU, HOBt, DIEA, $CH_2Cl_2$ or DMF
61) $POCl_3$, Py, $CH_2Cl_2$
62) $R_2R_4NCO$, solvent
63) $R_2OC(O)Cl$, $Et_3N$, solvent
64) $R_2CO_2H$, EDC or HBTU, HOBt, DIEA, $CH_2Cl_2$ or DMF
65) $R_2X$, $Et_3N$, solvent
66) $(CH_3S)_2C=N(CN)$, DMF, EtOH (J. Med. Chem. 1994, 37, 57–66)
67) $R_2SO_2Cl$, $Et_3N$, $CH_2Cl_2$
68) $R_2$— or $R_3$— or $R_4CHO$, MeOH/$CH_3CO_2H$, $NaBH_3CN$ (Synthesis 1975, 135–146)
69) Boc(Tr)-D or L-CysOH, HBTU, HOBt, DIEA, $CH_2Cl_2$ or DMF
70) Boc(Tr)-D or L-CysH, $NaBH_3CN$, MeOH/$CH_3CO_2H$ (Synthesis 1975, 135–146)
71) S-Tr-N—Boc cysteinal, $ClCH_2CH_2Cl$ or THF, $NaBH(OAc)_3$ (J. Org. Chem. 1996, 61, 3849–3862)

72) TFA, CH$_2$Cl$_2$, Et$_3$SiH or (3:1:1) thioanisole/ethanedithiol/DMS
73) TFA, CH$_2$Cl$_2$
74) DPPA, Et$_3$N, toluene, HOCH$_2$CH$_2$SiCH$_3$ (Tetrahedron Lett. 1984, 25, 3515)
75) TBAF, THF
76) Base, TrSH or BnSH
77) Base, R$_2$X or R$_4$X
78) R$_3$NH$_2$, MeOH/CH$_3$CO$_2$H, NaBH$_3$CN
79) N$_2$H$_4$, KOH
80) Pd$_2$(dba)$_3$, P(o-tol)$_3$, RNH$_2$, NaOtBu, Dioxane, R$_1$NH$_2$ (Tetrahedron Lett. 1996, 37, 7181–7184).
81) Cyanamide.
82) Fmoc—Cl, sodium bicarbonate.
83) BnCOCl, sodium carbonate.
84) AllylOCOCl, pyridine.
85) Benzyl bromide, base.
86) Oxalyl chloride, DMSO.
87) RCONH$_2$.
88) Carbonyldiimidazole, neutral solvents (e.g., DCM, DMF, THF, toluene).
89) Thiocarbonyldiimidazole, neutral solvents (e.g., DCM, DMF, THF, toluene).
90) Cyanogen bromide, neutral solvents (e.g., DCM, DMF, THF, toluene).
91) RCOCl, Triethylamine
92) RNHNH$_2$, EDC.
93) RO$_2$CCOCl, Et$_3$N, DCM.
94) MsOH, Pyridine (J. Het. Chem., 1980, 607.)
95) Base, neutral solvents (e.g., DCM, toluene, THF).
96) H$_2$NOR, EDC.
97) RCSNH$_2$.
98) RCOCHBrR, neutral solvents (e.g., DCM, DMF, THF, toluene), (Org. Proc. Prep. Intl., 1992, 24, 127).
99) CH$_2$N$_2$, HCl. (Synthesis, 1993, 197).
100) NH2NHR, neutral solvents (e.g., DCM, DMF, THF, toluene).
101) RSO$_2$Cl, DMAP. (Tetrahedron Lett., 1993, 34, 2749).
102) Et$_3$N, RX. (J. Org. Chem., 1990, 55, 6037).
103) NOCl or Cl$_2$. (J. Org. Chem., 1990, 55, 3916).
104) H$_2$NOH, neutral solvents (e.g., DCM, DMF, THF, toluene).
105) RCCR, neutral solvents (DCM, THF, Toluene).
106) RCHCHR, neutral solvents (DCM, THF, Toluene).
107) H$_2$NOH, HCl.
108) Thiocarbonyldiimidazole, SiO$_2$ or BF$_3$OEt$_2$. (J. Med. Chem., 1996, 39, 5228).
109) Thiocarbonyldiimidazole, DBU or DBN. (J. Med. Chem., 1996, 39, 5228).
110) HNO$_2$, HCl.
111) ClCH$_2$CO$_2$Et (Org. Reactions, 1959, 10,143).
112) Morpholine enamine (Eur. J. Med. Chem., 1982, 17, 27).
113) RCOCHR'CN
114) RCOCHR'CO$_2$Et
115) Na$_2$SO$_3$
116) H$_2$NCHRCO$_2$Et
117) EtO$_2$CCHRNCO
118) RCNHNH$_2$.
119) RCOCO$_2$H, (J. Med. Chem., 1995, 38, 3741).
120) RCHO, KOAc.
121) 2-Fluoronitrobenzene.
122) SnCl$_2$, EtOH, DMF.
123) RCHO, NaBH$_3$CN, HOAc.
124) NH$_3$, MeOH.
125) 2,4,6-Me$_3$PhSO$_2$NH$_2$.
126) Et$_2$NH, CH$_2$Cl$_2$
127) MeOC(O)Cl, Et$_3$N, CH$_2$Cl$_2$
128) R$_2$NH$_2$, EDC, HOBT, Et$_3$N, CH$_2$Cl$_2$
129) DBU, PhCH$_3$
130) BocNHCH(CH$_2$STr)CH$_2$NH$_2$, EDC, HOBT, Et$_3$N, CH$_2$Cl$_2$
131) R$_2$NHCH$_2$CO$_2$Me, HBTU, HOBT, Et$_3$N, CH$_2$Cl$_2$
132) BocNHCH(CH$_2$STr)CH$_2$OMs, LiHMDS, THF
133) R$_2$NHCH$_2$CO$_2$Me, NaBH(OAc)$_3$, ClCH$_2$CH$_2$Cl or THF
134) R$_2$NHCH$_2$CH(OEt)$_2$, HBTU, HOBT, Et$_3$N, CH$_2$Cl$_2$
135) NaBH(OAc)$_3$, ClCH$_2$CH$_2$Cl or THF, AcOH.
136) Piperidine, DMF.
137) Pd(Ph$_3$P)$_4$, Bu$_3$SnH.
138) RCO$_2$H, EDC, HOBT, Et$_3$N, DCM.
139) RNH$_2$, neutral solvents.
140) RCHO, NaBH$_3$CN, HOAc.
141) RNCO, solvent.
142) RCO$_2$H, EDC or HBTU, HOBt, DIEA, CH$_2$Cl$_2$ or DMF.
143) RCOCl, Triethylamine
144) RSO$_2$Cl, Et$_3$N, CH$_2$Cl$_2$.
145) SnCl$_2$, EtOH, DMF.
146) RNH$_2$, EDC, HOBt, DIEA, CH$_2$Cl$_2$ or DMF.
147) Dibromoethane, Et$_3$N, CH$_2$Cl$_2$
148) Oxalyl chloride, neutral solvents.
149) LiOH, THF—MeOH.
150) Carbonyldiimidazole, neutral solvents (e.g., DCM, DMF, THF, toluene).
151) RNH$_2$, Et$_3$N, CH$_2$Cl$_2$.
152) Base, RX.
153) DBU, PhCH$_3$
154) DPPA, Et$_3$N, toluene (Synthesis 1985, 220)
155) SOCl$_2$, cat DMF.
156) ArH, Lewis Acid (AlCl$_3$, SnCl$_4$, TiCl$_4$), CH$_2$Cl$_2$.
157) H$_2$NCHRCO$_2$Et, neutral solvents.
158) BocHNCHRCO$_2$H, EDC OR HBTU, HOBt, DIEA, CH$_2$Cl$_2$ or DMF.
159) TFA, CH$_2$Cl$_2$.

All of the references cited above are hereby incorporated by reference herein.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A pharmaceutical preparation comprising a sterile pharmaceutical excipient and a compound represented by the general formula (V):

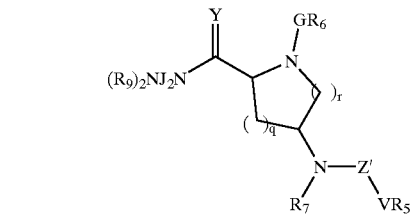

Formula V wherein, as valence permits,
Y is O or S;
Z' is SO$_2$, —(C=S)—, —(C=O)—, —(C=NH)—, or SO;

q and r represent, independently for each occurrence, an integer from 0 to 2;

V is absent or represents O, S, or $NR_8$;

G is absent or represents —C(=O)— or —$SO_2$—;

J, independently for each occurrence, represents H or substituted or unsubstituted lower alkyl or alkylene attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 8 members, which ring includes one or both occurrences of N;

$R_5$ represents substituted or unsubstituted alkyl (branched or unbranched), alkenyl (branched or unbranched), alkynyl (branched or unbranched), cycloalkyl, or cycloalkylalkyl;

$R_6$ represents substituted or unsubstituted aryl, aralkyl, heteroaryl, heteroaralkyl, heterocyclyl, heterocyclylalkyl, cycloalkyl, or cycloalkylalkyl; and $R_7$ represents substituted or unsubstituted aryl, aralkyl, heteroaryl, or heteroaralkyl.

2. The preparation of claim 1, wherein Y is O.

3. The preparation of claim 1, wherein the sum of q and r is less than 4.

4. The preparation of claim 1, wherein at least one occurrence of J is part of a heterocyclic ring which has from 5 to 8 members.

5. The preparation of claim 1, wherein $R_5$ represents a branched alkyl, cycloalkyl, or cycloalkylalkyl.

6. The preparation of claim 1, wherein $R_6$ includes at least one heterocyclyl ring.

7. The preparation of claim 1, wherein $R_7$ represents a substituted or unsubstituted phenyl alkyl.

8. The preparation of claim 1, wherein Z' is $SO_2$, —(C=O)—, or —(C=S)—.

9. The preparation of claim 1, wherein $NJ_2N$, taken together, represents a substituted or unsubstituted cyclic diamine.

10. The preparation of claim 9, wherein the cyclic diamine is a substituted or unsubstituted piperazine.

11. The preparation of claim 9, wherein the cyclic diamine is substituted with one or more groups selected from oxo, lower alkyl, and lower alkyl ether.

12. The preparation of claim 1, wherein $NJ_2$, taken together, represents a substituted or unsubstituted heterocyclic ring to which the other occurrence of N is attached.

13. The preparation of claim 1, wherein $NJR_9$, taken together, represents a substituted or unsubstituted heterocyclic ring to which the other occurrence of N is attached.

14. The preparation of claim 1, wherein one or both occurrences of J are substituted with one or more groups selected from lower alkyl, lower alkyl ether, lower alkyl thioether, amido, and oxo.

15. The preparation of claim 6, wherein said at least one heterocyclic ring is selected from thiophene, furan, oxazole, benzodioxane, pyrrole, and indole.

16. The preparation of claim 7, wherein $R_7$ is a substituted or unsubstituted benzyl group.

17. The preparation of claim 16, wherein the benzyl group is substituted with one or more groups selected from halogen, hydroxyl, lower alkyl, nitro, cyano, lower alkyl ether, and lower alkyl thioether.

18. The preparation of claim 1, wherein $R_8$ is H or a lower alkyl.

19. A pharmaceutical preparation comprising a sterile pharmaceutical excipient and a compound represented by the general formula (VI):

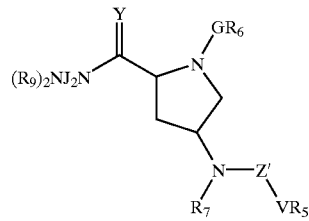

Formula VI wherein, as valence permits,

Y is O or S;

Z' is $SO_2$, —(C=S)—, —(C=O)—, —(C=NH)—, or SO;

V is absent or represents O, S, or $NR_8$;

G is absent or represents —C(=O)— or —$SO_2$—;

J, independently for each occurrence, represents H or substituted or unsubstituted lower alkyl or alkylene attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 8 members, which ring includes one or both occurrences of N;

$R_5$ represents substituted or unsubstituted alkyl (branched or unbranched), alkenyl (branched or unbranched), alkynyl (branched or unbranched), cycloalkyl, or cycloalkylalkyl;

$R_6$ represents substituted or unsubstituted aryl, aralkyl, heteroaryl, heteroaralkyl, heterocyclyl, heterocyclylalkyl, cycloalkyl, or cycloalkylalkyl; and $R_7$ represents substituted or unsubstituted aryl, aralkyl, heteroaryl, or heteroaralkyl.

20. The preparation of claim 19, wherein Y is O.

21. The preparation of claim 19, wherein at least one occurrence of J is part of a heterocyclic ring which has from 5 to 8 members.

22. The preparation of claim 19, wherein $R_5$ represents a branched alkyl, cycloalkyl, or cycloalkylalkyl.

23. The preparation of claim 18, wherein $R_6$ includes at least one heterocyclyl ring.

24. The preparation of claim 19, wherein $R_7$ represents a substituted or unsubstituted phenyl alkyl.

25. The preparation of claim 19, wherein Z' is $SO_2$, —(C=O)—, or —(C=S)—.

26. The preparation of claim 19, wherein $NJ_2N$, taken together, represents a substituted or unsubstituted heterocyclic ring.

27. The preparation of claim 26, wherein the heterocyclic ring is a substituted or unsubstituted piperazine.

28. The preparation of claim 26, wherein the heterocyclic ring is substituted with one or more groups selected from oxo, lower alkyl, and lower alkyl ether.

29. The preparation of claim 19, wherein $NJ_2$, taken together, represents a substituted or unsubstituted heterocyclic ring to which the other occurrence of N is attached.

30. The preparation of claim 19, wherein $NJR_9$, taken together, represents a substituted or unsubstituted heterocyclic ring to which the other occurrence of N is attached.

31. The preparation of claim 19, wherein one or both occurrences of J are substituted with one or more groups selected from lower alkyl, lower alkyl ether, lower alkyl thioether, amido, and oxo.

32. The preparation of claim 23, wherein said at least one heterocyclic ring is selected from thiophene, furan, oxazole, benzodioxane, pyrrole, and indole.

33. The preparation of claim 24, wherein $R_7$ is a substituted or unsubstituted benzyl group.

34. The preparation of claim 33, wherein the benzyl group is substituted with one or more groups selected from halogen, hydroxyl, lower alkyl, nitro, cyano, lower alkyl ether, and lower alkyl thioether.

35. The preparation of claim 19, wherein $R_8$ is H or a lower alkyl.

36. The preparation of claim 1 or 19, wherein the preparation is non-pyrogenic.

37. A method for inhibiting activation of a hedgehog pathway in a cell, comprising contacting the cell with a preparation of claim 1 or 19 in a sufficient amount to inhibit hedgehog signaling.

38. The method of claim 37, wherein the cell is normal.

39. The method of claim 37, wherein the cell has a patched loss-of-function phenotype, a hedgehog gain-of-function phenotype, or a smoothened gain-of-function phenotype.

40. The method of claim 37, wherein the preparation inhibits ptc loss-of-function, hedgehog gain-of-function, or smoothened gain-of-function mediated signal transduction with an $ED_{50}$ of 1 µM or less.

41. The method of claim 37, wherein the preparation inhibits ptc loss-of-function, hedgehog gain-of-function, or smoothened gain-of-function mediated signal transduction with an $ED_{50}$ of 1 nM or less.

42. The method of claim 37, wherein the preparation is administered as part of a therapeutic or cosmetic application.

43. The method of claim 42, wherein the therapeutic or cosmetic application is selected from regulation of neural tissues, bone and cartilage formation and repair, regulation of spermatogenesis, regulation of smooth muscle, regulation of lung, liver and other organs arising from the primitive gut, regulation of hematopoietic function, and regulation of skin and hair growth.

* * * * *

UNITED STATES PATENT AND TRADEMARK OFFICE
CERTIFICATE OF CORRECTION

PATENT NO.      : 6,552,016 B1
DATED           : April 22, 2003
INVENTOR(S)     : Baxter et al.

It is certified that error appears in the above-identified patent and that said Letters Patent is hereby corrected as shown below:

<u>Column 94,</u>
Line 48, replace "claim 18" with -- claim 19 --.

Signed and Sealed this

Ninth Day of March, 2004

JON W. DUDAS
*Acting Director of the United States Patent and Trademark Office*